(12) United States Patent
Hirata et al.

(10) Patent No.: US 6,716,896 B2
(45) Date of Patent: Apr. 6, 2004

(54) METHOD FOR PRODUCTION OF ESTERIFIED PRODUCT AND APPARATUS THEREFOR

(75) Inventors: Tsuyoshi Hirata, Kobe (JP); Hiromichi Tanaka, Takatsuki (JP); Tsutomu Yuasa, Osaka (JP)

(73) Assignee: Nippon Shokubai Co., Ltd. (JP)

( * ) Notice: Subject to any disclaimer, the term of this patent is extended or adjusted under 35 U.S.C. 154(b) by 8 days.

(21) Appl. No.: 10/041,372

(22) Filed: Jan. 8, 2002

(65) Prior Publication Data

US 2002/0087028 A1 Jul. 4, 2002

Related U.S. Application Data

(62) Division of application No. 09/399,567, filed on Sep. 20, 1999.

(30) Foreign Application Priority Data

Sep. 22, 1998 (JP) ............................................ 10-268121
Nov. 18, 1998 (JP) ............................................ 10-328684
Apr. 6, 1999 (JP) ............................................ 11-99335

(51) Int. Cl.$^7$ ................................................. C08K 3/00
(52) U.S. Cl. ........................ 524/5; 524/2; 524/3; 524/4; 560/224
(58) Field of Search ............................. 560/224; 524/5, 524/2, 3, 4, 72, 318.41

(56) References Cited

U.S. PATENT DOCUMENTS

| 3,431,181 A | 3/1969 | Bouniot |
| 3,988,213 A | 10/1976 | Yoshida et al. |
| 4,021,310 A | 5/1977 | Shimizu et al. |
| 4,774,178 A | 9/1988 | Egerer et al. |

FOREIGN PATENT DOCUMENTS

| EP | 0 799 807 | 10/1997 |
| EP | 0799807 A3 * | 3/1998 |
| EP | 0 884 290 | 12/1998 |
| JP | 59-18338 | 4/1984 |
| JP | 7-118046 | 5/1995 |
| JP | 07-224004 | 8/1995 |
| JP | 09-086990 | 3/1997 |
| JP | 09-286645 | 11/1997 |
| JP | 10-153599 | 6/1998 |

OTHER PUBLICATIONS

The Merck Index, 12th Edition, 1996, pp. 1250 and 825.

* cited by examiner

*Primary Examiner*—Paul J. Killos
*Assistant Examiner*—Taylor Victor Oh
(74) *Attorney, Agent, or Firm*—Mathews, Collins, Shepherd & McKay, P.A.

(57) ABSTRACT

A method for the production of an esterified product which can prevent the occurrence of a gel-like substance during the separation and removal of the water formed by the reaction in the esterification reaction or during the expulsion of a dehydrating solvent by distillation after the esterification reaction by causing an antigelling agent to act on the distillate and consequently permits efficient production of the esterified product of high quality, and an apparatus therefor are to be provided. To be specific, a method for the production of an esterified product of this invention relates to a method for the production of an esterified product by the esterification reaction of an alcohol represented by the following formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid, wherein said method comprises acting an antigelling agent on a distillate.

1 Claim, 8 Drawing Sheets

A larger part (compartment) can be also used as a preserving part

METHOD FOR PRODUCTION OF ESTERIFIED PRODUCT AND APPARATUS THEREFOR

This application is a division of Ser. No. 09/399,567 filed Sep. 20, 1999.

BACKGROUND OF THE INVENTION

1. Field of the Invention

This invention relates to a method for the production of an esterified product and an apparatus therefor. More particularly, the invention relates to a method for efficiently producing a (meth)acrylic ester (occasionally referred to briefly as "esterified product" in the present specification) of high quality by the esterification reaction of an alcohol with (meth)acrylic acid, and to an apparatus therefor. Especially, in quantity production of an esterified product on a commercial scale by continuous operation of an apparatus for production, this invention relates to a method for the production of the esterified product excelling in production efficiency, and the apparatus therefor.

2. Description of the Related Art

A varying alkoxy polyalkylene glycol mono(meth)acrylic ester type monomer component which forms a raw material for a polymer component to be used in cement dispersants, and pigment dispersants for calcium carbonate, carbon black, ink, and other pigments, scale removers, dispersants for a slurry of gypsum and water, dispersants for CWM, thickeners, and etc. can be obtained by subjecting an alkoxy polyalkylene glycol and (meth)acrylic acid to the esterification reaction. Since this esterification reaction by-produces water simultaneously, the reaction which is equilibratory in nature ceases to proceed in the direction of forming the esterified product unless the water formed by the reaction is removed from the reaction system (namely when the water formed by the reaction is suffered to accumulate therein).

As found in Controls 1 and 2 cited in JP-A-09-328,346, for example, the synthesis of a varying alkoxy polyalkylene glycol mono(meth) acrylic ester type monomer component which forms a raw material for a polymer component to be used in a cement dispersant resorts to a principle of providing a water separator for accomplishing the separation of the water formed by the reaction. More specifically, this publication discloses a method for synthesizing an expected esterified product by using a reaction vessel designed for the synthesis of an alkoxy polyalkylene glycol mono(meth) acrylic ester type monomer by the esterification reaction and adapted to permit separation of the water formed by the reaction by providing a reaction vessel (a separable flask) with a thermometer, a stirrer, and a water separator, performing the esterification reaction by placing methacrylic acid, methoxy polyethylene glycol (an average addition mol number of oxyethylene groups of 10 mols), sulfuric acid (Control 1) or paratoluene sulfonic acid (Control 2) as an acid catalyst, phenothiazine as a polymerization inhibitor, and cyclohexane as a solvent in the reaction vessel and meanwhile stirring and heating the reactants and consequently effecting distillation of a cyclohexane-water azeotropic mixture under normal pressure, removing the water formed by the reaction with the water separator, and refluxing the cyclohexane, and after the completion of the esterification reaction, expelling the used cyclohexane by distillation.

No technical tasks other than the idea of providing a water separator for separating and removing the water formed by the reaction during the course of the esterification reaction or the idea of expelling a dehydrating solvent by distillation after the completion of the esterification reaction using a dehydrating solvent as disclosed in the patent publication mentioned above has heretofore been reported to the literature.

SUMMARY OF THE INVENTION

An object of this invention, therefore, is to solve the technical problems of the prior art and to provide a method for the production of an esterified product and an apparatus therefor.

Another object of this invention is to provide a method for the production of an esterified product which prevents the occurrence of a gel-like substance during the separation and removal of the water formed by the reaction by causing an antigelling agent to act on the distillate and consequently permits efficient production of the esterified product of high quality, and an apparatus therefor.

Still another object of this invention is to provide a method for the production of an esterified product which prevents the occurrence of a gel-like substance during the expulsion of a dehydrating solvent by distillation after the esterification reaction and consequently permits efficient production of the esterified product of high quality, and an apparatus therefor.

Further object of this invention is to provide a method for the production of an esterified product by the esterification reaction of an alcohol and (meth)acrylic acid which always prevents effectively the occurrence of a gel-like substance on a path for expulsion by distillation by causing a sufficient amount of an anti-gelling agent-containing solution to act on the distillate and consequently permits efficient and inexpensive formation of the esterified product of high quality, and an apparatus therefor.

Still further object of this invention is to provide a method for the production of an esterified product which, when a dehydrating solvent is used in the production of the esterified product, represses growth of an amount of a residue of condensate returned to a reaction tank besides fulfilling the object mentioned above as small as possible by causing a sufficient amount of an antigelling agent-containing solution to act on the distillate and consequently permits efficient and inexpensive formation of the esterified product of high quality, and an apparatus therefor.

The prevent inventors, while continuing a diligent study with a view to attaining efficient formation of an esterified product of high quality, have found that a gel-like substance is formed during the condensation of a distillate arising from the esterification reaction (an azeotropic mixture of a solvent with water formed by the reaction) and that this gel-like substance gives birth to numerous technical problems as evinced by the fact that a part of this gel-like substance, on being refluxed in conjunction with the solvent, persists as an extraneous substance in the reaction tank, mingles into a finished product (for example, a cement dispersant, a pigment dispersant, a scale remover, a dispersant for a slurry of gypsum and water, a dispersant for CWM, and a thickener), and forms a cause for degrading the performance and quality of the product, that the gel-like substance, when the esterified product is produced in a large quantity on a commercial scale, cumulatively adheres to the inner wall of a piping and a device (for example, a condenser), i.e. means for condensing, separating, and removing water formed by the reaction, and eventually induces possible degradation of the heat-exchange efficiency during the condensation, that the deposit of the gel-like substance, when the operation is repeated or continued with a view to attaining quantity production on a commercial scale, impairs the flow of the fluid (mainly the liquid resulting from the condensation) in the condenser and the piping, possibly induces clogging thereof, and consequently compels the operation to be periodically suspended for permitting removal of the gel-like substance from the interior of the condenser and the piping by washing.

The present inventors have further found that the expulsion of the dehydrating solvent to be effected in the form of an azeotropic mixture with added water after the completion of the esterification reaction by the use of a dehydrating solvent reflux system fulfilling the purpose of separating and removing the water formed by the reaction forms a gel-like substance besides the gel-like substance formed during the esterification reaction and that the distillate containing this gel-like substance, when suffered to reach the step of polymerization and eventually mingle into the finished product (for example, a cement dispersant, a pigment dispersant, a scale remover, a dispersant for a slurry of gypsum and water, a dispersant for CWM, and a thickener), degrades the performance and quality of the product in the same manner as described above.

The present inventors, therefore, have continued a diligent study in search of a solution for the problems mentioned above and also a method for efficiently forming an esterified product with high quality and have consequently ascertained themselves that a gel-like substance to be generated during the separation and removal of water formed by the reaction or during the expulsion of a dehydrating solvent by distillation consists mostly of a poly(meth)acrylic acid and that this gel-like substance is formed (as gelated by a liquid-phase reaction) when either of the raw materials, i.e. alcohol and (meth)acrylic acid, for the esterification reaction is used in an excess amount for the purpose of accelerating the esterification reaction or a raw material having a lower boiling point is used in an excess amount for the purpose of facilitating the isolation of the target esterified product by distillation and consequently the raw material of the low boiling point remains in an unaltered form after the completion of the esterification reaction and a part of the unaltered raw material is expelled as an azeotropic mixture with water (an axeotropic mixture of a solvent and water formed by the reaction) or expelled in conjunction with the dehydrating solvent by distillation and then condensed and liquified. On the basis of this mechanism for the occurrence of the gel-like substance, they have discovered a measure for very effectively preventing the occurrence of the gel-like substance mentioned above.

Further, the present inventors have continued a diligent study with a view to solving the technical problem mentioned above and have consequently made a discovery that the technical problem can be solved by utilizing as a solution of an antigelling agent intended to act on the distillate emanating from the reaction tank a solution containing at least a part of a condensate, particularly a mixture of a part of a condensate (especially a part of a residue of condensate remaining after the separation and removal of water formed by the reaction and to be returned to the reaction tank) with a solution of an antigelling agent. The present invention has been perfected as a result.

Specifically, the objects of this invention can be accomplished by a method for the production of an esterified product by the esterification reaction of an alcohol represented by the formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2$, may be added either in a block form or in a random form, and n represents an average addition mol number of oxyalkylene groups and is in the range of 0 to 300, with (meth)acrylic acid, wherein said method comprises acting an antigelling agent on a distillate.

The objects of this invention can be also accomplished by a method for the production of an esterified product by the esterification reaction of an alcohol represented by the formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid in the presence of a dehydrating agent, wherein said method comprises expelling by distillation water formed during the esterification reaction in conjunction with the dehydrating solvent, condensing and liquefying the distillate containing the water, separating and removing the water from the condensate resulting from the condensation and liquefaction, and returning to a reaction tank a residue of condensate containing the dehydrating solvent and remaining after the separation and removal of the water, and causing an antigelling agent solution containing a part of the residue of condensate and an antigelling agent to act on the distillate during the course of the esterification reaction.

The objects of this invention can be further accomplished by a method for the production of an esterified product by the esterification reaction of an alcohol represented by the formula (1):

$$R^1O(RO)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$ , may be added either in a block form or in a random form, and n represents an average addition mol number of oxyalkylene groups and is in the range of 0 to 300, with (meth)acrylic acid in the presence of a dehydrating agent, wherein said method comprises further a step of expelling by distillation the dehydrating solvent after the completion of the esterification reaction while causing an antigelling agent to act on the distillate containing the dehydrating solvent.

The objects of this invention can be furthermore accomplished by an apparatus for the esterification to be used for the method of this invention for producing an esterified product, which comprises a reaction tank for the esterification reaction of an alcohol represented by the formula (1):

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid, a condenser for condensing and liquefying a distillate emanating from the reaction tank, an antigelling agent-supplying mechanism disposed at at least one point on a connecting pipe intervening between the reaction tank and the condenser, and a water separator for separating and removing water from the condensate.

Now, the advantages obtained by the method and the apparatus according to this invention will be described below.

Firstly, the advantages enjoyed by the method for the production of an esterified product according to this invention which comprises causing an antigelling agent to act on the distillate during the course of the esterification reaction will be described below.

(1) The method for the production of an esterified product according to this invention, by causing an antigelling agent to act on the distillate, is enabled to prevent the formation of a gel-like substance and prevent the paths in such devices as a condenser and pipes from blockage and protect the resultant esterified product against degradation of quality causable by the reflux of the distillate resulting from separation and removal of water formed by the reaction to the reaction system and protect the finished product such as a cement dispersant formed by using the esterified product against degradation of performance and quality.

(2) Particularly, the method can derive conspicuously the function and effect indicated in (1) above by causing the antigelling agent to act in the region for condensing the distillate.

(3) By the same token, the method can derive more conspicuously the function and effect indicated in (1) above by causing the antigelling agent to act inside the condenser (preferably in the proximity of the top of the condenser column).

(4) The method, by mixing the antigelling agent with a solvent similar in kind to the dehydrating solvent used for expelling the water formed by the reaction as an azeotropic mixture and heating the resultant mixture, is enabled not only to manifest the function and effect indicated in (1) to (3) above but also to obviate the necessity for providing such an additional device as is capable of separating the dehydrating solvent and the solvent used for dissolving the antigelling agent from each other and refluxing the dehydrating solvent exclusively into the reaction system, facilitate the management of temperature in the reaction system, and avoid complicating the control system because the ref lux of all these components into the reaction system induces no change in the composition of the azeotropic distillate emanating from the interior of the reaction system.

(5) The method, when the antigelling agent possesses solubility in the solvent of (4) above and consequently causes the antigelling agent to be dissolved in the solvent and allowed to act thereon, enjoys such advantages as not only manifesting the function and effect indicated in (1) to (4) above but also facilitating the handling of the agent; permitting the agent to act promptly on what results from condensing and liquefying the distillate by the method of contact such as parallel contact; and allowing adoption of various techniques for enabling the antigelling agent to function very efficiently as by blowing the gaseous distillate into the liquid formed by dissolving the antigelling agent in the solvent, for example, and consequently attaining the required contact of the antigelling agent simultaneously with the liquefaction thereof.

(6) The method, when the alcohol of the formula (1), as one of the raw materials, has the average addition mol number, n, of the oxyalkylene group thereof in the range of 2 to 300, is at an advantage in not merely manifesting the function and effect indicated in (1) to (5) above but also affording a monomer component useful as a raw material for a polymer destined to serve as a main component of a cement dispersant as evinced by the fact that the esterified product obtained by the esterification reaction has been deprived effectively of such impurities as a gel-like substance and a cement dispersant made by using this esterified product excels in slump-retaining ability and water-reducing ability as well as in dispersion properties.

Secondly, the advantages enjoyed by the method for the production of an esterified product characterized by performing the esterification reaction meanwhile expelling by distillation the water arising during the esterification reaction in conjunction with the dehydrating solvent, condensing and liquefying the distillate containing the water, separating and removing the water from the condensate resulting from the condensation and liquefaction, and returning to the reaction tank the residue of condensate containing the dehydrating solvent remaining after the separation and removal of the water, and causing an antigelling agent solution containing a part of the residue of condensate and an antigelling agent to act on the distillate during the course of the esterification reaction will be described below.

(a) The method, by causing the antigelling agent solution mentioned above to act on the distillate during the course of the esterification reaction performed by a procedure of expelling by distillation water and a dehydrating solvent which water is formed during the esterification reaction performed in the presence of the dehydrating agent optionally together with an acid catalyst and a polymerization inhibitor, condensing and liquefying the distillate containing the water, separating and removing the water from the condensate resulting from condensation and liquefaction, and returning a residue of the condensate containing the dehydrating solvent remaining after the separation and removal of the water, enjoys similarly to (1) above the advantages of allowing the inner wall surfaces of the pipes and the condenser disposed on the paths of distillation tending to generate a gel-like substance in consequence of the adhesion of liquefied distillate to be always kept in a wet state by supply of an ample amount of the solution containing the antigelling agent thereby affording constant and effective prevention of the occurrence of a gel-like substance on the paths of distillation mentioned above and permitting efficient and inexpensive production of the esterified product with high quality and consequently allowing the finished product such as a cement dispersant formed by using the esterified product to suffer from no degradation of performance or quality.

(b) The product can repress to the fullest possible extent the increase of the amount of the residue of condensate to be returned to the reaction tank and permit efficient and inexpensive production of the esterified product with still higher quality.

(c) The method, particularly by causing the antigelling agent solution to act in the region for condensing and liquefying the distillate containing the water, namely in the region for generating a gel-like substance in consequence of the deposition of the liquefied distillate on the paths for distillation, can efficiently and effectively prevent the occurrence of the gel-like substance and more conspicuously derive the function and effect indicated in (a) and (b) above.

(d) The method, also by causing the antigelling agent solution to act similarly in the proximity of the top of condenser column for condensing and liquefying the distillate mentioned above, can efficiently and effectively prevent the occurrence of the gel-like substance and more conspicuously derive the function and effect indicated in (a) and (b) above.

(e) The method, by causing the antigelling agent to be dissolved in a solvent similar in kind to the dehydrating solvent being used for distilling the water formed by the reaction in the form of an azeotropic mixture, is at an advantage as in (4) above in not only manifesting the function and effect indicated above but also enabling the antigelling agent solution formed by using the antigelling agent to act promptly on what has resulted from condensing and liquefying the distillate, i.e. an azeotropic mixture with the dehydrating solvent, by the method of contact such as parallel contact because it possesses solubility therein. Further, the method facilitates management of temperature in the reaction tank and avoids complicating the control system because the reflux of these components into the reaction tank brings no change in the composition of the distillate emanating azeotropically from the interior of the reaction tank and avoids varying the azeotropic temperature.

Thirdly, the advantages to be enjoyed by the apparatus for producing an esterified product comprising a reaction tank for performing the esterification reaction, a condenser for condensing and liquefying a distillate emanating from the reaction tank, an antigelling agent-supplying mechanism disposed at at least one point on a connecting pipe intervening between the reaction tank and the condenser, and a water separator for separating and removing water from the condensate will be described below.

(A) The apparatus, by disposing the antigelling agent-supplying mechanism at at least one point on the connecting pipe intervening between the reaction tank and the condenser and making it to act on the distillate, can derive the same effects as those indicated in (a) to (e) above. The apparatus is also at an advantage in affording an esterified product effectively deprived of such impurities as a gel-like substance, enabling a cement dispersant made by using this product to excel not only in dispersing properties but also in such service performances as slump-retaining properties and water-reducing properties, and allowing the product to serve as a monomer component useful as a raw material for a polymer as a main component for a cement dispersant.

(B) The apparatus, by disposing as the antigelling agent-supplying mechanism a nozzle part for acting the antigelling agent solution in the proximity of the top of condenser column, namely a site at which the gel-like substance is generated in consequence of the adhesion of the liquefied distillate to the paths of distillation, is enabled to afford efficient and effective prevention of the occurrence of the gel-like substance and consequently manifest the function and effect indicated in (A) above conspicuously.

(C) The apparatus, by having the nozzle part so disposed as to supply the antigelling agent solution upwardly, is enabled to obtain the function and effect indicated in (A) and (B) still more conspicuously.

(D) The apparatus, by being provided as the antigelling agent-supplying mechanism with a first supply route for supplying the antigelling agent solution from the storage part for the antigelling agent solution to the nozzle part and a second supply route for supplying a part of the condensate (particularly a part of a residue of condensate) to the nozzle part, is enabled to obtain thorough the function and effect indicated in (A) to (C) above.

Fourthly, the advantages enjoyed by the method for producing an esterified product characterized by including a step of causing the antigelling agent to act on the distillate containing the dehydrating solvent in the step of expelling by distillation the dehydrating solvent after the completion of the esterification reaction will be described below.

(i) Besides being capable of effectively preventing the formation of a gel-like substance and protecting the paths in the devices such as a condenser and pipes against blockage, the method, when the device adopted during the circulation of the dehydrating solvent during the esterification reaction is utilized also during the expulsion of the dehydrating solvent by distillation, precludes a possibility of the gel-like substance formed during the expulsion of the dehydrating solvent by distillation being brought into the reaction system during the reflux into the reaction system of the distillate remaining after separation and removal of the water formed by the reaction in the subsequent batch of the esterification reaction as experienced in the repeated (or continuously) operation of the apparatus for the production of the esterified product and consequently avoids inducing decline of the quality and performance of the esterified product. The method, as a result, does not allow the finished product such as a cement dispersant made by using the esterified product to suffer any decline in the performance and quality thereof owing to the gel-like substance.

(ii) The method, by causing the antigelling agent to act in the region for condensing the distillate containing the dehydrating solvent thereby enabling the antigelling agent to act very efficiently and effectively on a material inducing the occurrence of the gel-like substance such as the unaltered low boiling raw material contained in the distillate, is enabled to obtain the function and effect indicated in (i) above very conspicuously.

(iii) The method can manifest a function and effect on a par with that indicated in (ii) above because it is capable of allowing the antigelling agent to act very efficiently and effectively on a material inducing the occurrence of the gel-like substance such as the unaltered low boiling raw material contained in the distillate.

(iv) The method, besides being enabled to manifest the function and effect indicated in (i) to (iii) above by causing the antigelling agent to act as mixed with water during the expulsion of the dehydrating solvent and water by azeotropic distillation, is exceptionally advantageous in producing the action in question promptly on the unaltered low boiling raw material dissolved in the water which accounts for the greater part of the distillate being expelled (distilled) azeotropically with water from the solution in the system because the distillate is composed substantially wholly of water.

(v) The method, besides being capable of manifesting the function and effect indicated in (i) to (iv) above because the antigelling agent can be made to act as dissolved in water when the antigelling agent is soluble in water, enjoys such advantages as permitting easy handling of the antigelling agent; permitting the agent to act promptly on what results from condensing and liquefying the distillate by the method of contact such as parallel contact; and allowing adoption of various techniques for enabling the antigelling agent to function very efficiently as by blowing the gaseous distillate into the liquid formed by dissolving the antigelling agent in the solvent, for example, and consequently attaining the required contact of the antigelling agent simultaneously with the liquefaction thereof.

The above and other objects, features, and advantages of the present invention will become clear from the following description of the preferred embodiment.

DESCRIPTION OF THE PREFERRED EMBODIMENTS

Figure 1:
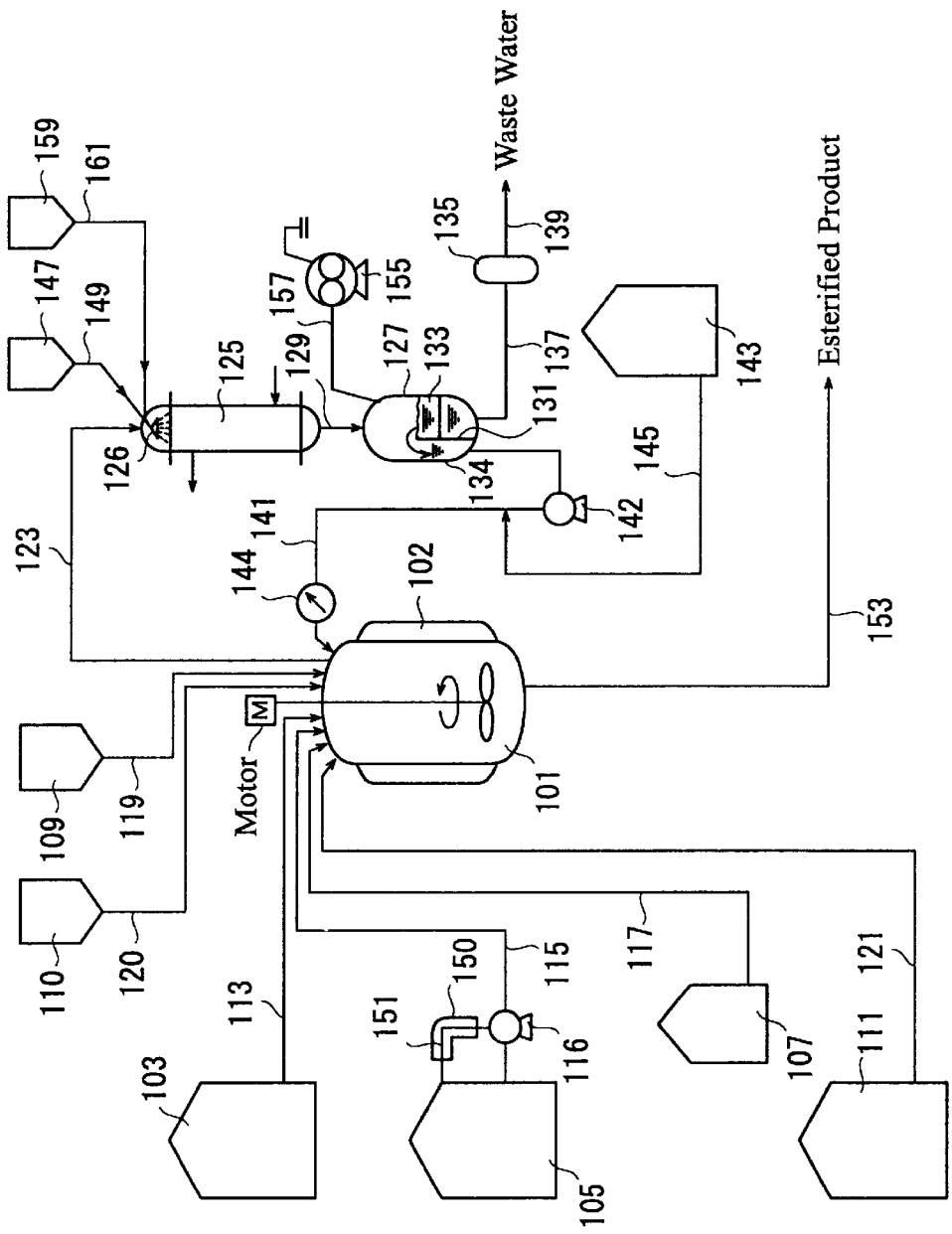
FIG. 1 is a schematic diagram illustrating the construction of a typical apparatus to be used in the method of production of an esterified product according to this invention.

Now, this invention will be described in detail below.

According to the first aspect, this invention is to provide a method for the production of an esterified product by the esterification reaction of an alcohol represented by the following formula (1) (occasionally referred to briefly as "alcohol" in the present specification):

$$R^1O(R^2O)_nH \tag{1}$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid, wherein said method comprises acting an antigelling agent on a distillate, particularly a distillate containing water formed as a by-product by the esterification reaction (occasionally referred to briefly as "reaction-forming water" in the present specification).

First, the esterification reaction according to this invention will be described in detail and then the requirement for construction which characterizes the first aspect will be described here.

Now, the esterification reaction in the method of this invention for the production of an esterified product will be described.

One embodiment of the esterification reaction in the method of this invention for production of the esterified product will be briefly described below. The reaction system (reaction tank) is charged with an alcohol and (meth)acrylic acid as raw materials, a dehydrating solvent, an acid catalyst, and a polymerization inhibitor. The resultant mixture in the system is left undergoing esterification reaction at a fixed temperature until the ratio of esterification reaches a prescribed level.

An alcohol which may be used as a raw material in the esterification reaction according to this invention is a compound of the above formula (1).

In the formula (1) mentioned above, $R^1$ represents a hydrocarbon group of 1 to 30 carbon atoms. If $R^1$ represents a hydrocarbon group having more than 30 carbon atoms, a copolymer obtained by copolymerizing the esterified product between the alcohol of the formula (1) and (meth) acrylic acid with (meth)acrylic acid, for example, will suffer degradation of water solubility and degradation of service performance such as, for example, cement-dispersing properties. The proper range of $R^1$ varies with the kind of intended use of the product. When the product is used as a raw material for a cement dispersant, for example, $R^1$ may preferably stand for a straight or branched-chain alkyl or aryl group of 1 to 18 carbon atoms. As concrete examples of $R^1$, alkyl groups such as methyl, ethyl, n-propyl, isopropyl, n-butyl, tert-butyl, pentyl, hexyl, octyl, nonyl, 2-ethylhexyl, decyl, dodecyl, undecyl, tridecyl, tetradecyl, pentadecyl, hexadecyl, heptadecyl, octadecyl, nonadecyl, eicocyl, heneicocyl, and dococyl; aryl groups such as phenyl; alkylphenyl groups such as benzyl and nonylphenyl; cycloalkyl groups such as cyclohexyl; and alkenyl groups and alkinyl groups may be cited. When the esterified product is used as a raw material for a cement dispersant, methyl, ethyl, propyl, butyl, and phenyl may be particularly favorable among other groups mentioned above.

$R^2O$ represents an oxyalkylene group of 2 to 18 carbon atoms, preferably 2 to 8 carbon atoms. If $R^2O$ represents an oxyalkylene group of more than 18 carbon atoms, a copolymer obtained by copolymerizing the esterified product between the alcohol of the formula (1) and (meth)acrylic acid with (meth)acrylic acid, for example, will suffer degradation of water solubility and degradation of service performance such as, for example, cement-dispersing properties. As concrete examples of $R^2O$, oxyethylene, oxypropylene, oxybutylene, and oxystyrene may be cited. Of these groups, oxyethylene, oxypropylene, and oxybutylene may prove favorable. The repeating units, $R^2O$, may be either the same or different. When the repeating units, $R^2O$, are variable, namely when the repeating units occur in not less than two species, these individual repeating units, $R^2O$, may be added in a block form or in a random form.

In the formula (1), n denotes a numeral falling in the range of 0 to 300, preferably 2 to 300, and represents an average addition mol number of the repeating units, $R^2O$ (oxyalkylene group). If n exceeds 300, the esterified product between the compound of the formula (1) and (meth)acrylic acid will suffer a degraded polymerizing properties. This average addition mol number, n, has the optimum range thereof varying with the purpose for which the esterified product obtained by the esterification reaction is used. When the esterified product is used as a raw material for a cement dispersant, for example, the average addition mol number, n, may be preferably in the range of 2 to 300, more preferably in the range of 5 to 200, and most preferably in the range of 8 to 150. When it is used in a thickener, the average addition mol number, n, may be preferably in the range of 10 to 250, more preferably in the range of 50 to 200. When n is 0, the aforementioned $R^1$ may be preferably a hydrocarbon group of not less than four carbon atoms from the viewpoint of solubility in water and boiling point. The reason for thus specifying the $R^1$ is that when n in the formula (1) is 0, particularly in the case of methanol or ethanol, the alcohol as the raw material is partially expelled by distillation out of the system and the esterified product aimed at is obtained in an unduly low yield because these alcohols, on account of a low boiling point, is vaporized together with reaction-forming water and further dissolved in water.

In the method of this invention, the alcohol as the raw material of the aforementioned formula (1) may be used either singly or in the form of a mixture of two or more species. The mode of using the raw material alcohol in the form of a mixture of two or more species does not need to be limited particularly. The mixture of not less than two species having at least one of the factors, $R^1$, $R^2O$, and n varied may suffice as the mode of use. As concrete examples of the mode of preferable use, the case in which $R^1$ is composed of the two species, methyl and butyl; the case in which $R^2O$ is composed of the two species, oxyethylene and oxypropylene; the case in which n is composed of two species, one of 1 to 10 and another of 11 to 100; and the case in which such modes are suitably combined may be cited.

As concerns the (meth)acrylic acid which can be used in the esterification reaction contemplated by this invention, acrylic acid and methacrylic acid may be independently used or they may be used in a mixed state. Their mixing ratio may be selected in an arbitrary range.

From the stoichiometrical point, the mixing ratio of the raw materials mentioned above which may be used in the esterification reaction according to this invention is 1:1 reduced as a molar ratio. Actually, however, it does not need to be particularly restricted so long as it fall in a range in which the esterification reaction of an alcohol with (meth)acrylic acid efficiently proceeds. Generally, for the purpose of expediting the esterification reaction by using either of the raw materials in an excess amount and from the viewpoint of purifying the esterified product as aimed at, the one raw material having a lower boiling point and allowing easier expulsion by distillation than the other raw material may be used in an excess amount. Further, in this invention, since part of the (meth)acrylic acid of a lower boiling point may be distilled and expelled from the reaction system while the water formed by the reaction and the dehydrating solvent are azeotroped during the esterification reaction, the amount of the (meth)acrylic acid to be used (charged) may be preferably in excess of the stoichiometrically calculated amount relative to the amount of the alcohol to be used (charged). Specifically, the amount of the (meth)acrylic acid to be used is generally in the range of 1.0 to 30 mols, preferably in the range of 1.2 to 10 mols, more preferably in the range of 1.5 to 10 mols, and most desirably in the range of 2 to 10 mols, based on 1 mol of the alcohol. If the amount of the (meth)acrylic acid to be used is less than 1.0 mol, based on 1 mol of the alcohol, the esterification reaction would not smoothly proceed and the yield of the esterified product would be insufficient. Conversely, if the amount exceeds 30 mols, the excess would bring no proportionate addition to the yield and only impair the economy of the production.

Alternatively, it is commendable to adjust the amount, p parts by weight, of the polyalkylene glycol (meaning the alcohol wherein n in the formula (1) is in the range of 1 to 300) to be used and the amount, q parts by weight, of the (meth)acrylic acid to be used so as to satisfy the relation of the following formula:

$$40 \leq [(p/n^{1/2})/q] \times 100 \leq 200$$

wherein n represents an average addition mol number of the oxyalkylene group, and is in the range of 1 to 300.

The fact that the amounts of the polyalkylene glycol and the methacrylic acid to be used are specified so as to satisfy the relation mentioned above is preferable, because, when the esterification reaction is carried out by allowing the (meth)acrylic acid to be present in an excess amount relative to the polyalkylene glycol, the alkoxy polyalkylene glycol mono(meth)acrylic acid type monomer consequently obtained exists in the form of a mixture containing (meth)acrylic acid and the polycarboxylic acid type copolymer can be produced by subjecting this mixture in its unmodified form or optionally in combination with a (meth)acrylic acid (salt) monomer and a monomer copolymerizable with such monomers, preferably in its unmodified form, to the copolymerization. In this case, the polymerization method will be described in detail below. On other words, this method fits for the mass production and proves advantageous from the industrial point of view, because it can omit the step of isolating the alkoxy polyalkylene glycol mono(meth) acrylic acid in the production of the polycarboxylic acid copolymer.

In the embodiment as described above, the value calculated by the formula: $40 \leq [(p/n^{1/2})/q] \times 100$ (referred to occasionally as "K value") is a criterion for representing an average number of polyalkylene glycol chains per weight of the carboxylic acid. In this invention, the K value is preferred to be in the range of 42 to 190 ($42 \leq K$ value $\leq 190$), more preferably in the range of 45 to 160 ($45 \leq K$ value $\leq 160$). In this case, if the K value is less than 40, the cement dispersant consequently obtained would be deficient in cement-dispersing properties. Conversely, if the K value exceeds 200, the excess would be at a disadvantage in markedly increasing the reaction time of esterification and widely lowering the productivity, in addition to similarly degrading the cement-dispersing properties of the produced cement dispersant.

Further, the esterification reaction of this invention, when necessary, may be performed with an acid catalyst added to the reaction system. Since the acid catalyst is capable of promoting the reaction quickly, it is commendable to perform the reaction in the presence of the acid catalyst. As concrete examples of the acid catalyst which can be used herein, sulfuric acid, methane sulfonic acid, paratoluene sulfonic acid, paratoluene sulfonic acid hydrate, xylene sulfonic acid, xylene sulfonic acid hydrate, naphthalene sulfonic acid, naphthalene sulfonic acid hydrate, trifluoromethane sulfonic acid, "Nafion" resin, "Amberlyst 15" resin, phosphorus tungstic acid hydrate, and hydrochloric acid may be cited. These acid catalysts may be used either singly or in the form of a mixture of two or more members.

In these acid catalysts, the acid catalyst to be used may preferably have a high boiling point under normal pressure in consideration of the azeotropic temperature of the dehydrating solvent and water which will be described specifically herein below and the temperature of the esterification reaction. Typically, the boiling point under normal pressure of the acid catalyst which may be preferably used in this invention is preferably not less than 150° C., more preferably not less than 200° C. Thus, sulfuric acid (boiling point under normal pressure: 317° C.), paratoluene sulfonic acid (boiling point: 185 to 187° C./0.1 mmHg), paratoluene sulfonic acid hydrate, and methane sulfonic acid (boiling point: 167° C./10 mmHg) are preferably used over the rest of acid catalysts. The present inventors have acquired a knowledge that one of the causes for the formation of a diester, i.e., the impurity liable to degrade the quality and performance of the esterified product, is the cleavage of an alkoxy polyalkylene glycol and that the cleavage can be also caused by the acid catalyst. Based on this knowledge, they have found that the acid catalyst which is less liable to the cleavage can be desirably used. In consideration of the point mentioned above, paratoluene sulfonic acid and paratoluene sulfonic acid hydrate may be cited as the acid catalysts which can be particularly advantageously used in this invention.

In the mode described above, the amount of the acid catalyst to be used does not need to be particularly restricted so long as it fall in the range in which the catalytic action sought after can be effectively manifested. It is preferably not more than 0.4 millieqivalent/g, more preferably in the range of 0.36 to 0.01 milliequivalent/g, and particularly preferably in the range of 0.32 to 0.05 milliequivalent/g. If the amount of the acid catalyst to be used exceeds 0.4 milliequivalent/g, the amount of the diester to be formed in the reaction system during the esterification reaction would increase and the cement dispersant synthesized with the esterified product [alkoxy polyalkylene glycol mono(meth) acrylic acid] obtained by the esterification reaction would suffer degraded cement-dispersing properties. In this specification, the amount of the acid catalyst (milliequivalent/g) to be used is expressed by a numerical value obtained by dividing the number of equivalent weight (milliequivalent) of the $H^+$ of the acid catalyst used in the reaction by the total amount (g) of the alcohol and the (meth)acrylic acid as the raw materials. More specifically, it is the numerical value calculated by the following formula.

$$\text{Amount of acid catalyst used (milliequivalent/g)} = \frac{[\text{Equivalence (milliequivalent) of } H^+ \text{ of acid catalyst}]}{[(\text{Weight (g) of alcohol charged}) + (\text{Weight (g) of (meth) acrylic acid charged})]}$$

In this invention, the addition of the acid catalyst to the reaction system may be effected collectively, continuously, or successively. Preferably in terms of operational efficiency, the acid catalyst is added collectively together with the raw materials to the reaction tank.

Further, in this invention, when the esterification reaction is performed in the presence of the acid catalyst, the acid catalyst may be used in the form of hydrate and/or aqueous solution.

As concrete examples of the acid catalyst which can be used in the mode mentioned above, sulfuric acid, methane sulfonic acid, paratoluene sulfonic acid, xylene sulfonic acid, naphthalene sulfonic acid, trifluoromethane sulfonic acid, "Nafion" resin, "Amberlyst 15" resin, phosphorus tungustic acid, and hydrochloric acid which are invariably used in the form of a hydrate and/or an aqueous solution may be cited. Among other acid catalysts mentioned above, sulfuric acid, paratoluene sulfonic acid, and methane sulfonic acid in the form of a hydrate and/or an aqueous solution may be particularly advantageously used. These acid catalysts may be used either singly or in the form of a mixture of two or more members. Further, the present inventors, as described above, have acquired a knowledge that one of the causes for the formation of a diester, i.e., the impurity liable to degrade the quality and performance of the esterified product, is the cleavage of an alcohol and that the cleavage can be also caused by the acid catalyst and, on the basis of this knowledge, they have found that the acid catalyst which is less liable to the cleavage can be desirably used. Specifically, the acid catalyst that answers this description may be paratoluene sulfonic acid and which is used in the form of a hydrate and/or an aqueous solution.

The amount of the acid catalyst to be used in the mode described above does not need to be particularly restricted so long as the expected catalytic activity be effectively manifested. In consideration with the repression of the action of cleavage of the alcohol as a raw material, the availability of the esterified product as a raw material for a polymer component to be used in various applications including a cement dispersant, a pigment dispersant for calcium carbonate, carbon black, ink, and other pigments, and a scale remover, a dispersant for a slurry of gypsum and water, a dispersant for CWM, a thickener, and the prevention/ repression of the occurrence of gel as a cause for forming a high-molecular-weight cross-linked polymer of poor dispersing properties liable to exert adverse effects on the dispersing properties, i.e. the basic property required for such service application, however, the amount of the acid catalyst to be used is preferred to satisfy the following relation:

$$0 < Y < 1.81X - 1.62$$

wherein X (% by weight) represents the weight ratio of the acid in the acid catalyst to the total weight of the alcohol and the (meth)acrylic acid as raw materials and Y (% by weight) represents the weight ratio of the water present in the hydrate and/or the aqueous solution of the acid catalyst to the total weight of the alcohol and the (meth) acrylic acid as raw materials. To describe this requirement by citing a concrete example so as to avoid misunderstanding, in the case of paratoluene sulfonic acid monohydrate, for example, it should be noted that X (% by weight) represents the weight ratio of paratoluene sulfonic acid based on the total weight of the raw materials, and Y (% by weight) represents the weight ratio of the water present as the monohydrate based on the total amount of the raw materials, and that the acid component (such as (meth)acrylic acid as the raw material) and the water components (such as water formed by the esterification reaction) other than the acid catalyst can never constitute themselves X and Y which are referred to herein.

If the amount of the acid catalyst to be used does not satisfy the relation of the formula mentioned above, the following problems would ensue. To be specific, in the case of Y=0, since the acid catalyst does not allow the existence of water in the form of a hydrate and/or an aqueous solution therein, the amount of gel suffered to form in the reaction system during the course of the esterification reaction increases and this increase degrades performance such as cement-dispersing properties used in a cement dispersant synthesized with the esterified product obtained by the esterification reaction. On the other hand, in the case of $Y \geq 1.81X - 1.62$, the amount of gel suffered to form in the reaction system during the course of the esterification reaction also increases, which degrades performance such as cement-dispersing properties used in a cement dispersant synthesized with the esterified product obtained by the esterification reaction.

In the mode described above, the acid catalyst may be added to the reaction system collectively, continuously, or successively. In terms of operational efficiency, the acid catalyst may be preferably added collectively together with the raw materials to the reaction tank.

The esterification reaction according to this invention preferably proceeds in the presence of a polymerization inhibitor, because the use of the polymerization inhibitor can prevent the alcohol and the (meth)acrylic acid as the raw materials, the resultant esterified product, and the mixture thereof from being polymerized. The polymerization inhibitor, which can be used in the esterification reaction mentioned above, does not need to be particularly restricted but may be randomly selected from well-known polymerization inhibitors. As concrete examples thereof, phenothiazine, tri-p-nitrophenyl methyl, di-p-fluorophenyl amine, diphenyl picryl hydrazyl, N-(3-N-oxyanilino-1,3-dimethyl butylidene) aniline oxide, benzoquinone, hydroquinone, methoquinone, butyl catechol, nitroso benzene, picric acid, dithiobenzoyldisulfide, cupferron, and copper (II) chloride may be cited. On account of the solubility in a dehydrating solvent and reaction-forming water, phenothiazine, hydroquinone, and methoquinone are preferably used over the rest of polymerization inhibitors. These polymerization inhibitors may be used either singly or in the form of a mixture of two or more members.

When the acid catalyst is used in the form of a hydrate and/or an aqueous solution as described above, phenothiazine may be very useful in respect that it not only functions effectively on the gel-forming substance in the aqueous solution existing in the reaction system but also can manifest polymerization inhibiting ability very effectively and can effectively repress the formation of high-molecular-weight products during the expulsion of dehydrating solvent and water by azeotropic distillation after the completion of esterification reaction as will be described specifically herein below without recourse to such a water-soluble polymerization inhibitor as hydroquinone and methoquinone which exhibits a polymerizing activity, though only feebly.

According to the method of this invention, the amount of the polymerization inhibitor to be used is in the range of 0.001 to 1% by weight, preferably in the range of 0.001 to 0.1% by weight, based on the total amount of the alcohol and (meth)acrylic acid as the raw materials. If the amount of the polymerization inhibitor to be used is less than 0.001% by weight, the shortage would be at a disadvantage in manifesting polymerization-inhibiting ability insufficiently and encountering difficulty in effectively preventing the alcohol and the (meth)acrylic acid as the raw materials, the consequently formed esterified product, or the mixture thereof from being polymerized. On the other hand, if the amount of the polymerization inhibitor to be used exceeds 1% by weight, the excess would be at a disadvantage in impairing the quality and performance of the consequently formed esterified product owing to an increase in the amount of the polymerization inhibitor suffered to persist therein and imposing a burden on the economy of production without bringing any proportionate addition to the effect.

The esterification reaction according to this invention, for the reason offered herein below, must be carried out with a dehydrating solvent added. When the esterification reaction is carried out without using a dehydrating solvent, namely in the absence of a solvent, the reaction solution is subjected to bubbling treatment with air and the like for the purpose of removing therefrom reaction-forming water. Since the raw materials are directly heated from a heat source in the absence of a solvent, this heating probably induces cleavage of alcohol and gives rise to a diester and results in degradation of cement dispersing ability. The term "dehydrating solvent" as used herein is defined as a solvent capable of forming an azeotrope with water. By the use of the dehydrating solvent, water formed by the esterification reaction can be very efficiently removed by distillation from the reaction solution because it readily forms an azeotrope with this solvent. As concrete examples of the dehydrating solvent, benzene, toluene, xylene, cyclohexane, dioxane, pentane, hexane, heptane, chlorobenzene, and isopropyl ether may be cited. These dehydrating solvents may be used either singly or in the form of a mixture of two or more members. Among other dehydrating solvents mentioned above, those which have azeotropic temperatures with water of not more than 150° C., more preferably in the range of 60° to 90° C., may be used preferably. As concrete examples of the dehydrating solvent which answer this description, cyclohexane, toluene, dioxane, benzene, isopropyl ether, hexane, and heptane may be cited. If the azeotropic temperature of a given dehydrating solvent with water exceeds 150° C., this solvent would prove unfavorable in terms of handling (including such controls as the management of temperature in the reaction system during the course of reaction and the treatment of the azeotropic mixture for condensation and liquefaction).

Preferably, the dehydrating solvent effects expulsion of the reaction-forming water from the reaction system by forming an azeotropic mixture thereof and then refluxes itself through the reaction system while condensing and liquefying reaction-forming water and thereby separating and removing the consequently formed water condensate from the reaction system. In this case, the amount of the dehydrating solvent to be used is in the range of 1 to 100% by weight, preferably in the range of 2 to 50% by weight, based on the total amount of the alcohol and the (meth)acrylic acid as the raw materials to be charged. If the amount of the dehydrating solvent is less than 1% by weight, the shortage would be at a disadvantage in producing no fully satisfactory removal from the reaction system of reaction-forming water during the course of the esterification reaction and preventing the esterification reaction from proceeding smoothly. If the amount of the dehydrating solvent to be used exceeds 100% by weight, the excess would be at a disadvantage in producing no proportionate addition to the effect and requiring a great deal of heat for keeping the reaction temperature constant and consequently impairing the economy of the production.

In the esterification reaction according to this invention, it is commendable, in the case of using a dehydrating solvent, to set the reaction temperature at a level in the range of 300 to 140° C., preferably in the range of 60° to 130° C. and the solvent circulating speed at a level of not less than 0.5 cycle/hour, preferably in the range of 1 to 100 cycles/hour. These adjustments of the reaction temperature and the solvent circulating speed serve the purpose of obviating the necessity for heightening the reaction temperature to a region liable to form impurities (the region exceeding 130° C.) and repressing the formation of impurities in the reaction tank. By heightening the solvent circulating speed, it is made possible to avoid protracted stay of the reaction-forming water in the reaction tank, enable this water to be efficiently expelled by azeotropic distillation from the reaction tank, allow the equilibratory reaction to proceed in the direction of esterification, and consequently permit a decrease in the reaction time.

The expression "a solvent circulating speed during the esterification reaction" as used in this specification means as below. To be specific, "one cycle" is defined as a time required for circulating a distillate in an amount equal to a total amount (by volume) of a dehydrating solvent initially placed in the reaction system, when a dehydrating solvent is placed in the total amount (by volume), and the dehydrating solvent in the reaction tank is circulated through the route from the reaction tank via the circulating route back to the reaction tank. The solvent circulating speed during the esterification reaction is expressed by the number of such cycles per unit time (one hour) with the denomination of "cycle/hour". When the amount of the distillate circulated in five hours reaches 15 times the total amount of the dehydrating solvent initially placed in the reaction system, for example, the solvent circulating speed is calculated as 3 cycles/hour. By the same token, when the amount of the distillate thus circulated in two hours reaches one half of (0.5 times) the total amount of the dehydrating solvent initially placed in the reaction system, the solvent circulating speed is calculated as 0.25 cycle/hour. Incidentally the substances that are circulated at all while the dehydrating solvent in the reaction system is expelled from the reaction system by distillation, condensed and liquefied, and circulated back to the reaction system (substances to be circulated) may include, though in a minute amount, various additives such as raw materials with a low boiling point (mainly (meth) acrylic acid as a raw material) liable to be expelled from the reaction system by distillation and a antigelling agent (a polymerization inhibitor or a solvent containing the polymerization inhibitor) to be incorporated in the reaction system for the purpose of preventing the distilled raw material from forming gel and turning into harmful impurities. When such additives as an antigelling agent are used, therefore, it is commendable to adjust conditions of the esterification reaction properly in consideration of the possibility of these additives varying the solvent circulating speed with the advance of the esterification reaction.

The reaction temperature and the solvent circulating speed mentioned above can be adjusted in respectively proper requested ranges by the method (means) of heating the reaction tank, the temperature to which the reaction tank is heated (quantity of heat) by the use of the device, and the amount of the dehydrating solvent to be used relative to the raw materials placed in the reaction tank. Incidentally, the term "reaction temperature" as used herein means the highest (maximum) temperature in the reaction tank. Specifically, depending on designs of devices (such as, for example, an external jacket and an internal heater) to be used as heating means, the temperature (reaction temperature) in the reaction system (reaction tank) is scattered depending on positions in the reaction system, elevated with the advance of the esterification reaction, and varied with time. Since the elevation of the reaction temperature entails the formation of impurities, it is important that the reaction temperature be prevented from surpassing the upper limit defined above, without reference to the conditions of position and time and irrespectively of the choice of position and time. The present invention has elected to define this upper limit by the highest temperature mentioned above.

The reaction of esterification according to this invention may be performed without using a dehydrating solvent, namely in the absence of a solvent. In this case, for the purpose of removing the reaction-forming water from the reaction solution, a bubbling treatment using a gas such as air or an inert gas (nitrogen gas, helium gas, argon gas, or carbon dioxide) (preferably a gas containing no steam) must be performed on the reaction solution. As a typical example of the bubbling treatment, a method which comprises continuously blowing a gas (bubbles) out into the reaction solution through an air nozzle disposed in the lower part of the reaction tank, allowing the bubbles while rising through the reaction solution to take in the water in the reaction solution, and inducing expulsion by distillation from the reaction tank of the steam-containing gas which has passed through the reaction solution [preferably liquefying and removing the stream contained in the gaseous distillate (steam-containing gas) and again circulating the dried gas] may be cited. The bubbling treatment does not need to be limited to this method. Among various known methods which fit for the bubbling treatment, one or optionally more methods may be suitably selected and used. The flow volume of air necessary for the bubbling treatment, therefore, ought to be commensurate with the amount of the reaction-forming water arising successively in the reaction tank lest the reaction-forming water should stay for a long time within the reaction tank. It suffices to supply the air continuously to the reaction tank in the flow volume commensurate with the rate of formation of the water. The gas is preferably supplied as heated to a temperature equalling the temperature of the reaction solution lest the gas should vary the temperature within the reaction tank. In this embodiment, to liquefy the distillate (steam-containing gas) emanating from the reaction system with the condenser, it suffices to resort to the action of the antigelling agent solution.

Though the esterification reaction can proceed in batchwise or continuously, this invention prefers this reaction to be performed in batchwise.

The conditions for the esterification reaction have only to ensure smooth advance of this reaction. The reaction temperature, for example, is properly in the range of 30° to 140° C., preferably in the range of 600 to 130° C., more preferably in the range of 900 to 125° C., and particularly preferably in the range of 1000 to 120° C. The reaction temperature mentioned above applies to the general mode of the esterification reaction of this invention. It fits, for example, the case of expelling the dehydrating solvent from the reaction system in the form of an azeotropic mixture with the reaction-forming water, separating and removing the water by condensation and liquefaction, and meanwhile refluxing the residue of condensation. This case is embraced in the range contemplated by this invention, though not in perfect conformity. If the reaction temperature is lower than 30° C., the shortage would bring such disadvantages as rendering the advance of the esterification reaction difficult, requiring an unduly long time for the dehydration (expulsion by distillation) of the water formed by the reaction, retarding the reflux of the dehydrating solvent and suffering the dehydration to consume unduly long time and, as a result, consuming much time for the esterification reaction. Conversely, if the reaction temperature surpasses 140° C., the excess would be similarly at a disadvantage in entailing formation of diesters in an excessive amount in consequence of the cleavage of the alcohol as a raw material, degrading the dispersing properties of the cement dispersant and impairing dispersion properties and thickening properties in various applications found for the esterified product, entailing polymerization of raw materials, adding to the amount of the raw material suffered to mingle into the distillate, and deteriorating the esterified product in performance and quality. The reaction time, as described specifically herein below, has to be such that the ratio of esterification reaches at least 70%, preferably at least 80%. The time which answers this description is in the range of 1 to 50 hours, preferably 3 to 40 hours. Though the esterification reaction according to this invention is permitted to proceed under normal pressure or under a reduced pressure, it may preferably proceed under normal pressure from the viewpoint of equipment.

Properly, the ratio of esterification in the esterification reaction according to this invention is not less than 70%, preferably in the range of 70 to 99%, and more preferably in the range of 80 to 98%. If the ratio of esterification is less than 70%, the shortage would be at a disadvantage in forming the esterified product (alkoxy polyalkylene glycol mono(meth)acrylic acid) with an insufficient yield and compelling the cement dispersant made from this product as a raw material to suffer from poor cement-dispersing properties. The term "ratio of esterification" as used in this specification is a numerical value which is found by measuring the amount of alcohol, one of the starting materials for esterification, to be decreased under the following conditions for the measurement of esterification and calculating the following formula using the result of the measurement.

Esterification ratio (%) ={[(Area of alcohol charged)−(Area of alcohol at completion of esterification)]/[Area of alcohol charged]}×100

Condition for Measurement of Esterification

Analyzing device: Chromatography Manager made by Waters and sold under the trademark designation of "Millennium"

Detector: Detector made by Waters and sold under the product code of "410 RI"

Column used: Three columns made by GL Science and sold under the trademark designation of "Inatosil ODS-2"

Column temperature: 40° C.

Eluate: Prepared by mixing 8946 g of water, 6000 g of acetonitrile, and 54 g of acetic acid and adjusting the mixture with an aqueous 30% sodium hydroxide solution to pH 4.0

Flow rate: 0.6 ml/min

Since the ratio of esterification is determined by the formula described above, the ratio of esterification can never exceed 100%. In this invention, therefore, the time at which the ratio of esterification reaches a level above the prescribed level is reported as marking completion of the esterification reaction.

So far, the esterification reaction contemplated by this invention has been described. Now, the requirement for construction according to the first aspect of this invention will be described in detail below.

The term "distillate" as used in this specification means the substance (mixture) which is expelled by distillation from the reaction tank, and includes all substances which are expelled by distillation from the reaction tank, despite kinds of steps including those during the esterification reaction, a solvent-expelling step after the completion of the esterification reaction and etc. The distillate contemplated by this invention, therefore, is not particularly discriminated on account of the state of existence thereof. It may exist in a gaseous state or a liquid state, whichever better fits the occasion. To be more specific, the term "distillate" as used in this specification includes a distillate which contains water to be formed during the esterification reaction and expelled from the reaction tank by distillation, a raw material, particularly (meth)acrylic acid, to be distilled together with the water when the water is expelled by distillation from the reaction tank, and a dehydrating solvent which is optionally added to the reaction tank for the purpose of forming an azeotropic mixture with the water; and a distillate which contains a dehydrating solvent to be expelled by distillation from the reaction tank during the course of solvent-expelling step after the completion of the esterification reaction, and a raw material, particularly (meth)acrylic acid, to be expelled by distillation together with the dehydrating solvent when this solvent is expelled by distillation from the reaction tank, unless otherwise specified. The term "reaction tank" as used herein does not need to be discriminated on account of its name but ought to be interpreted in the broadest possible sense so as to embrace a reaction device, a reaction vessel, a reaction kettle etc. Though some of the expressions of this class may be suitably used hereinafter for the sake of description, this invention ought not to be limited to the contents of the senses of such individual expressions. By the same token, the term "condenser" and the term "water separator" to be used herein below do not need to be discriminated on account of their names but ought to be interpreted in the broadest possible senses.

The antigelling agent to be used in the method of production according to this invention for the purpose of exerting its action on the distillates such as water arising during the esterification reaction does not need to be particularly discriminated so long as it be capable of repressing the reaction of polymerization at the stage of expulsion by distillation of a low-boiling raw material arising in conjunction with the water, particularly at the stage of condensation and repressing the formation of gel as in the flange part of the pipe rising from the reaction tank to the condenser, namely the blockage of the tube of the condenser or the connecting tube between the reaction tank and the condenser. It may be suitably selected among various antigelling agents known to the art. As concrete examples of thereof, phenothiazine, tri-p-nitrophenyl methyl, di-p-fluorophenyl amine, diphenyl picryl hydrazyl, N-(3-N-oxyanilino-1,3-dimethyl butylidene) aniline oxide, benzoquinone; hydroquinone, methoquinone, butyl catechol, nitroso benzene, picric acid, dithiobenzoyl disulfide, cupferron, and copper (II) chloride may be cited. Among other antigelling agents mentioned above, phenothiazine, hydroquinone, and methoquinone may be used favorably on account of the solubility in a dehydrating solvent and reaction-forming water. These antigelling agents may be used either singly or in the form of a mixture of two or more members.

The amount of the antigelling agent to be added has only to match the amount of the raw material of a low boiling point to be distilled, depending on conditions of the esterification reaction, particularly the quantity of heat applied to the reaction system and the amount of the dehydrating solvent to be initially placed in the reaction system, namely may be such an amount as to enable a raw material of a low boiling point which is successively distilled from the time of starting distillation of the azeotropic mixture to the time of completing the esterification reaction to prevent the formation of gel constantly. By adding the antigelling agent in an amount in the range of 0.1 to 1000 ppm, preferably 1 to 500 ppm, based on the combined amounts of alcohol and (meth) acrylic acid to be initially placed in the reaction tank as the raw materials, the object mentioned above can be accomplished. If the amount of the antigelling agent to be added is less than 0.1 ppm based on the combined amounts of the raw materials initially placed, the shortage would possibly entail formation of a gel-like substance. This amount may well be called insufficient for the purpose of effectively manifesting polymerization inhibiting properties constantly on raw materials of low boiling points which are successively distilled from the time of starting distillation of azeotropic mixture to the time of completing the esterification reaction. If the amount of the antigelling agent conversely exceeds 1000 ppm based on the combined amounts of the raw materials initially placed, the excess would be at a disadvantage in being unduly large for effective manifestation of the gel formation preventing properties (polymerization inhibiting properties) and impairing the economy of production without bringing a proportionate addition to the effect. When the total amount of the antigelling agent intended to be used is placed all at once in the reaction system, the raw material of a low boiling point which is successively distilled from the time of starting distillation of the azeotropic mixture to the time of completing the esterification reaction cannot be effectively prevented from forming gel. It is commendable, therefore, to add the antigelling agent piecemeal in a fixed. amount successively (continuously) from the time of starting distillation of the azeotropic mixture to the time of completing the esterification reaction in response to the distillation of the azeotropic mixture until the amount finally reaches a total in the range mentioned above.

The manner for causing an antigelling agent to act as expected (including a mode of action and an acting region) does not need to be particularly restricted so long as this agent be enabled to act (by contact) effectively on raw materials of low boiling points (fluid substances) distilled from the reaction system. When the reaction-forming water is to be expelled by distillation from the reaction system, the antigelling agent is preferred to be capable of being distilled at the lowest permissible temperature from the viewpoint of handling. For this purpose, a method of initially charging the reaction system with a solvent capable of forming an azeotropic mixture with the reaction-forming. water (in the present specification, occasionally referred to simply as "dehydrating solvent") and causing the dehydrating solvent to be distilled in the form of an azeotropic mixture with the reaction-forming water (in the present specification, occasionally referred to briefly as "solvent-water azeotropic mixture") during the course of the reaction is generally practiced. In this respect, it is commendable to add a solution of an antigelling agent in a solvent similar in kind to the dehydrating solvent so that it may promptly act on the solvent-water azeotropic mixture containing a raw material of a low boiling point (namely it may, during the condensation (liquefaction) of the solvent-water azeotropic mixture containing low boiling raw materials, promptly contact with the liquefied product and attain intimate solution or dispersion in the dehydrating solvent containing raw materials of a low boiling points which are susceptible of gelation.

Now, preferred methods for acting an antigelling agent mentioned above will be described below with reference to respective modes of action. This invention allows proper combination of these methods and suitable adoption of the other acting methods well-known to the art. The acting methods illustrated herein below may be typical examples cited for the purpose of enabling persons of ordinary skill in the art to understand this invention easily. Naturally, this invention should not be limited to or by these examples.

1. Method for Acting the Agent in a Liquefied (dissolved) State:

A solution of an antigelling agent in a proper solvent, preferably a solvent similar in kind to the dehydrating solvent initially placed in the reaction system, may be added dropwise or sprayed to a region for condensing a distillate containing reaction-forming water (preferably, a solvent-water azeotropic mixture), specifically to an interior of a condenser for condensing and liquefying a distillate containing reaction-forming water, preferably from an upper part of a condenser (especially a column top) to the interior thereof in such a manner as to establish parallel contact with the distillate. It may be otherwise permissible, though depending on such factors as a type of condenser used, to place initially a solution containing an antigelling agent in a condenser and then blow a distillate in a gaseous state or cast a distillate in a liquefied state into the condenser so as to effect contact (intimate solution or dispersion) with the solution held therein. Further, although in the above embodiment, the acting site with an antigelling agent is described as an interior of a condenser for condensing and liquefying a distillate, there may be other positions prone to the occurrence of gel such as, for example, a joint part (flange part) between a reaction tank and a line for guiding a rising vapor, a flange part interposed between a vapor line and a top part of the column of the condenser, a thermometer provided on the reaction tank, and a projecting part formed around the inspection window, as well as the condensing part inside the condenser. Among other positions mentioned above, the condensing part inside the condenser (especially near the column top), the flange part between the reaction tank and the vapor rising line, and the flange part between the vapor line and the top part of the column of the condenser prove particularly advantageous to be the acting site with an antigelling agent. Further, the above acting site may be used or alternatively, a plurality of the above acting sites may be used simultaneously if necessary.

2. Method for Acting the Agent in a Solidified State:

An antigelling agent in a powdery state may be dropped or sprayed onto a region for condensing a distillate containing reaction-forming water, specifically to an interior of a condenser for condensing and liquefying a distillate containing reaction-forming water, preferably from an upper part of a condenser (especially a column top) to the interior thereof in such a manner as to establish parallel contact with the distillate. It may be otherwise permissible, though depending on such factors as a type of condenser, to have an antigelling agent in the form of particles of a fixed particle diameter placed in advance in the condenser and then exposed to the distillate for required contact. Further, although in the above embodiment, the acting site with an antigelling agent is described as an interior of a condenser for condensing and liquefying a distillate, there may be other positions prone to the occurrence of gel such as, for example, a joint part (flange part) between a reaction tank and a line for guiding a rising vapor, a flange part interposed between a vapor line and a top part of the column of the condenser, a thermometer provided on the reaction tank, and a projecting part formed around the inspection window, as well as the condensing part inside the condenser. Among other positions mentioned above, the condensing part inside the condenser (especially near the column top), the flange part between the reaction tank and the vapor rising line, and the flange part between the vapor line and the top part of the column of the condenser prove particularly advantageous to be the acting site with an antigelling agent. Further, the above acting site may be used or alternatively, a plurality of the above acting sites may be used simultaneously if necessary.

3. Method for Acting the Agent in a Gasified State:

An antigelling agent in a gasified state (including a sublimated state) and containing the reaction-forming water in a gasified state (containing a raw material of a low boiling point) may be supplied into and mixed in a pipe connecting between the reaction system and the condenser, e.g., such a position prone to the occurrence of gel as a condensing part inside the condenser (especially near the column top), a joint part (flange part) between a reaction tank and a line for guiding a rising vapor, a flange part interposed between a vapor line and a top part of the column of the condenser, a thermometer provided on the reaction tank, and a projecting part formed around the inspection window, preferably a condensing part inside the condenser (especially near the column top), a flange part between the reaction tank and the vapor rising line, and a flange part between the vapor line and the top part of the column of the condenser, prior to the condensation and liquefaction of a gaseous distillate containing reaction-forming water (including a raw material of a low boiling point).

Incidentally, in this invention, when the repression of the formation of gel at the flange part between the reaction tank and the vapor rising line is aimed at, this object may be attained by supplying the dehydrating solvent exclusively, i.e. without the antigelling agent incorporated therein, to this flange part. Concrete examples of the dehydrating solvent to be used in this case equal those of the dehydrating solvent already cited above. In the above embodiment, when the dehydrating solvent is used during the course of the esterification reaction, the dehydrating solvent of the same kind may be used or alternatively the dehydrating solvent of a different kind may be supplied to the flange part or alternatively the condensate (or the part thereof) may be used in a circulated state as will be described in detail herein below. When the esterification reaction is carried out in the absence of a dehydrating agent, it suffices to provide a separate dehydrating solvent-supplying mechanism preferably in the proximity of the flange part and supply the dehydrating solvent to the flange part.

Further, concerning the liquefaction of Item 1. mentioned above, when an antigelling agent is caused to manifest its action in a dissolved state, the solvents which can dissolve the antigelling agent mentioned above include benzene, toluene, xylene, cyclohexane, acetone, methylethyl ketone, n-hexane, and heptane, for example. It is commendable, however, to use a solvent similar in kind to the dehydrating solvent which is initially placed in the reaction system as mentioned above. When different solvents are used, they need to be separately recovered during the reflux back to the reaction system. Alternatively, when the heat transfer coefficient of the mixed solvents equals the heat transfer coefficient of the solvent initially placed in the reaction system, it becomes necessary to adjust the quantity of heat given to the reaction system lest the amount of the reaction-forming water to be distilled (speed of distillation) should vary widely, during the reflux back to the reaction system. In the case of different solvents used, their use possibly complicate the control and management of the reaction system. Thus, it is safe to conclude that the use of two solvents similar in kind is commendable.

Also when an antigelling agent is caused to function by being dissolved in a solvent (preferably a dehydrating solvent), for the purpose of repressing the occurrence of a gel-like substance, it suffices to supply an antigelling agent in such a manner to a raw material of a low boiling point (in a gaseous or liquid state) passing an interior of a condenser that it may exist constantly and function effectively in the raw material. The mixing ratio of the antigelling agent and the solvent does not need to be particularly restricted. Generally, the amount of the antigelling agent is in the range of 0.001 to 10 parts by weight, preferably 0.01 to 5 parts by weight, based on 100 parts by weight of the solvent. If the mixing ratio is such that the amount of the antigelling agent is less than 0.001 part by weight based on 100 parts by weight of the solvent, since the amount of the antigelling agent to be added is fixed relative to the total amount of the raw materials initially placed in the reaction system as defined above, the amount of the solvent to be used (the total amount to be added) would increase and the amount of the solvent relative to the amount of the dehydrating solvent initially placed would grow due to successive reflux. The control and management of the reaction system, therefore, is inevitably complicated because it becomes necessary to adjust the quantity of heat given to the reaction system and prevent the amount of the reaction-forming water to be distilled (speed of distillation) from varying widely. When a solvent to be used is not similar to the dehydrating solvent and these solvents are separately recovered, the cost of recovery would be increased and the cost of production is enlarged. Conversely, if the mixing ratio is such that the amount of the antigelling agent exceeds 10 parts by weight based on 100 parts by weight of the solvent, since the amount of the solvent to be used (the total amount to be added) is conversely decreased, the amount of the solvent added per unit time would be restricted, the frequency of contact of the antigelling agent with the raw material of a low boiling point would be relatively lowered, the raw material of a low boiling point would be liquefied without making the contact with the antigelling agent, and thus the effective repression of the formation of a gel-like substance will become difficult. For the purpose of securing the amount of the solvent required to be added per unit time, the cost of production is increased because the antigelling agent is required in an amount larger than the amount defined above relative to the initially placed raw materials.

By the method according to the first aspect as described above, the occurrence of the gel-like substance (such as poly(meth)acrylic acid) arising from (meth)acrylic acid, i.e. the raw material with a low boiling temperature to be expelled by distillation from the reaction system together with reaction-forming water while the reaction-forming water in the reaction system is expelled by distillation from the reaction system and then separated and removed by condensation and liquefaction, can be effectively prevented.

The method for producing the esterified product according to this invention will be described below with reference to FIG. 1.

FIG. 1 is a schematic diagram of the construction of a typical apparatus to be used for the method for producing the esterified product according to this invention.

As shown in FIG. 1, the construction of the apparatus according to the present embodiment is provided with a reaction tank 101 which is provided as a heating means for effecting the esterification reaction (such as, for example, a direct heating method resorting to an internal heater or an indirect heating method resorting to an external jacket) with an external jacket 102 using pressurized steam, for example, as a heating medium. In this case, the material for the internal part of the reaction tank is not particularly restricted but may be selected among conventional materials. The materials of SUS may be cited as examples, those of the species of SUS 304, SUS 316, and SUS 316L as examples preferable in terms of corrosion-proofness, and those of the species of SUS 316 and SUS 316L as more preferable examples. The reaction tank may be lined with glass so as to be inactivated relative to the raw materials and the product by esterification. To the reaction tank 101, a raw material storage tank 103 made of stainless steel (such as, for example, SUS 316) for alkoxy polyalkylene glycol as a raw material and a raw material storage tank 105 for (meth) acrylic acid, a catalyst storage tank 107 for an acid catalyst for reaction, a polymerization inhibitor storage tank 109 for storing a polymerization inhibitor for preventing the polymerization in the reaction system (reaction tank 101), and a neutralizer storage tank 111 made of carbon steel (such as, for example, high carbon steel) and used for storing a neutralizing agent (an aqueous solution of a neutralizing agent) intended for neutralizing the catalyst after the esterification reaction are connected respectively with pipes 113, 115, 117, 119, and 121. Since (meth)acrylic acid is easily polymerized and polymerized even in consequence of protracted storage or exposure to heat and, for example, a minute amount of a polymerization inhibitor (such as 0.1% hydroquinone) may be added. In addition, since it also becomes readily polymerizable through the phenomenon of crystallization, when it is preserved in the raw material storage tank 105, benzene may be added to prevent (meth) acrylic acid from crystallization. Alternatively, (meth) acrylic acid as a raw material may be circulated through a circulating path 151 while constantly retained at 30° to 40° C. so as not to be polymerized, by forming the path 151 provided with an external jacket 150 (insulating means) using a pump 116 as illustrated in FIG. 1 to keep the (meth)acrylic acid constantly at a temperature in the range of 30° to 40° C. The raw material storage tank 105 for (meth) acrylic acid, the pipe 115, the pump 116, and the circulating path 151 may be lined with such a corrosion-proofing material as a synthetic resin for the purpose of protection against the corrosion by (meth)acrylic acid which has a corroding property. Likewise, the catalyst storage tank 107 and the pipe 117 therefor may be lined with such an acid-resistant material as a synthetic resin for the purpose of protection against the corrosion by the acid catalyst. To the lower part of the reaction tank 101 mentioned above, a pipe 153 is connected for recovering the esterified product synthesized inside the reaction tank 101 by the esterification reaction (or, in the case of a cement dispersant, for example, the polymer obtained by further polymerizing the esterified product as a monomer component in the reaction tank 101). Inside the reaction tank 101, a plurality of temperature sensors (not shown) for measuring the reaction temperature may be mounted at as many proper sites. These temperature sensors may be electrically connected to a control part for controlling a mechanism required to maintain the reaction temperature at a prescribed level (for example, a temperature of the jacket 102 mounted on the reaction tank 101).

Further, in this embodiment, as a mechanism (an apparatus) for expelling by distillation a distillate containing reaction-forming water to be formed during the esterification reaction in a reaction system (a reaction tank 101), condensing and liquefying the distillate while preventing the occurrence of gel, separating and removing the reaction-forming water, and returning the rest of the distillate at a prescribed solvent circulating speed, a circulation system is provided therein for condensing and liquefying by the action of a antigelling agent a distillate occurring as an azeotropic mixture of reaction-forming water and a dehydrating solvent, separating and removing the reaction-forming water (water phase) from the condensed and liquefied distillate, and refluxing the rest of the condensate (a solvent phase mainly containing the dehydrating solvent) back to the reaction tank 101 at the solvent circulating speed mentioned above. To be more specific, the upper part of the reaction tank 101 and the top part of the column of a vertical shell and tube type condenser 125 of the counterflow (or parallel flow) contact type are connected with a pipe 123. The lower bottom part of the condenser 125 and the upper part of a water separator 127 made of SUS are connected with a pipe 129. Inside the water separator 127, a partition plate 131 is formed. The partition plate 131 divides the interior of the water separator 127 into two chambers 133 and 134. The lower part of the chamber 133 intended for storing the distillate condensed and liquefied in the condenser 125 and a treating tank 135 for the reaction-forming water are connected with a pipe 137. To the treating tank 135, a pipe 139 for waste water is connected. The lower part of the other chamber 134 of the water separator 127 and the reaction tank 101 are connected with a pipe 141. To this pipe 141, a pipe 145 which is connected to a dehydrating solvent storage tank 143 for storing a dehydrating solvent destined to form an azeotropic mixture with reaction-forming water in the reaction tank 101 is joined (connected). On a pipe 141 before this joining part (on the water separator 127 side), a circulating pump 142 is installed. A flow meter 144 is provided on the pipe 141 after the joining point (on the reaction tank 101 side). To the flow meter 144, a main body of a flow volume measuring system (not shown) is electrically connected for adding a flow volume and computing a solving circulating speed. A spray nozzle 126 is disposed on the top part of the column of the condenser 125 and this spray nozzle 126 is connected through the medium of a pipe 149 to a antigelling agent storage tank 147 for storing an antigelling agent intended to prevent a distillate from forming gel. Then, to the water separator 127, a vacuum pump (ejector) 155 intended to expel by distillation and remove the dehydrating solvent is attached through the medium of a pipe 157 for the purpose of isolating the esterified product after the esterification reaction.

This invention permits use of any of various known materials such as, for example, the materials of Class SUS including the species of SUS 304, SUS 316, and SUS 316L and carbon steel (CS) as well for the condenser. Preferably, for the purpose of repressing the occurrence of gel, a condenser to be used may have the inner wall thereof polished in mirror finish or lined with glass. In consideration of the cost to be required for fabrication and maintenance, the condenser may be preferably made of SUS 304 (equivalent to SUS 27 specified by Japanese Industrial Standard <JIS>; omitted herein below), SUS 316 (equivalent to SUS 32 specified by JIS; omitted herein below), or SUS 316L (equivalent to SUS 33 specified by JIS; omitted hereinafter), preferably SUS 316 or SUS 316L. Even by the use of the condenser of this kind, the formation of gel can be effectively prevented. The heat transfer surface area of the condenser which may be advantageously used in this invention, though variable with such factors as a volume of a reaction tank, is in the range of 50 to 500 $m^2$, preferably in the range of 100 to 200 $m^2$, in the case of a reaction tank having an inner volume of 30 $m^3$, for example. The cooling medium to be used in the condenser of this invention includes water or oil, for example.

The method for the production of the esterified product according to this invention is carried out as follows by using the apparatus constructed as described above.

First, alcohol and (meth)acrylic acid as raw materials, an acid catalyst, a polymerization inhibitor, and a dehydrating solvent are supplied (charged) from the raw material storage tanks 103 and 105, the catalyst storage tank 107, the polymerization inhibitor storage tank 109, and the dehydrating solvent storage tank 143 through the pipe 141 via the pipes 113, 115, 117, 119, and 145 into the reaction tank 101 respectively in the prescribed amounts and are subjected to esterification reaction under the conditions of esterification (reaction temperature, jacket temperature, and pressure) as specified above. The water successively formed by the esterification reaction forms an azeotropic mixture with the dehydrating solvent placed in the reaction tank 101 and expelled through the pipe 123 by distillation. The solvent-water azeotropic mixture in the form of a gas stream so distilled out is delivered to the condenser 125 and condensed and liquefied therein. For the purpose of preventing the raw material of a low boiling point contained in the azeotropic mixture from gelation during the condensation and liquefaction, the antigelling agent is continuously dropped in the amount specified above from the antigelling agent storage tank 147 via the pipe 149 into the condenser 125 through the spray nozzle 126 provided in the top part of the column thereof and brought into parallel contact with the azeotropic mixture (including both the gas stream and the condensed and liquefied product). The condensed and liquefied azeotropic mixture (including the antigelling agent introduced dropwise) is forwarded from the lower part of the condenser 125, passed through the pipe 129, and stored in the chamber 133 of the water separator 127 and separated therein into the two layers of water phase and solvent phase. The reaction-forming water in the lower layer part is successively extracted from the lower part of the chamber 133 through the pipe 137 and stored in the treating tank 135 for the reaction-forming water. Then, inside the treating tank 135, the reaction-forming water, when necessary, is treated chemically or biologically so as to satisfy the environmental criteria (waste water quality standard) and then released from the system via the pipe 139. Meanwhile, the solvent phase (including the antigelling agent introduced dropwise and the raw material of a low boiling point) of the upper layer part overflows the partition plate 131 and collects in the adjoining chamber 134. Then, the solvent phase is forwarded by the pump 142 from the lower part of the chamber 134 and refluxed back via the pipe 141 to the reaction tank 101 at the solvent circulating speed specified above.

In this invention, the site for installing the antigelling agent storage tank intended to supply the antigelling agent is not particularly restricted but is preferred to be a position at which the formation of gel is liable to occur. For example, in addition to the embodiment illustrated in FIG. 1, namely the embodiment in which the spray nozzle 126 for spraying the antigelling agent is provided in the top part of the column of the condenser 125, the embodiment in which the spray nozzle for spraying the antigelling agent is installed at one or more points on the pipe 123 intervening between the reaction tank 101 and the condenser 125 may be cited. In the latter embodiment, the site to be selected for installing the spray nozzle for spraying the antigelling agent on the pipe 123 may be the position prone to the occurrence of gel such as, for example, the condensing part inside the condenser (especially a column top), a joint part (flange part) between a reaction tank and a line for guiding a rising vapor, a flange part interposed between a vapor line and a top part of the column of the condenser, a thermometer provided on the reaction tank, or the projecting part formed around the inspection window. Among other positions mentioned above, the condensing part inside the condenser (especially a column top), the flange part between the reaction tank and the vapor rising line, and the flange part between the vapor line and the top part of the column of the condenser prove particularly advantageous.

After the completion of the esterification reaction (the time when the ratio of esterification reaches a level above the normality is reported as an end point), an aqueous solution of a neutralizing agent from the neutralizing agent storage tank 111 is added into the reaction tank 101 via the pipe 121 to neutralize the acid catalyst, expel the dehydrating solvent (plus excess (meth)acrylic acid) in the form of an azeotropic mixture with water under normal pressure, and isolate the esterified product as expected. The expulsion of the dehydrating solvent and the excess (meth)acrylic acid by distillation can be attained by using a part of the above mechanism (construction) for releasing the distillate containing water formed during the course of the esterification reaction inside the reaction system (the reaction tank 101), condensing and liquefying the released distillate while precluding the formation of a gel-like substance, then separating and removing the reaction-forming water, and refluxing the rest of the distillate. Incidentally, in this case, since the dehydrated solvent (containing the excess (meth)acrylic acid when the isolation is continuously carried out without entailing polymerization) must be removed from the system without being refluxed, this removal may be accomplished by using the vacuum pump (ejector) 155 which is mounted on the water separator 127. The resultant effluent may be either discarded or reused after the chemical treatment performed in a device separated from the system. Meanwhile, the esterified product obtained by isolation is recovered via the pipe 153. When this product is to be used for the synthesis of a cement dispersant, for example, the esterified product so obtained may be further polymerized as one of the monomer components in the reaction tank 101 to synthesize a polymer capable of serving as a main component of the cement dispersant. In this case, the unaltered (meth)acrylic acid remaining in consequence of excess addition may be preferably used in its unmodified form as another monomer component without being separated and removed.

The embodiment of the method of this invention for the production of the esterified product has been described with reference to FIG. 1. The method for the production of the esterified product according to this invention is not limited to this embodiment described above. It is not restricted at all in terms of procedure (means) and construction of apparatus so long as it comprises a step of acting an antigelling agent on a distillate. The process and the construction of apparatus to be adopted for the use in the present invention can be suitably selected among those known to the art.

The esterification reaction according to this invention has been described in detail above. After the esterification reaction mentioned above has been finished, the esterified product aimed at may be preferably obtained by neutralizing the whole of the acid catalyst which will be described specifically herein below either alone or in combination with part of the (meth)acrylic acid (partial neutralization step) and then expelling by distillation the dehydrating solvent in the form of an azeotropic mixture with water from the reaction solution which will be described specifically herein below (solvent-expelling step).

Now, the partial neutralization step according to this invention will be described below. When the esterification reaction is carried out in the presence of an acid catalyst in the esterification step mentioned above, it is commendable to perform a partial neutralization step to be described below. The present inventors have found that when water is added to produce an azeotrope at the step of expelling the dehydrating solvent after the esterification reaction or when adjusting water is added to produce the aqueous solution of the esterified product after the esterification reaction in order to perform the additional polymerization using the esterified product, the acid catalyst would cause hydrolysis and induce degradation of quality and performance of the esterified product, that the product by this hydrolysis (hereinafter occasionally referred to simply as "hydrolyzate") remains in the esterified product, and when used for synthesizing a polymer for the production of varying kinds of dispersants including a cement dispersant and thickeners, constitutes itself an extraneous substance which refuses participation in the polymerization, results in lowering the ratio of polymerization (and consequently the productivity), and leads to degradation of the quality and performance of the polymer, and that for solving this problem, it is commendable to neutralize the acid catalyst with an alkali at a temperature of not higher than 90° C. after the completion of the esterification reaction as mentioned above. This neutralization step permits the formation of the esterified product of high purity and high quality without producing hydrolyzate.

Here, a preferred embodiment of the partial neutralization step will be described below.

In the partial neutralization step according to this invention, the acid catalyst may be neutralized with an alkali at a temperature of not higher than 90° C., preferably a temperature in the range of 50° to 0° C., after completion of the esterification reaction.

If the neutralizing temperature (the liquid temperature of the reaction system) in the partial neutralization step mentioned above exceeds 90° C., the excess would bring such a disadvantage as that the added alkali functions as a catalyst for hydrolysis and eventually produces a large amount of a hydrolyzate. Further, if the temperature is not higher than 50° C., the alkali would not function as a catalyst for hydrolysis and the occurrence of a hydrolyzate would be repressed perfectly. Furthermore, if the temperature is lower than 0° C., the shortage would bring the disadvantage that the reaction solution produced by esterification become viscous, the stirring would not be easily carried out during the neutralization, the decrease of the temperature to a prescribed level after the esterification reaction would consume an unduly long time, and the decrease of temperature to a level below room temperature would require installation of extra cooling means (device) and entail an addition to the cost of production.

The alkali (neutralizing agent) which can be used in the partial neutralization step does not need to be particularly discriminated. It suffices to use a substance which assumes a form of a hydroxide, $M(OH)_n$, dissolves in water, and exhibits basically, wherein M represents an alkali metal, an alkaline earth metal, or an ammonium group. Further, the carbonates and phosphate of alkali metals, ammonia, and amines may be embraced in the term "alkali". As concrete examples of the alkali, hydroxides of alkali metals such as sodium hydroxide and potassium hydroxide, hydroxides of alkaline earth metals such as magnesium hydroxide and calcium hydroxide, ammonia, and amines may be cited. Among other alkalis mentioned above, hydroxides, carbonates, and phosphates of alkali metals and alkaline earth metals may prove particularly advantageous for the reason that they can avoid emitting offensive odor when they are incorporated in cement. This invention permits these alkalis to be used either singly or in the form of a mixture of two or more members used at a proper ratio.

The acid to be neutralized by the use of the alkali mentioned above is an acid catalyst, preferably an acid catalyst in its entirety and a part of (meth)acrylic acid. The amount of the (meth) acrylic acid to be neutralized herein may be not more than 10% by weight, preferably in the range of 0.01 to 5% by weight, based on the amount of the (meth)acrylic acid to be used in the esterification reaction. The amount of the alkali (neutralizing agent) to be added, therefore, is in the range of 1.0 to 100 equivalence, preferably 1.0 to 10 equivalence, and more preferably in the range of 1.01 to 2 equivalence, per equivalence of the acid catalyst. The reason for designating the acid catalyst as the acid to be neutralized is that since the acid catalyst reacts strongly with the water to be added after the esterification reaction and produces a hydrolyzate, the acid catalyst is required to be inactivated. Though the (meth)acrylic acid can exist besides the acid catalyst as the acid component, there are no problems in the neutralization step because the acid catalyst has greater acid strength and thus is neutralized earlier than the (meth)acrylic acid. The initial object of the partial neutralization step can be accomplished so long as the acid catalyst be neutralized. Owing to the difference of the kind (the difference in acid strength) of the acid catalyst to be actually used or in the case of the treatment of the acid in a large amount on a commercial scale, however, there is a possibility that a part of the (meth)acrylic acid be neutralized before the acid catalyst is neutralized wholly. It is permissible from the standpoint of eliminating this possibility to neutralize the whole amount of the acid catalyst and a part of the (meth)acrylic acid. The fact that the amount of the (meth)acrylic acid to be neutralized exceeds 10% by weight of the amount of the (meth)acrylic acid used in the esterification reaction is not commendable because the polymerization velocity of (meth)acrylate is probably lower than that of (meth)acrylic acid and, and as a result, the resultant esterified product suffers from an unduly low rate of polymerization. If the amount of the alkali (neutralizing agent) to be added is less than 1.0 equivalence per equivalence of the acid catalyst, the shortage would bring a disadvantage that the acid catalyst cannot be completely neutralized and the hydrolyzate is copiously inevitably. Conversely, if the amount of the alkali (neutralizing agent) to be added exceeds 100 equivalences per equivalence of the acid catalyst, the excess would likewise bring a disadvantage that (meth) acrylic acid is neutralized in an unduly large amount and, consequently, the resultant esterified product is inevitably polymerized at an unduly low rate.

Incidentally, the alkali to be added does not need to be particularly discriminated on account of its form. It may well be safely concluded that the addition of the alkali in the form of an aqueous solution is commendable from the viewpoint of preventing the esterified product from hydrolysis.

Especially, when the esterification reaction is carried out in a dehydrating solvent, the addition of a large amount of water in combination with an alkali to the reaction system is advantageous for the purpose of preventing the esterified product from hydrolysis. In the reaction system containing no large amount of water, an alkali, owning to its sparing solubility in a dehydrating solvent, floats in a concentrated state in the system and this float of the highly concentrated alkali persists for a long time until the alkali is finished to be neutralized, which induces the esterified product may be is varied with the manner of use of the alkali. When an aqueous 40 to 60% alkali solution is added as a neutralizing agent, for example, water may be added in an amount generally in the range of 5 to 1000 parts by weight, preferably in the amount of 10 to 100 parts by weight, based on one part by weight of the aqueous alkali solution, which amount does not contain the amount for the aqueous alkali solution. If the amount of water added is less than 5 parts by weight, the shortage would bring a disadvantage that the alkali is distributed unevenly within the reaction system and the highly concentrated alkali induces the esterified product to be hydrolyzed. If the amount exceeds 1000 parts by weight, the excess would bring a disadvantage that provision of a separate neutralizing column is required for the purpose of securing productivity of the operation and consequently suffered to entail an addition to the cost of production.

Now, the solvent-expelling step according to this invention will be described below. Specifically, since the esterification reaction is performed in a dehydrating solvent, the reaction solution resulting from the esterification reaction mentioned above is necessary to be distilled to expel the dehydrating solvent by evaporation. When the esterification reaction is performed in the presence of an acid catalyst, after the esterification step mentioned above, the resultant reaction solution is subjected to the partial neutralization step mentioned above to neutralize the acid catalyst and a part of the (meth)acrylic acid and subsequently distilled to expel the dehydrating solvent by evaporation.

Now, a preferred embodiment of the solvent-expelling step will be described below.

The present inventors have found that when a water-soluble polymerization inhibitor is added to the reaction solution in an amount of not more than 1000 ppm, preferably not more than 500 rpm, and more preferably not more than 300 ppm, and particularly preferably 0 ppm, based on the total amount of alcohol and (meth)acrylate as raw materials during the course of the expulsion by distillation of the dehydrating solvent from the reaction solution at the solvent-expelling step after the completion of the esterification reaction (optionally followed by the partial neutralization step), the water-soluble polymerization inhibitor which is added primarily for the purpose of inhibiting polymerization would quite unexpectedly induce polymerization of the unaltered raw materials, the esterified product, or the mixture thereof and give rise to a high-molecular weight substance because this polymerization inhibitor possesses polymerizing activity, through feebly, that the polymerization inhibitor added during the course of the esterification reaction can function effectively also during the course of the expulsion of the dehydrating agent by distillation, and that the occurrence of high-molecular weight substance can be prevented without using a water-soluble polymerization inhibitor at all. If the amount of the water-soluble polymerization inhibitor to be used exceeds 1000 ppm based on the total amount of alcohol and (meth) acrylic acid as raw materials, therefore, the polymerizing activity which is possessed by the water-soluble polymerizing inhibitor would induce occurrence of such a high-molecular weight substance as mentioned above. When the esterified product containing the high-molecular weight substance is utilized as a monomer component, the cement dispersant using the resultant polymer is at a disadvantage in being adversely affected by the high-molecular weight substance.

For the solvent-expelling step, since the esterification reaction is carried out in the presence of a polymerization inhibitor, when this polymerization inhibitor happens to be capable of functioning effectively after the esterification reaction (and also after the partial neutralization step) as mentioned above, the solution which is used during the solvent-expelling step does not need to be additionally supplemented with a polymerization inhibitor. When the partial neutralization is performed using an aqueous solution of alkali of low concentration, water is present in a comparatively large amount in the reaction solution. Exclusively when a polymerization inhibitor which has been used during the course of the esterification reaction is sparingly soluble or insoluble in water and does not function very effectively after the esterification reaction (and also after the partial neutralization), for example, since the unaltered raw materials and esterified product possibly dissolve in water and polymerize, it is commendable to add a water-soluble polymerization inhibitor in an amount in such a range as to manifest the polymerization-inhibiting ability more effectively than the polymerizing activity (the range specified above), in view of preventing the unaltered raw materials and esterified product possibly dissolve in water from polymerization and in view of the relation between the function of polymerization due to the polymerizing activity possessed by the water-soluble polymerization inhibitor and the polymerization inhibiting ability inherent therein, and then to heat the reaction solution to a temperature to be specified herein below to expel by distillation therefrom the dehydrating solvent in the form of an azeotropic mixture with water.

The water-soluble polymerization inhibitor which can be used herein is not particularly restricted. As concrete examples thereof, hydroquinone, methoquinone, catechol and the derivatives thereof (such as, for example, p-t-butyl catechol), and hydroquinone monomethyl ether may be cited. Among other examples cited above, hydroquinone and methoquinone are commendable because of comparative low polymerizing activity. These water-soluble polymerization inhibitors may be used either singly or in the form of a mixture of two or more members.

According to the second aspect, this invention is to provide a method for the production of an esterified product by the esterification reaction of an alcohol represented by the formula (1):

$$R^1O(R^2O)_nH \quad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$ may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid in a dehydrating solvent, wherein said method comprises performing the esterification reaction meanwhile expelling by distillation water formed during the esterification reaction in conjunction with the dehydrating solvent, condensing and liquefying the distillate containing the water, separating and removing the water from the condensate resulting from the condensation and liquefaction, and returning to the reaction tank the residue of condensate containing the dehydrating solvent remaining after the separation and removal of the water, and causing an antigelling agent solution containing a part of the residue of the condensate and an antigelling agent to act on the distillate during the course of the esterification reaction. The aspect described above is allowed to embrace the mode of causing the antigelling agent according to the first aspect to act on the distillate emanating from the esterification reaction, namely the mode of causing an antigelling agent to act on the distillate which results from expelling by distillation water formed during the esterification reaction in conjunction with the dehydrating solvent.

In the aspect described above, the terms "alcohol" and "(meth)acrylic acid" have the same definitions as contemplated in the first aspect described previously and the term "esterification reaction" also has the same definition as contemplated in the first aspect mentioned above excepting that the reaction must be performed in the presence of a dehydrating solvent.

Further, since water formed during the esterification reaction is required to be expelled from the reaction tank by distillation according to the above aspect, the term "distillate" to be used in this aspect generally contains the water as described above and additionally contains the raw material, particularly (meth)acrylic acid, which is distilled in combination with the water when this water is expelled by distillation from the reaction tank, and further the dehydrating solvent which is optionally added to the reaction tank for the purpose of forming an azeotropic mixture with the water.

The antigelling agent solution solution to be used in the method for the production of the present invention is referred to a solution intended to act on the distillate, more specifically a solution intended to act for the purpose of preventing a raw material with a low boiling point in the distillate from gelation. This solution contains a part of the condensate and the antigelling agent. Though the antigelling agent involved in this case may be used in its unmodified form or in the form of a solution, it more preferably contains a part of the residue of condensate and the antigelling agent in the form of a solution.

The term "condensate" as used in this specification means a liquid which emanates from the outlet of the condenser. This invention permits the antigelling agent solution to act on the distillate such as the reaction-forming water which arises during the esterification reaction. In such a case, the antigelling agent solution is embraced in the condensate. Since the condensate is subsequently divided by a water separator into the residue of condensate and the separated water, the residue of condensate and the separated water are both embraced in the definition of the term "condensate". They can be used independently of each other.

The term "a part of a condensate" as used in the present specification embraces a residue of condensate obtained by separating the condensate mentioned above and a part of the residue of condensate, in addition to such a condensate as that is merely partially separated.

The term "a residue of condensate" means a component in a solvent phase to be divided by a water separator and the term "separated water" means a component in an aqueous phase to be divided by the water separator as means for water separation. The component in the solvent phase contains the dehydrating solvent which is optionally used in addition to the antigelling agent solution. The component in the aqueous phase comprises the reaction-forming water and the raw materials. The condenser and the water separator mentioned above, in the method of production of an esterified product according to this invention, may be used as follows. Although the method for the production of an esterified product of this invention requires to expel the water formed during the esterification reaction from the reaction tank by distillation, the distillate also contains other components than the reaction-forming water as described above and, therefore, cannot be directly released into air for fear of the problem of air pollution. The reaction-forming water, therefore, must be properly treated or rendered reclaimable, after expelled from the reaction tank by distillation. Thus, the distillate emanating from the reaction tank may be forwarded to the condenser, and then condensed and liquefied therein. The condensate subsequently emanating from the outlet of the condenser may be further delivered to the water separator and, by utilizing the difference in nature, divided into two layers therein, i.e. the separated water formed of the component(s) in one aqueous layer and the residue of condensate formed of the component(s) in the another solvent layer.

The antigelling agent solution may contain an antigelling agent (including a form of solution; applicable similarly herein below) and other additives such as an acid catalyst suitably supplemented into the reaction tank, in addition to a part of the condensate mentioned above.

It is commendable that the antigelling agent be dissolved (or mixed such as when a part of the antigelling agent is contained undissolved in a supersaturated state, when the antigelling agents of two or more species are used, when a part of the antigelling agent is contained undissolved in the solvent, or when the antigelling agent is additionally mixed) in a proper solvent, preferably in a solvent similar in kind to the dehydrating solvent.

The antigelling agent to be used in this invention does not need to be particularly discriminated but is only required to be capable of repressing the polymerization reaction which occurs at the stage at which a raw material with a low boiling point expelled by distillation in conjunction with the reaction-forming water is condensed. It can be suitable selected among various antigelling agents known to the art. As concrete examples of thereof, phenothiazine, tri-p-nitrophenyl methyl, di-p-fluorophenyl amine, diphenyl picryl hydrazyl, N-(3-N-oxyanilino-1,3-dimethyl butylidene) aniline oxide, benzoquinone, hydroquinone, methoquinone, butyl catechol, nitroso benzene, picric acid, dithiobenzoyl disulfide, cupferron, and copper (II) chloride may be cited. Among other antigelling agents mentioned above, phenothiazine, hydroquinone, and methoquinone may be used favorably on account of the solubility in a dehydrating solvent and water formed by the reaction. These antigelling agents may be used either singly or in the form of a mixture of two or more members.

The amount of the antigelling agent to be used is required to be such that a raw material with a low boiling point which is successively expelled by distillation from the time the emanation of the distillate is started till the time the esterification reaction is completed can be constantly prevented effectively from forming gel (a cumulative amount from the time the emanation of the distillate is started till the time the esterification reaction is completed). Further, when a dehydrating solvent is used for the esterification reaction and this dehydrating solvent is expelled by distillation and refluxed, the antigelling agent, after fulfilling the purpose of preventing the distillate from polymerization, may be returned to the reaction tank in a state dissolved in the residue of condensate remaining after the separation and removal of the reaction-forming water, and successively accumulated in the reaction tank. As a result, when a varying end product such as a cement dispersant is to be produced by polymerizing the esterified product resulting from the reaction as a raw material, the accumulated antigelling agent renders this polymerization difficult. The amount of the antigelling agent to be used, therefore, is preferred to be repressed to the fullest possible extent. From the viewpoint mentioned above, the amount of the antigelling agent is in the range of 0.1 to 1000 ppm by weight, preferably in the range of 1 to 500 ppm by weight, based on the total amount of the raw materials, i.e. alcohol and (meth)acrylic acid, to be used. If the amount of the antigelling agent to be used is less than 0.1 ppm by weight, based on the total amount of the raw materials to be used, there would be a possibility that the reaction induces the occurrence of a gel-like substance because this amount is not sufficient for effectively manifesting constantly the polymerization inhibiting ability on a raw material having a low boiling point and to be successively expelled by distillation from the time the emanation of the distillate containing the reaction-forming water is started till the time the esterification reaction is completed. Conversely, if the amount exceeds 1000 ppm by weight based on the total amount of the raw materials, this amount would be far more than sufficient for effectively manifesting the polymerization inhibiting ability and this excess cannot be expected to make a proportionate addition to the manifestation of effect and is simply wasted economically and, when a varying end product such as a cement dispersant is to be produced by polymerizing the esterified product as a raw material, would render this polymerization difficult. Incidentally, when the antigelling agent is added in a whole amount at once, the added antigelling agent would encounter difficulty in effectively preventing a raw material with a low boiling point and successively emanating between the time the expulsion by distillation of the distillate containing the reaction-forming water is started and the time the esterification reaction is completed from forming a gel-like substance. It is, therefore, commendable to add continuously the antigelling agent up to a cumulative amount falling in the range specified above. In this case, it is more preferable to adjust and continue this addition in such a manner as that the concentration of the antigelling agent in the antigelling agent solution may constantly fall in the range specified herein below relative to the low boiling raw material successively expelled by distillation.

The solvent which can be used when the gel preventing agent is used in the form of a solution does not need to be discriminated particularly. As concrete examples of the solvent, benzene, toluene, xylene, cyclohexane, acetone, methylethyl ketone, n-hexane, heptane etc. may be cited. When the dehydrating solvent is used in the esterification reaction and this dehydrating solvent is expelled by distillation and refluxed, since the solvent component used in the antigelling agent solution is also returned to the reaction tank as contained in the condensate residue. The solvent component, therefore, is preferred to be capable of effectively acting as a dehydrating solvent in the reaction tank for esterification. Particularly, when a solvent to be used is different from the dehydrating solvent initially placed in the reaction tank, it is more preferable to use a solvent which is similar in kind to the dehydrating solvent initially placed in the reaction tank, in order to avoid such a trouble as that the quantity of heat applied to the interior of the reaction tank requires to be controlled and managed, the equipment inevitably expands due to the increase in the number of raw materials and the safety quality control and the inventory control gain in complication and complexity, because the azeotrpopic point between the dehydrating solvent containing the solvent and the reaction-forming water (and consequently the velocity of distillation) varies with the gradual increase of the amount (concentration) of the solvent in the reaction tank.

A main object of using the solvent in this aspect consists in liquefying the antigelling agent, facilitating the mixture of the antigelling agent with a part of the condensate, and obviating the necessity for installing a stirring device (such as a stirrer) for the sake of mixing the solvent with a part of the condensate. For the purpose of repressing to the fullest possible extent the growth of the amount of the residue of condensate to be returned into the reaction tank when the dehydrating solvent used for the esterification reaction is expelled by distillation and refluxed, the mixing ratio of the part of the condensate (preferably the residue of condensate) to be used in the antigelling agent solution is preferred to be as high as permissible. It is, therefore, commendable to repress the amount of the solvent to be used herein to the fullest possible extent. From this point of view, the concentration of the antigelling agent in the solution mentioned above may be in the range of 10 ppm by weight to a saturated concentration, preferably 100 ppm by weight to a saturated concentration, more preferably 200 ppm by weight to a saturated concentration, and particularly preferably 200 ppm by weight to a concentration equivalent to 95% of saturated concentration, based on the total amount of the solution. In this case, it should be noted that no specific value of the saturated concentration be specified because the saturated concentration is variable with the kinds of antigelling agent and solvent, the temperature, and the pressure and cannot be uniquely fixed. The amount of the solvent to be used can be decreased as much as permissible by using the saturated solution. Further, for the purpose of fixing the concentration of the antigelling agent to be fallen from the condenser, the concentration slightly lower than the saturated concentration which is varied by temperature may prove more favorable than the saturated concentration. It is, therefore, commendable to use the antigelling agent in a concentration of not higher than the level equivalent to 95% of the saturated concentration. If the concentration of the antigelling agent mentioned above is less than 10 ppm by weight based on the total amount of the solution, the shortage would bring a disadvantage that the mixing ratio of the part of the condensate used in the antigelling agent solution decreases and, when the dehydrating solvent is used in the esterification reaction and then expelled by distillation and refluxed, the amount of the residue of condensate returned to the reaction tank unduly increases. The elimination of this trouble would require provision of a large preserving part capable of preserving the gradually increasing residue of condensate till the esterification reaction is completed and a device means for releasing the part of the residue of condensate out of the system with the elapse of time. Further, the amount of the solvent to be used grows and the cost of production would increase.

As regards the flow volumes (rates) of the antigelling agent and the part of condensate to be used in the antigelling agent solution, they cannot be uniquely specified because they vary with the concentration of the antigelling agent in the antigelling agent solution, the size of the reaction apparatus (reaction tank, piping, and condenser), and the amount of the distillate. The antigelling agent solution is enabled to act in an ample amount on the distillate by decreasing the amount of the antigelling agent and using the condensate in a fully sufficient amount instead. Further, when a dehydrating solvent is used in the esterification reaction, and expelled by distillation and refluxed, the flow volumes may be suitably decided or defined depending on the mode of use so as to repress the increase of the amount of the solvent in the reaction tank to the fullest possible extent. Typically, the flow volume of the antigelling agent per minute per meter of the diameter (inside diameter) of the condenser may be in the range of 0.01 to 40 liters/minute·m, preferably in the range of 0.1 to 15 liters/minute·m, and more preferably in the range of 0.1 to 5 liters/minute·m. The flow volume of a part of the condensate per minute per meter of the diameter (inside diameter) of the condenser is in the range of 1 to 1000 liters/minute·m, preferably in the range of 5 to 500 liters/minute·m, and more preferably in the range of 10 to 200 liters/minute·m. If the flow volume of the antigelling agent is less than 0.01 liter/minute·m, the shortage would bring a disadvantage that the concentration of the antigelling agent in the solution decreases and the constant sufficient manifestation of the polymerization inhibiting ability is obtained with difficulty. Conversely, if the flow volume of the antigelling agent exceeds 30 liters/minute·m, the excess would bring a disadvantage that the amount of the solvent to be added increases and, as a result, the object of this invention which consists in decreasing the amount of the antigelling agent and using the condensate in a fully sufficient amount instead is accomplished with difficulty. If the flow volume of a part of the condensate is less than 1 liter/minute·m, such a shortage would bring a disadvantage that the condensate cannot be constantly supplied in a fully sufficient amount to the distillate and a possibility of inducing the occurrence of a gel-like substance becomes undeniable. Conversely, if the flow volume of part of the condensate liquid exceeds 1000 liters/minute·m, the excess would bring a disadvantage that no proportionate increase is given to the effect to be expected, provision of a device for supplying the condensate in such a large amount at a high flow volume (a pump of a large size or a pressure pipe of a large diameter) becomes necessary, and the operation proves uneconomical.

When the flow volume of the antigelling agent is decided (defined) and the flow volume of a part of the condensate, preferably a part of the residue of the condensate is decided (defined) in conformity with a mode of use as described above, all the combinations of these flow volumes may be made to fall within the specified range of flow volume. For fully manifesting the object of this invention, it may suffice to adopt the following combination for the mixing ratio of the antigelling agent solution to be used for the antigelling agent with a part of the condensate.

The amount of a part of the condensate is in the range of 0.5 to 10000 parts by weight, preferably in the range of 1 to 1000 parts by weight, more preferably in the range of 10 to 1000 parts by weight, and particularly preferably in the range of 10 to 100 parts by weight, based on 1 part by weight of the antigelling agent. If the amount of part of the condensate is less than 0.5 weight part, based on 1 part by weight of the antigelling agent, the shortage would bring a disadvantage that the object of this invention mentioned above can not be fully satisfied. Conversely, if the amount of a part of the condensate liquid exceeds 10000 parts by weight, based on 1 part by weight of the antigelling agent, the excess would bring a disadvantage that these two components are stably mixed with difficulty. The mixing ratio may be fixed or varied. The mixing ratio may be suitably decided so as to attain the object of this invention mentioned above.

In this invention, the method for making the antigelling agent act as expected does not need to be particularly discriminated but may be suitably selected among various methods (means) known to the art. Preferably, the antigelling agent solution may effectively function in the region for condensing and liquefying the gaseous distillate, specifically the heat exchanger, the cooling device, or the condenser (which will be collectively referred to simply as "condenser" in this specification) which constitutes itself the region for condensing and liquefying the gaseous distillate, and particularly the gas inlet site at the top of the condenser column at which the gaseous distillate begins to be condensed and liquefied. Thus, the region of the presence of the antigelling agent solution does not need to be limited to the interior of the condenser. The antigelling agent solution has only to act in the proximity of the top of the condenser column, namely the top of the condenser column or the interior of the path for distillation immediately preceding the condenser. It may well be concluded as commendable to keep the inner wall of the condenser constantly in a wet state by effecting as described above. Typically, (1) a method for keeping the inner wall of a condenser constantly in a wet state by causing the antigelling agent solution to be sprayed, blown out, blasted, discharged, blown up, or blown down through a nozzle part disposed upwardly at the central part of the top of the condenser column to the inner wall of the gas inlet part at the top of the condenser column (because at this inner wall, the initial condensation and liquefaction occurs and the gelation with a low boiling raw material simultaneously occurs) or (2) a method for keeping the inner wall of the condenser constantly in a wet state by causing the antigelling agent solution to be sprayed (or blown out) through a nozzle part (see FIG. 3) disposed in the path for distillation immediately preceding the condenser (a path formed of a pipe 503 shown in FIG. 2 which will be specifically described herein below; occasionally referred to as "an overhead line") and then allowed to trickle down the wall of the overhead line and reach the interior of the condenser may be cited, though not exclusively. Further, when a dehydrating solvent is used in the esterification reaction and then expelled by distillation and refluxed, the antigelling agent is preferably used in a form dissolved in a solvent similar in kind to the dehydrating solvent so that it may promptly contact the liquefied product resulting from the condensation and liquefaction of the distillate and intimately dissolve or disperse in the dehydrating solvent containing the low boiling raw material prone to gelation.

A method for refluxing a part of the condensate for the purpose of using it in the antigelling agent solution does not need to be particularly discriminated but may be suitably selected among various methods (means) known to the art. Concrete examples are as following.

Figure 2:
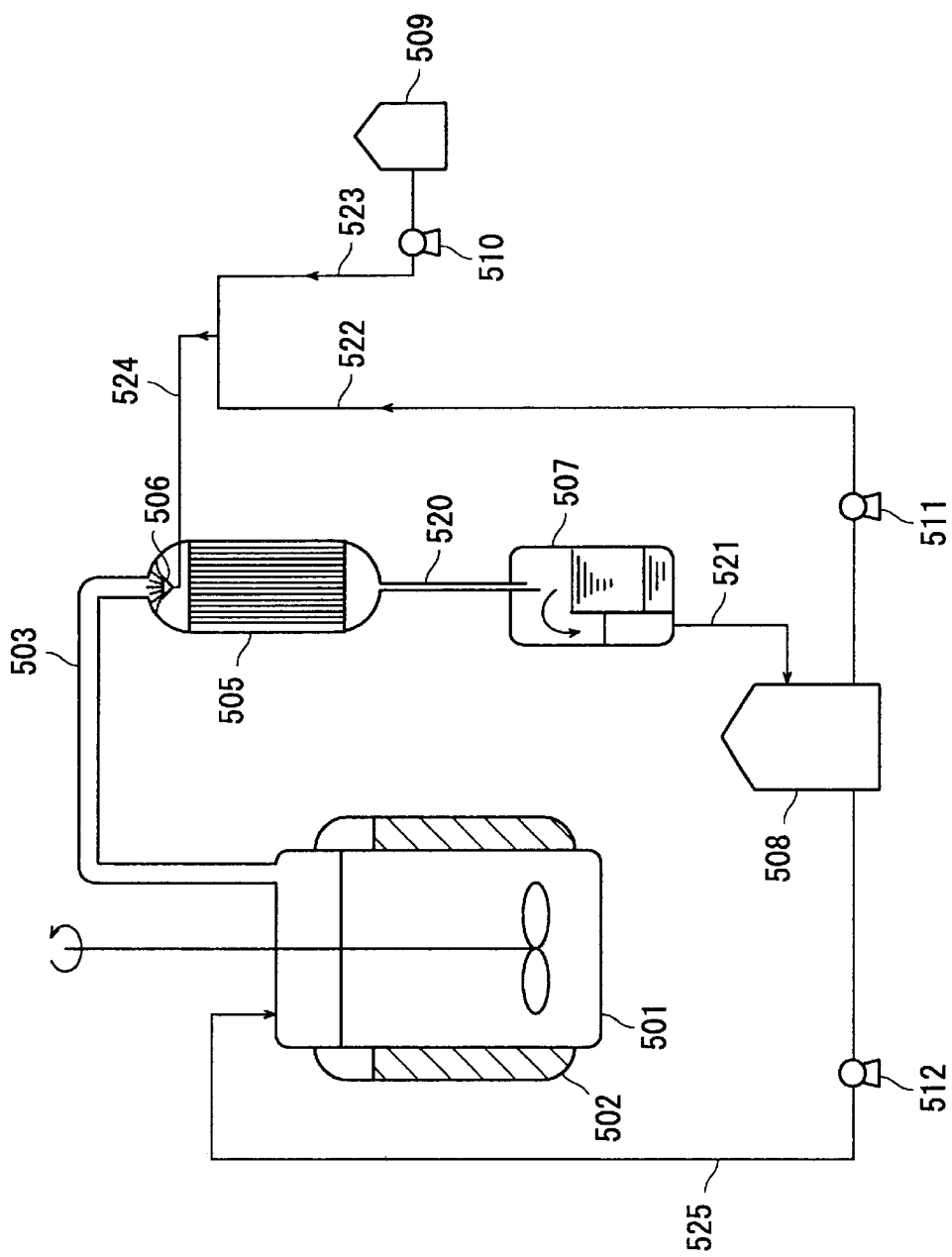
FIG. 2 is a schematic explanatory diagram illustrating one embodiment of the apparatus of this invention for production including the construction of a typical antigelling agent-supplying mechanism according to this invention.
Figure 3:
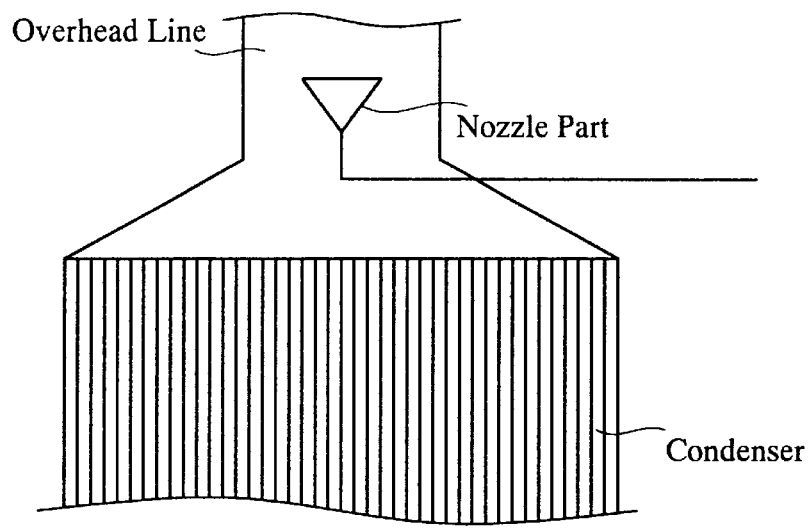
FIG. 3 is a schematic explanatory diagram illustrating the appearance of installation of a nozzle in an overhead line directly in front of a condenser.
Figure 4:
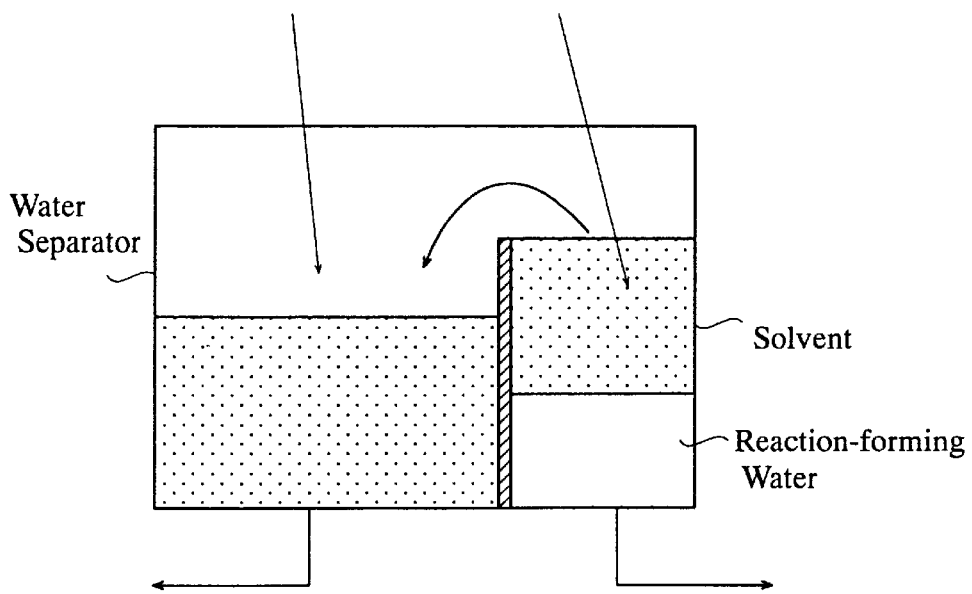
FIG. 4 is a schematic explanatory diagram of a water separator provided in combination with a preserving part.

(1) When a dehydrating solvent is used in the esterification reaction and then expelled by distillation and refluxed, a part of the residue of condensate may be extracted while being returned to the reaction tank, directly supplied to the nozzle part mentioned above, and transformed into the antigelling agent solution in the nozzle part or, alternatively while being supplied to the nozzle part mentioned above, mixed with the antigelling agent and converted into the antigelling agent solution. Specifically, the antigelling agent solution in the mixed state can be prepared simply by providing a preserving part (such as a tank) for temporarily storing the residue of condensate as occasion demands in the path for returning the residue of condensate to the reaction tank (preferably at the flange part intervening between the reaction tank and the vapor rising line) as illustrated in FIG. 2 which will be specifically described herein below, extracting a part of the residue of distillate from the preserving part, and allowing a part of the extracted residue of condensate to introduce into the path for supplying the antigelling agent. Any device for thoroughly mixing and stirring these two components is not required for this purpose. The merit of providing the preserving part herein resides in permitting convenient adjustment when the amount of the residue of condensate to be extracted for use in the antigelling agent solution is to be fixed or gradually increased and ensuring easy adjustment when the residue of condensate is refluxed to the reaction tank while keeping the amount of the residue of condensate constantly at a fixed level or repressing the increased amount thereof to be to the fullest possible extent between the time the reaction is started and the time the reaction is completed. Instead of additionally disposing such a preserving part as the preserving tank, a water separator, for example, itself may be made to serve as a preserving part if the water separator is provided so as to store in one of the opposite compartments thereof a condensate to be condensed and liquefied in the condenser, divide it into two layers, i.e. a water phase and a solvent phase, allow the water phase in the lower layer to be sequentially extracted through a pipe from the lower part of this compartment, and allow the solvent phase in the upper layer to overflow the partition plate and collect in another adjoining compartment which has been enlarged suitably for storing the solvent phase exclusively (see FIG. 4).

According to this invention, a preserving part is not always an indispensable component. As compared with the conventional case of using the antigelling agent by itself, since the antigelling agent solution containing the residue of condensate is used, for example, the antigelling agent can manifest gel preventing effects copiously in an amount equal to or smaller than the conventional level, and as a result, the increase of the amount of the solvent in the reaction tank may be repressed to a level equal to or smaller than the conventional level. Particularly when the time for esterification is short, the omission of the provision of the preserving part proves more advantageous economically because the decrease of the reaction temperature is small and the effect on the time for completing the reaction is permitted to be small. Further, when the amount of the solvent to be returned into the reaction tank is suffered to increase copiously, a part of the solvent may be extracted from the system instead of being returned to the reaction tank. In this case, since the amount of the solvent to be extracted from the system is not so large and the cost of treatment is small, the measure resorting to the extraction is more advantageous in economical view than the measure requiring elaborately provision of the preserving part and may not affect any performance of the finished product. It may well be concluded essential to judge properly whether a preserving part should be provided or not in due consideration of influence affected on the performance and further the cost performance.

(2) When the esterification reaction is carried out in the absence of a dehydrating solvent, the distillate may be inherently limited to the reaction-forming water (containing a trace amount of a raw material with a low boiling point) and the reflux of a part of the distillate to the reaction tank is no longer necessary. It is, therefore, permissible to prepare an antigelling agent solution by either extracting wholly or partly a residue of condensate obtained by separating and removing the reaction-forming water (including a raw material with a low boiling point) from a condensate resulting from the action with the antigelling agent solution on the distillate, directly supplying the extracted residue to the nozzle part mentioned above, and converting the residue into the antigelling agent solution in the nozzle part or causing the extracted residue, while being supplied to the nozzle part mentioned above, to be mixed with the antigelling agent. Incidentally, when a part of the residue of condensate is utilized, the remainder of the residue of condensate may be extracted from the system.

The method for the action of the antigelling agent solution and the method for the reflux described above are only meant to illustrate typical measures. The present invention is not restricted thereto.

The method for the production according to the second aspect of this invention, as described above, is characterized by performing the esterification reaction meanwhile expelling by distillation water formed during the esterification reaction in conjunction with a dehydrating solvent, condensing and liquefying the distillate containing the water, separating and removing the water from the condensate resulting from the condensation and liquefaction, and returning to the reaction tank the residue of condensate containing the dehydrating solvent remaining after the separation and removal of the water, and causing the antigelling agent solution containing a part of the residue of the condensate and an antigelling agent to act on the distillate during the course of the esterification reaction. By this method, the amount of the residue of condensate to be increased in the reaction tank can be repressed to the fullest possible extent and the antigelling agent solution can be constantly supplied (dropwise from the top of the condenser column) in a fully sufficient amount (particularly enough to wet sufficiently the wall surface of the condenser, i.e. the site at which the distillate is condensed and liquefied, especially the wall surface of the column top thereof) to the distillate. Thus, the emission of a gel-like substance with a raw material with a low boiling point which is expelled by distillation in conjunction with the reaction-forming water while the water in the reaction tank is expelled by distillation from the reaction tank, condensed and liquefied, and separated and removed can be constantly and effectively prevented and the esterified product of high quality can be efficiently and inexpensively produced.

According to the third aspect, this invention is to provide a method for the production of an esterified product by the esterification reaction of an alcohol represented by the formula (1):

$$R^1(R^2O)_nH \quad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid in the presence of a dehydrating agent, wherein said method further comprises a step of causing an antigelling agent to act on a distillate containing the dehydrating solvent during the step of expelling by distillation the dehydrating solvent after the completion of the esterification reaction. The aspect described above may embrace a mode of causing the antigelling agent to act on the distillate emitted by esterification, namely a mode of causing the antigelling agent to act on the distillate produced by expelling by distillation water formed during the esterification reaction in conjunction with the dehydrating solvent, according to the first aspect and/or a mode of performing the esterification reaction meanwhile expelling by distillation water formed during the esterification reaction in conjunction with the dehydrating solvent, condensing and liquefying the distillate containing the water, separating and removing the water from the condensate resulting from the condensation and liquefaction, and returning to the reaction tank the residue of condensate containing the dehydrating solvent remaining after the separation and removal of the water, and causing an antigelling agent solution containing a part of the residue of condensate and an antigelling agent to act on the distillate during the course of the esterification reaction according to the second aspect.

The third aspect of this invention consists in expelling by distillation a dehydrating solvent after the esterification reaction has been performed in the dehydrating solvent. Thus, this invention comprises essentially a solvent-expelling step. When the esterification reaction mentioned above is carried out in the present of an acid catalyst, the acid catalyst and further a part of the (meth)acrylic acid may be neutralized by the partial neutralization step according to the first aspect mentioned above and subsequently the dehydrating solvent may be expelled by distillation after the esterification reaction has been carried out.

In the aspect described above, the esterification reaction has the same definition as in the first aspect described above, excepting the esterification reaction be essentially carried out in the presence of a dehydrating agent. The terms "alcohol", "(meth)acrylic acid", and the like, other than the definitions concerning the solvent-expelling step in the first and second aspects mentioned above, have the same meanings as used in the first and second aspects mentioned above.

Further, according to the third concept, since the dehydrating solvent is required to be expelled by distillation from the reaction tank during the solvent-expelling step after the completion of the esterification reaction, the term "distillate" in the aspect generally contains the dehydrating solvent and additionally contains the raw material, particularly (meth)acrylic acid, which is expelled by distillation together with the dehydrating solvent when this solvent is expelled by distillation from the reaction tank.

Now, therefore, a preferred embodiment of the solvent-expelling step according to the third aspect will be described herein below.

The solvent-expelling step according to this invention is characterized by causing an antigelling agent to act on the distillate containing the dehydrating solvent during the expulsion by distillation of the dehydrating solvent after the completion of the esterification reaction (optionally comprising the treatment of partial neutralization). By this step, the occurrence itself of the gel-like substance (such as poly(meth)acrylic acid) which is formed with (meth)acrylic acid, i.e. a low boiling raw material mixed into the distillate containing the dehydrating solvent during the expulsion by distillation of the dehydrating solvent after the completion of the esterification reaction can be effectively prevented to allow the production of an esterified product with high purity and high quality.

The antigelling agent which can be used in the aspect mentioned above for the purpose of affecting on the distillate containing the dehydrating solvent after the completion of the esterification reaction does not need to be particularly discriminated but has only to be capable of repressing the occurrence of the polymerization reaction at the stage at which the unaltered low boiling raw material contained in the distillate is condensed and liquefied. It can be properly selected, similarly to the definition in the first aspect mentioned above, among varying antigelling agents known to the art. As concrete examples of thereof, phenothiazine, tri-p-nitrophenyl methyl, di-p-fluorophenyl amine, diphenyl picryl hydrazyl, N-(3-N-oxyanilino-1,3-dimethyl butylidene) aniline oxide, benzoquinone, hydroquinone, methoquinone, butyl catechol, nitroso benzene, picric acid, dithiobenzoyl disulfide, cupferron, and copper (II) chloride may be cited. Among other antigelling agents mentioned above, phenothiazine, hydroquinone, and methoquinone may be used favorably on account of the solubility in a dehydrating solvent and water. These antigelling agents may be used either singly or in the form of a mixture of two or more members.

The amount of the antigelling agent to be used (added), though variable with the distilling temperature (quantity of heat) and the amount of the dehydrating solvent used for the esterification reaction (and further the amount of the water added after the completion of the esterification reaction), has only to be commensurate with the amount of an unaltered low boiling raw material to be expelled by distillation, namely to be capable of constantly and effectively preventing the successively emanating unaltered low boiling raw material from forming a gel-like substance between the time the expulsion by distillation of the distillate containing the dehydrating solvent is started and the time the dehydrating solvent is thoroughly expelled by distillation. It is generally in the range of 0.1 to 1000 ppm, preferably in the range of 1 to 500 ppm, based on the total amount of the alcohol of the formula (1) and the (meth)acrylic acid to be used (charged) as raw materials. If the amount is less than 0.1 ppm based on the total amount of the raw materials to be used, a shortage would possibly encounter occurrence of a gel-like substance. This amount may well be regarded as insufficient for manifesting constantly and effectively the polymerization inhibiting ability to the unaltered low boiling raw material successively emanating between the time the expulsion by distillation of the distillate containing the dehydrating solvent is started and the time the dehydrating solvent is thoroughly expelled by distillation. Conversely, if the amount exceeds 1000 ppm based on the total amount of the raw materials to be used, this amount would be unduly large for the effectively manifesting the polymerization inhibiting ability and the excess would neither realize a normally expected proportionate addition to the effect thereof nor do any good economically. When the antigelling agent to be used is added wholly at once, the formation of a gel-like substance with an unaltered low boiling raw material successively expelled by distillation between the time the expulsion by distillation of the distillate containing the dehydrating solvent is started and the time the dehydrating solvent is thoroughly expelled by distillation can not be easily inhibited effectively. It is, therefore, desirable to add successively (continuously) the antigelling agent as adjusted in a necessary amount commensurate with the time-course change of the amount of the dehydrating solvent contained in the distillate between the time the expulsion by distillation of the distillate containing the dehydrating solvent is started and the time the dehydrating solvent is thoroughly expelled by distillation so that the final total amount of addition may fall within the range mentioned above.

The manner for causing an antigelling agent to act as expected (including a mode of action and an acting region) does not need to be particularly restricted so long as this agent be enabled to act (by contact) effectively on raw materials of low boiling points (fluid substances) successively emanating from the reaction system. The antigelling agent may be caused to act, for example, (a') on the gaseous distillate prior to the condensation and liquefaction or (b') on the liquefied distillate which has already been condensed and liquefied. Optionally, these two manners (a') and (b') may be utilized in combination.

Now, preferred methods for acting an antigelling agent mentioned above will be described below with reference to respective modes of action. This invention allows proper combination of these methods and suitable adoption of the other acting methods well-known to the art. The acting methods illustrated herein below may be typical examples cited for the purpose of enabling persons of ordinary skill in the art to understand this invention easily. Naturally, this invention should not be limited to or by these examples.

(1') Method for Causing the Antigelling Agent to Act in a Mixed (dissolved) State in a Liquid:

This method comprises mixing an antigelling agent with a proper liquid (such as, for example, a solvent, preferably a solvent similar in kind to a dehydrating solvent used in the reaction or water) to prepare a liquid (the resultant liquid containing the antigelling agent as simply dispersed, preferably as dissolved), and adding dropwise or spraying the resultant liquid to the region for condensing the distillate containing the dehydrating solvent (preferably the distillate in the form of an azeotropic mixture of the dehydrating solvent with water), specifically to the condensing and liquefying device for effecting condensation and liquefaction of the distillate containing the dehydrating solvent, such as, for example, the interior of the condenser, preferably from the upper part (especially the proximity of the column top) of such a device as a condenser to the interior thereof in such a manner as to establish parallel contact with the distillate. Alternatively, depending on the kind or type of the condensing and liquefying device, a solution containing an antigelling agent may be placed in advance in the interior of the device such as a condenser and then exposed to contact (for intimate solution or dispersion) with a gaseous distillate to be blown in or the liquefied distillate to be cast in. Further, although in the above embodiment, the acting site with an antigelling agent is described as an interior of a condenser for condensing and liquefying a distillate, there may be other positions prone to the occurrence of gel such as, for example, a joint part (flange part) between a reaction tank and a line for guiding a rising vapor, a flange part interposed between a vapor line and a top part of the column of the condenser, a thermometer provided on the reaction tank, and a projecting part formed around the inspection window, as well as the condensing part inside the condenser. Among other positions mentioned above, the condensing part inside the condenser (especially near the column top), the flange part between the reaction tank and the vapor rising line, and the flange part between the vapor line and the top part of the column of the condenser prove particularly advantageous to be the acting site with an antigelling agent. Further, the above acting site may be used or alternatively, a plurality of the above acting sites may be used simultaneously if necessary.

(2') Method for Causing the Antigelling Agent to Act in a Solidified State:

An antigelling agent in a powdery state may be dropped or sprayed onto a region for condensing a distillate containing a dehydrating solvent, specifically to an interior of a condenser for condensing and liquefying a distillate containing a dehydrating solvent, preferably from an upper part of a condenser (especially a column top) to the interior thereof in such a manner as to establish parallel contact with the distillate. It may be otherwise permissible, though depending on such factors as a kind or type of condenser, to have an antigelling agent in the form of particles of a fixed particle diameter placed by loading or filling in advance in the condenser and then exposed to the distillate for required contact. Further, although in the above embodiment, the acting site with an antigelling agent is described as an interior of a condenser for condensing and liquefying a distillate, there may be other positions prone to the occurrence of gel such as, for example, a joint part (flange part) between a reaction tank and a line for guiding a rising vapor, a flange part interposed between a vapor line and a top part of the column of the condenser, a thermometer provided on the reaction tank, and a projecting part formed around the inspection window, as well as the condensing part inside the condenser. Among other positions mentioned above, the condensing part inside the condenser (especially near the column top), the flange part between the reaction tank and the vapor rising line, and the flange part between the vapor line and the top part of the column of the condenser prove particularly advantageous to be the acting site with an antigelling agent. Further, the above acting site may be used or alternatively, a plurality of the above acting sites may be used simultaneously if necessary.

(3') Method for Causing the Antigelling Agent to Act in a Gasified State:

This method comprises gasifying (inclusive of subliming) an antigelling agent and, prior to condensing and liquefying a distillate containing a gaseous condensate liquid (including an unaltered raw material of a low boiling point), supplying the gasified antigelling agent into the path in the pipe inter communicating between the device used for expelling by distillation the dehydrating solvent (preferably utilizing the reaction device used for the esterification reaction in its unmodified form) and the condensing and liquefying device such as a condenser, and mixing the relevant components therein.

In the methods (1') to (3') mentioned above, it may well be regarded as commendable to adopt the method (1') for the following reason. Specifically from the economic point of view and in terms of the ease of handling, a dehydrating solvent may be preferably expelled by distillation and removed at the lowest permissible temperature. As a measure satisfying the description, a method which comprises effecting the expulsion by distillation while using water in a suitable amount (particularly, when the aforementioned partial neutralization step resorts to a treatment with an aqueous alkali solution of a low concentration, the water already exists in a large amount in the system and this water is available for the distillation) may be cited as effective means. When the water is used in a proper amount to effect expulsion by distillation (azeotropic) of the dehydrating solvent, the low boiling raw material is also migrated toward the water phase and expelled by distillation in conjunction with the water and the content of the dehydrating solvent in the distillate gradually expelled azeotropically in accordance as the expulsion by distillation of the dehydrating solvent gradually advances is lowered, and eventually the water (containing the low boiling raw material) is expelled by distillation exclusively. Thus, the solution of the antigelling agent in the solvent is no longer capable of manifesting a fully satisfactory effect. It is commendable to adopt the method of (1') mentioned above for causing the antigelling agent to produce the action thereof as mixed with water. It is particularly preferable to adopt a water-soluble antigelling agent and causes this water-soluble antigelling agent to produce the action thereof as dissolved in water. For the purpose of enabling the antigelling agent to manifest the action thereof to the distillate containing the unaltered low boiling raw material [specifically for the sake of promptly contacting the antigelling agent with the liquefied product arising during the condensation (liquefaction) of the distillate containing the low boiling raw material thereby intimately dissolving or dispersing in the liquefied product (water and organic solvent) containing the low boiling raw material prone to gelation], it is further commendable to cause the antigelling agent dissolved in water and/or a solvent depending on the composition of the distillate to produce the action thereof in accordance with the method (1') mentioned above. It suffices, for example, to vary the composition of the antigelling agent intended to manifest the action (such as, in the case of using a plurality of species of antigelling agents, for example, the mixing ratio of each the antigelling agents to be dissolved in a solvent, preferably in a dehydrating solvent) while monitoring the time-course change in the composition of the distillate with the aid of a sensor, for example. The procedure of causing the antigelling agent dissolved in the dehydrating solvent by reason of solubility therein and the antigelling agent dissolved in water likewise by reason of solubility therein to be advanced through their respective paths, adding them dropwise or spraying through the respective spray nozzles disposed in the device such as the condenser thereby allowing them to manifest their proper actions proves advantageous. As one reason for the adoption of the method (1') mentioned above, an advantage that a liquid incorporating the antigelling agent of the nature described above can be made to function effectively as one of the means for liquefaction and condensation (i.e., a heat-exchange medium) in accordance as the amount of the liquid to be used for the antigelling agent increases per unit weight may be cited.

Here, hydroquinone, methoquinone, and etc. may be preferably used, for example, which can be used as the water-soluble antigelling agent when the antigelling agent is made to act in a state dissolved in water.

In contrast, when the antigelling agent is made to function in a state dissolved in a solvent, the solvents in which can dissolve the antigelling agent include benzene, toluene, xylene, cyclohexane, acetone, methylethyl ketone, n-hexane, and heptane. It is commendable to use a solvent similar in kind to the dehydrating solvent which is used in the esterification reaction. When two dissimilar solvents are used, since an attempt to separate the mixed solvents and recover the component solvents and put them to reuse requires treatments of separation and purification to be performed on a multistage pattern, the reclamation entails a high cost and the practice of discarding the spent solvents proves less expensive than the reclamation. Even the work of discarding the mixed solvent as no longer useful (the work of incineration or the work of diluting the mixed solvents to a concentration below the tolerable limit fixed by the environment standard and releasing the diluted mixed solvents into the nearby drainage) calls for a certain amount of cost, induces air pollution or water pollution in no small measure, and goes against the popular slogan of today advocating the building of an environment gentle to the earth. In contrast, the use of a solvent similar in kind to the dehydrating solvent allows the reclamation to be attained by a simple treatment at a low cost and deserves the name of superiority in cost and respect for environment.

In the aspect described above, for the sake of causing the antigelling agent to function in a state dissolved in a liquid (water and/or a solvent) and thereby repressing the occurrence of a gel-like substance, it suffices to supply the antigelling agent in such a manner that it may constantly continue its presence and manifest its function effectively on a raw material with a low boiling point (in a gaseous or liquid form) passing the interior of the apparatus such as a condenser. Though the mixing ratio of the antigelling agent and the liquid does not need to be particularly restricted, (A) the antigelling agent of the water-soluble type is used in an amount in the range of 0.001 to 10 parts by weight, preferably in the range of 0.01 to 5 parts by weight, based on 100 parts by weight of water when it is made to function as dissolved in water, or (B) the antigelling agent is used in an amount in the range of 0.001 to 10 parts by weight, preferably in the range of 0.01 to 5 parts by weight, based on 100 parts by weight of the solvent when it is made to function as dissolved in the solvent. If the amount of the water-soluble antigelling agent is less than 0.001 part by weight based on 100 parts by weight of water or if the amount of the antigelling agent is less than 0.001 part by weight based on 100 parts by weight of the solvent, it would possibly become difficult to have the antigelling agent of a suitable concentration contact efficiently and effectively with a raw material of a low boiling point in the distillate. Further, this shortage would prove to be economically disadvantageous because the amount of the liquid per unit weight of the antigelling agent consequently increases and the cost of treatment such as the disposal which ensues after the expulsion by distillation of the antigelling agent from the system in conjunction with the dehydrating solvent likewise increases. Conversely, if the amount of the water-soluble antigelling agent exceeds 10 parts by weight based on 100 parts by weight of water or if the amount of the antigelling agent exceeds 10 parts by weight based on 100 parts by weight of the solvent, the excess would bring a disadvantage that because of the consequence decrease of the amount of the liquid to be used (the total amount of the liquid added during the expulsion of the dehydrating solvent by distillation), the amount of addition per unit time per unit volume would be limited, the frequency of contact with a low boiling raw material decreases proportionately, and the effective repression of the liquefaction without contact and the formation of a gel substance would become difficult. For the purpose of ensuring the necessary amount of addition per unit time per unit volume, therefore, it becomes necessary to use the antigelling agent in an amount larger than the amount specified above and therefore endure a proportionate addition to the cost of production. When the two kinds of antigelling agents, one dissolved in water and the other in the solvent, are jointly used, the ratio thereof to be used does not need to adhere to the ranges specified in (A) and (B). It suffices to adjust suitably the total amount thereof so that the respective amounts may fall closely in the ranges specified in (A) and (B).

The mechanism of the apparatus to be employed in the process for expelling the solvent by distillation, namely the operation which comprises expelling by distillation the dehydrating solvent from the solution containing the esterified product formed in the system and the dehydrating solvent, condensing and liquefying the distillate, and removing the distillate from the system, does not need to be restricted in any respect so long as the apparatus should be provided with means (mechanism of device) for causing the antigelling agent to function during the course of the process. The apparatus may be constructed by suitably combining conventional devices heretofore known to the art. In the esterification process mentioned above, for example, a part of the mechanism of device used for expelling the dehydrating agent in the reaction system by distillation from the reaction system, condensing and liquefying the resultant distillate, and circulating the produced condensate back to the reaction system (hereinafter referred to simply as "solvent-circulating device") may be utilized. This utilization may be one of the preferred embodiments because it lends itself to promote simplification and miniaturization of the equipment. Specifically, concerning the condenser which is a device for condensing and liquefying the gaseous distillate, the solvent-circulating device mentioned above may be utilized in its unmodified form. Then, concerning the water separator which is a liquid-liquid separating device for separating and removing the condensed and liquefied distillate, the solvent-circulating device mentioned above may be utilized by being suitably modified. Specifically, depending on the ratio of components of the distillate, the liquid distillate transformed to the water separator may be handled by utilizing a route of transportation intended to remove water from the system and a pump which is a transporting device so that the water phase portion or the whole liquid distillate may be removed from the system. Alternatively, the water separator may be provided additionally with a vacuum pump (ejector) and enabled to effect selective removal of the component of relatively high volatility or to remove the liquid distillate wholly from the system. Otherwise, the condenser may be specially provided with a transportation route so that the condensed and liquefied distillate may be extracted wholly out of the system (into a device for waste disposal or a recycling device, for example) and suitably treated (discarded or reclaimed). These devices may be likewise preferably provided with a suitable control device. Naturally, the combination of the device mentioned above with other means heretofore known to the art or the replacement of this device with such other means and device may be suitably adopted instead of the mechanism of device illustrated above without departure from the primary concept of expelling the dehydrating solvent in the system by distillation, condensing and liquefying the distillate, and removing the condensate from the system.

This solvent-expelling process by distillation does not need to be particularly discriminated concerning the method for expelling the dehydrating agent by distillation from the solution containing the esterified product formed in the system and the dehydrating solvent after the reaction of esterification may be completed (optionally performing additionally the process of partial neutralization mentioned above). The dehydrating solvent may be removed by causing it to form an azeotropic mixture with water as described above. Otherwise, the dehydrating solvent may be effectively removed by using another suitable additive. Alternatively, the removal may be attained by distillation without using any additive (including water). Since the use of an acid catalyst is very useful in the esterification reaction (this usefulness may well deserve high esteem even in consideration of the necessity for subsequently performing partial neutralization), however, the method for removing the dehydrating solvent by causing it to form an azeotropic mixture with water may be regarded as one of the preferred embodiments. When the treatment for partial neutralization of the acid catalyst has been performed before the solvent-expelling step by distillation mentioned above, the solution containing the esterified product formed in the system and the dehydrating solvent no longer contains the active acid catalyst or an alkali (which would have been converted into the corresponding salt by the neutralization) and does not induce the reaction of hydrolysis even when it is heated in the presence of added water. The solution, therefore, permits the formation of the azeotropic mixture with water for the purpose of expelling the dehydrating solvent. Incidentally, the azeotropic distillation with water is rather capable of removing the dehydrating solvent efficiently at a lower temperature.

In the solvent-expelling process by distillation according to the third aspect of this invention, the conditions for expelling the dehydrating solvent by distillation from the solution in the system do not need to be particularly restricted so long as they allow the dehydrating solvent in the system to be expelled advantageously by distillation. The inner temperature of the system during the expulsion of the solvent (liquid temperature in the system (under normal pressure)) is generally (1") in the range of 80° to 120° C., preferably in the range of 90° to 110° C., for example, when water is used. It is generally (2") in the range of 80° to 160° C., preferably in the range of 90° to 150° C. when water is not used. If this temperature is lower than the lower limit of the range defined in (1") or (2"), this temperature (quantity of heat) would not suffice the distillation of the dehydrating agent and bring a disadvantage that the expulsion of the dehydrating agent by distillation consumes an unduly long time. If the temperature is higher than the upper limit of the range defined above, the excess would bring a disadvantage that it threatens polymerization and consumes a large quantity of heat for the distillation of a low boiling raw material existing in a large amount. Further, although the pressure in the system (device) may be normal pressure or a decreased pressure, the distillation is preferred to be performed under normal pressure from the viewpoint of the equipment. For performing the expulsion of the solvent by distillation from the solution containing the dehydrating solvent, it is commendable to use a device (reaction tank) which is used for the esterification reaction. If the content of the device is specially transferred to some other device after the esterification reaction, the transfer would bring a disadvantage that the cost of equipment and management increases, the esterified product and the like are deteriorated by external factors (heat, light, ambient heat and pressure during the transfer, and presence of active ambient gas etc.) and suffered to deposit fast on the path for transfer, the path for transfer needs to protect itself against leakage of extraneous matter from the device during the course of transfer, and the transfer itself incurs an extra cost.

When the esterification reaction is carried out in the presence of a polymerization inhibitor in order to prevent the (meth)acrylic acid from the polymerization during the course of esterification, the solution in the system does not require new supply of the polymerization inhibitor during the course of the distillation of the solvent because the polymerization inhibitor can effectively function even after the esterification reaction (and further after the treatment of partial neutralization). When the treatment of partial neutralization is performed by using an aqueous alkali solution of a low concentration, the solution in the system allows the presence of a relatively large amount of water. Exclusively when a polymerization inhibitor used during the reaction of esterification happens to be sparingly soluble or insoluble in water, it possibly succumbs to polymerization in the solution of the system in which the (meth)acrylic acid is dissolved in water. From the viewpoint of preventing this polymerization, the temperature may be preferably elevated to the level specified above after the water-soluble polymerization inhibitor is added to the solution in the system.

The water-soluble polymerization inhibitor mentioned above does not need to be particularly restricted. It may be selected among hydroquinone, methoquinone, catechol and derivatives thereof (such as, for example, p-t-butyl catechol), and hydroquinone monomethyl ether, for example. These water-soluble polymerization inhibitors may be used singly or in the form of a mixture of two or more members.

The amount of the water-soluble polymerization inhibitor to be added is in the range of 0.001 to 1% by weight, preferably 0.001 to 0.1% by weight, based on the total amount of the alcohol and (meth)acrylic acid as the raw materials to be used. If the amount of the water-soluble polymerization inhibitor to be added is less than 0.001% by weight, there would be a possibility that the polymerization inhibiting ability be manifested insufficiently. If this amount exceeds 1% by weight, the excess would be wasted and will not do any good economically.

According to the fourth aspect, this invention is to provide an apparatus for the esterification to be used for the method of this invention, which apparatus comprises a reaction tank for the esterification reaction of an alcohol represented by the following formula:

$$R^1O(R^2O)_nH \qquad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 0 to 300, with (meth)acrylic acid, a condenser for condensing and liquefying a distillate emanating from the reaction tank, an antigelling agent-supplying mechanism disposed at at least one point on a connecting pipe intervening between the reaction tank and the condenser, and a water separator for separating and removing water from the condensate.

In the aspect described above, the esterification reaction has the same definition as in the first aspect and the terms "alcohol", "(meth)acrylic acid", and "distillate" used therein have the same meanings as used in the first, second, and third aspects mentioned above.

The apparatus to be used for the method for the production of the esterified product according to this invention is characterized by comprising a reaction tank for the esterification reaction, a condenser for condensing and liquefying a distillate emanating from the reaction tank, an antigelling agent-supplying mechanism, preferably an antigelling agent-supplying mechanism for causing an antigelling agent solution containing at least a part of the condensate to act on the distillate, disposed at at least one point on a connecting pipe intervening between the reaction tank and the condenser, and a water separator for separating and removing water from the condensate arising from the condenser, and is characterized by further comprising an antigelling agent-supplying mechanism for causing an antigelling agent solution containing at least a part of the condensate liquid to act on the distillate. The other devices of apparatus are not particularly restricted. The various devices for production such as processing machines heretofore known to the art may be suitably combined and used for the apparatus.

In the above aspect, the antigelling agent-supplying mechanism is preferred to be so constructed that a nozzle part for the action of the antigelling agent is disposed in the proximity of the top of the condenser column, namely in the inner part of the top of the condenser column or in the path for distillation immediately in front of the condenser. More preferably, the nozzle part is disposed as directly upwardly so that the antigelling agent solution may be supplied upwardly. Particularly for the purpose of keeping constantly in a wet state the inner wall of the top of the condenser column (namely, the inlet part for the distillate) which is liable to induce the occurrence of a gel-like substance, the nozzle part may be preferably disposed as turned upwardly in the top of the condenser column or in the central part on the path for distillation immediately before the condenser. The antigelling agent solution may be supplied to the inner wall of the top of the condenser column by causing the nozzle part disposed on the top of the condenser column or in the path for distillation immediately in front of the condenser to spray, blow out, blast, discharge, blow up, or blow down this solution, or alternatively the arrival of this solution at the interior of the condenser may be attained by supplying the solution to the wall of the overhead line immediately before the condenser and allowing the solution to pass along the wall. Thus, the solution is enabled to keep the inner wall of the condenser which is liable to induce the occurrence of a gel-like substance constantly in a wet state either directly or indirectly by flowing down the inner wall on the path.

Figure 5:
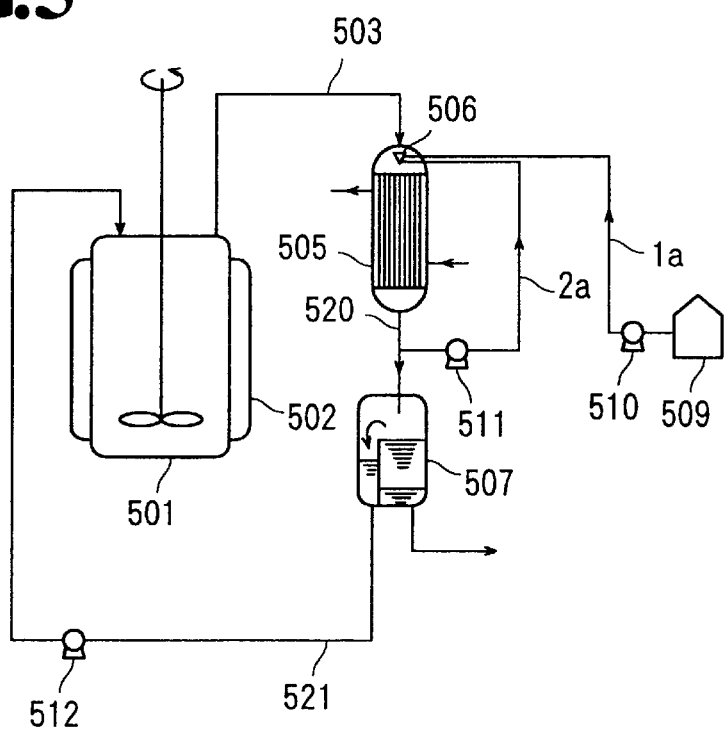
FIGS. 5 to 14 are schematic explanatory diagrams illustrating embodiments of the sequences as an antigelling agent-supplying mechanism of a first supply route for supplying the antigelling agent solution from the storage part for the antigelling agent solution to the nozzle part and a second supply route for supplying part of the condensate to the nozzle part.
Figure 6:
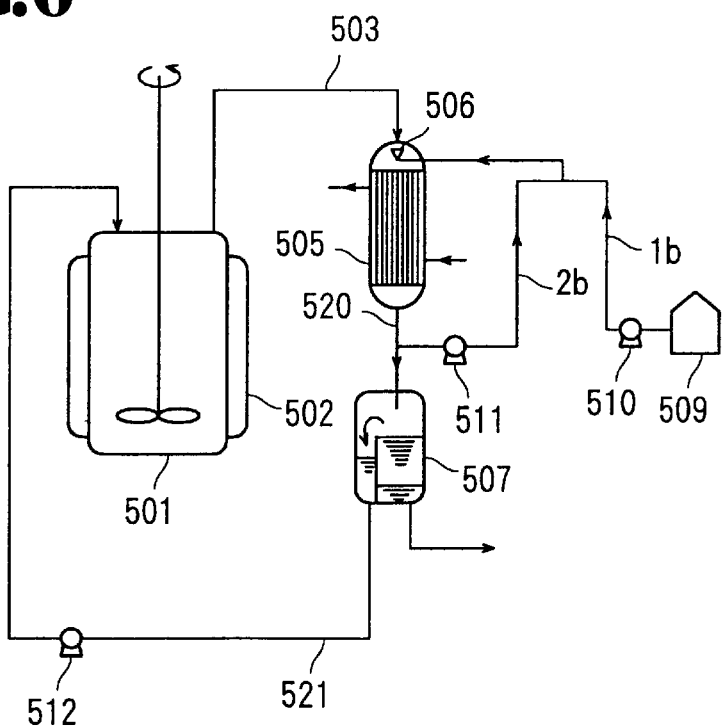
Figure 7:
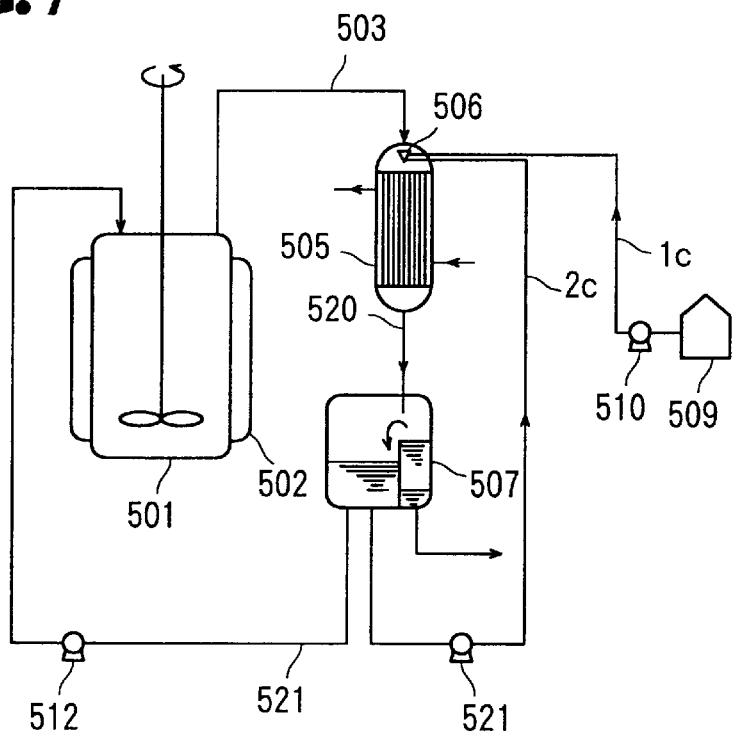
Figure 8:
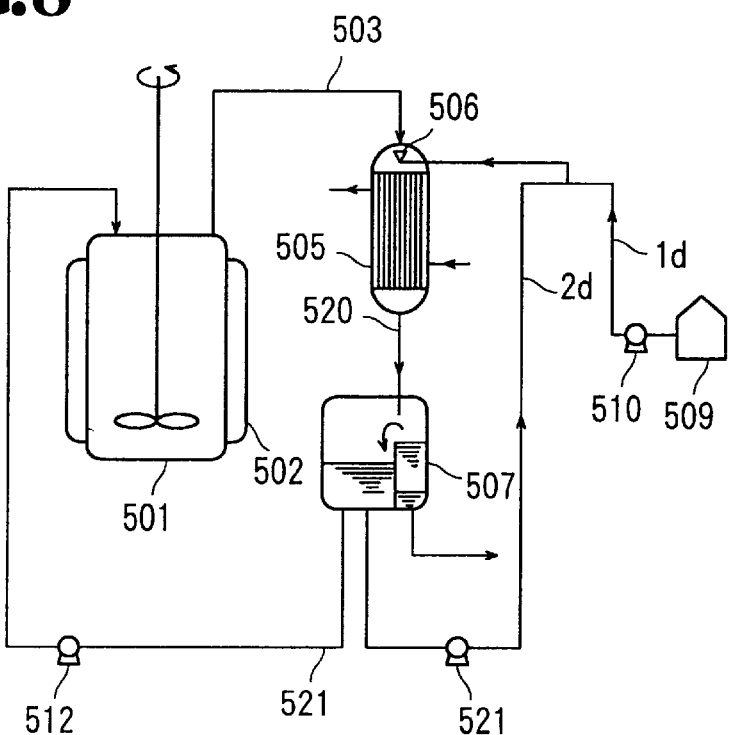
Figure 9:
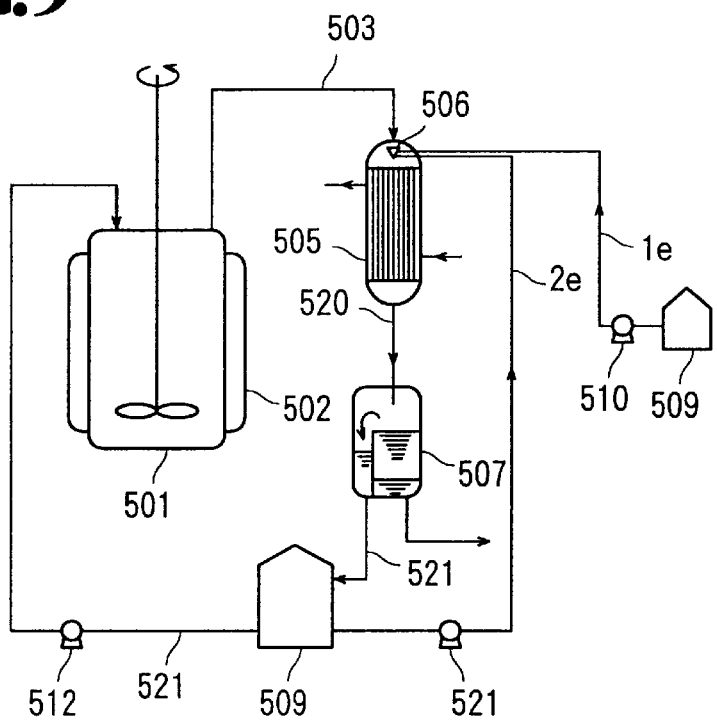
Figure 10:
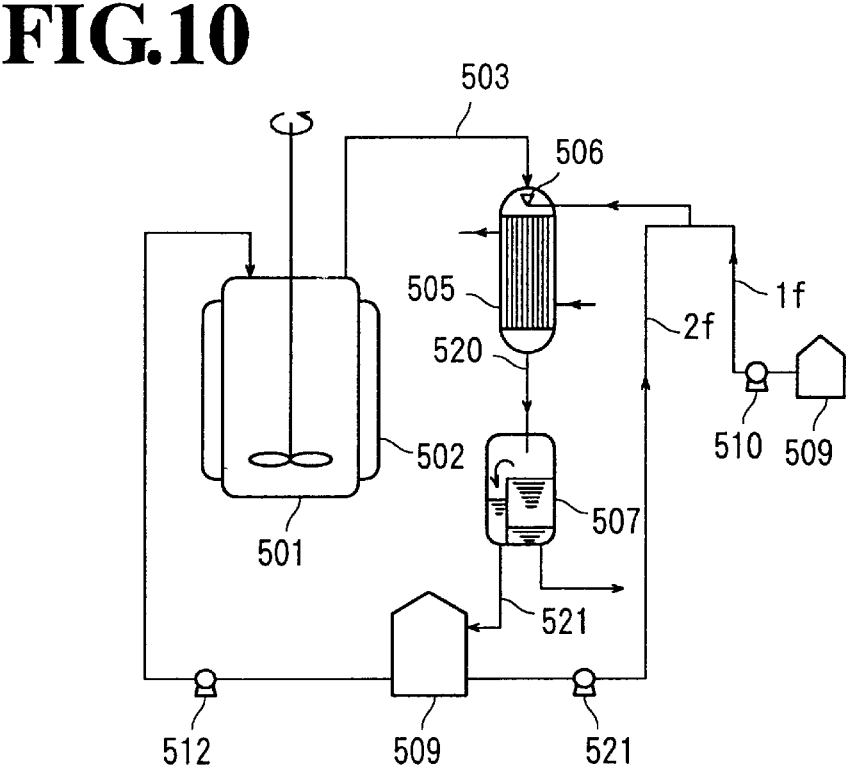
Figure 11:
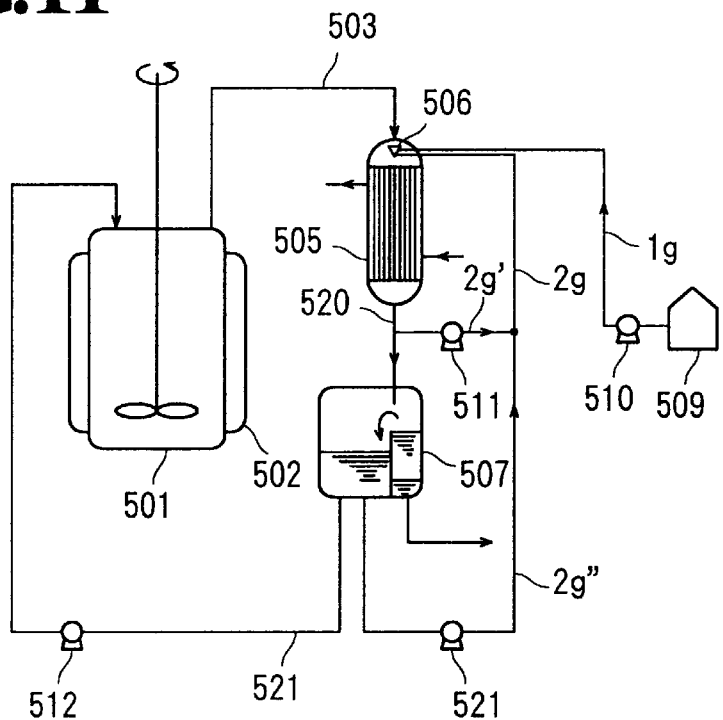
Figure 12:
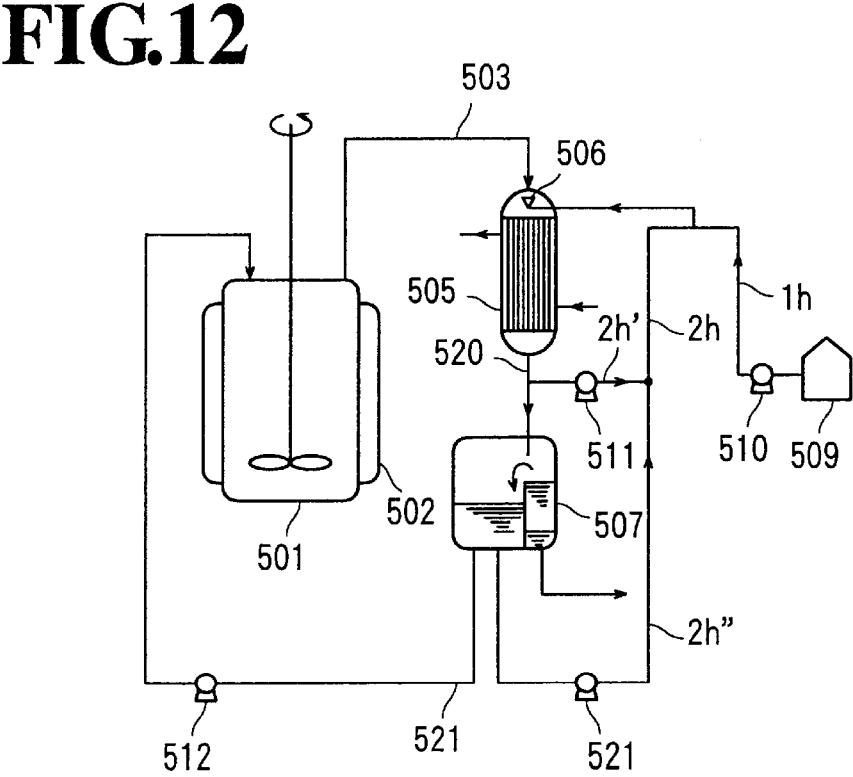
Figure 13:
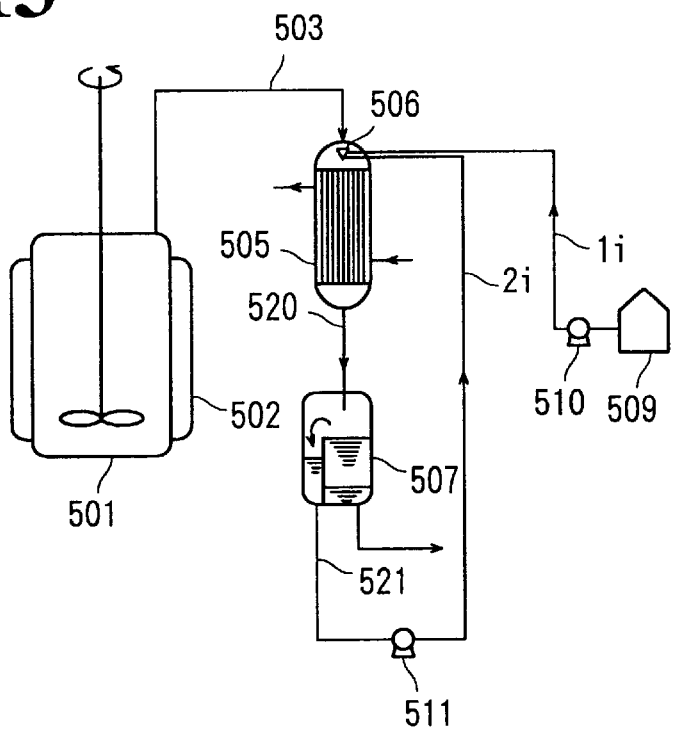
Figure 14:
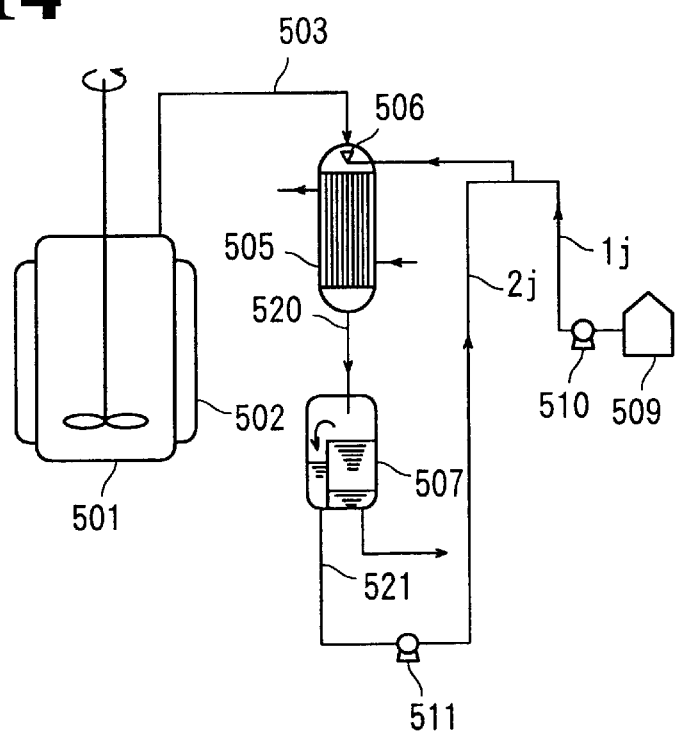

As one embodiment of the antigelling agent-supplying mechanism, the combination of a first supply route (capable of utilizing a suitable pipe and a compressor pump) for supplying the antigelling agent solution from the storage part for the antigelling agent solution to the nozzle part and a second supply route (capable of utilizing a suitable pipe and a compressor pump) for supplying a part of the condensate to the nozzle part may be cited. Now, the typical embodiments of the antigelling agent-supplying mechanism according to the aspect mentioned above will be illustrated in FIGS. 5 to 14. Specifically, FIGS. 5 to 14 are schematic explanatory diagrams illustrating embodiments of the sequences as an antigelling agent-supplying mechanism of a first supply route for supplying the antigelling agent solution from the storage part for the antigelling agent solution to the nozzle part and a second supply route for supplying part of the condensate to the nozzle part. In FIGS. 5 to 14, the same parts of apparatus illustrated in FIG. 1 are denoted by like reference numerals, or abbrebiated. More specifically, FIG. 5 depicts an arrangement in which a first supply path 1*a* and a second supply path 2*a* for supplying the condensate as simply divided are so disposed as to make relevant supply independently to the nozzle part; FIG. 6 an arrangement in which a first supply path 1*b* and a second supply path 2*b* for supplying the condensate liquid as simply divided are so disposed as to make relevant supply as joined to the nozzle part; FIG. 7 an arrangement in which a first supply path 1*c* a second supply path 2*c* for supplying a part of the condensate residue from the preserving part of the water separator are so disposed as to make relevant supply independently to the nozzle part; FIG. 8 an arrangement in which a first supply path 1*d* and a second supply path 2*d* for supplying a part of the condensate residue from the preserving part of the water separator are so disposed as to make relevant supply as joined to the nozzle part; FIG. 9 an arrangement in which a first supply path 1*e* and a second supply path 2*e* for supplying a part of the condensate residue from the preserving tank are so disposed as to make relevant supply independently to the nozzle part; FIG. 10 an arrangement in which a first supply path 1*f* and a second supply path 2*f* for supplying a part of the condensate residue from the preserving tank are so disposed as to make relevant supply jointly to the nozzle part; FIG. 11 an arrangement in which a first supply path 1*g* and a second supply path 2*g* comprising a path 2*g*' for supplying the condensate as simply divided partially and a path 2*g*" for supplying a part of the condensate residue from the preserving part of the water separator are so disposed as to make relevant supply independently to the nozzle part; FIG. 12 an arrangement in which a first supply path 1*h* and a second supply path 2*h* comprising a path 2*h*' for supplying the condensate as simply divided partially and a path 2*h*" for supplying a part of the condensate residue from the preserving part of the water separator are so disposed as to make relevant supply jointly to the nozzle part; FIG. 13 an arrangement in which a first supply path 1*i* and a second supply path 2*i* for supplying the whole of the condensate residue from the water separator are so disposed as to make relevant supply independently to the nozzle part; and FIG. 14 an arrangement in which a first supply path 1*j* and a second supply path 2*j* for supplying the whole of the condensate residue from the water separator are so disposed as to make relevant supply jointly to the nozzle part.

In the aspect described above, the second supply path has only to join the path for distillation (particularly the path for circulation) for forwarding the condensate liquid (particularly the residue of condensate) with the nozzle part mentioned above. The connection to the nozzle part mentioned above, for example, may be effected either directly or indirectly by being joined to the first supply path. Optionally, a path for distillation (particularly a path for circulation) may be provided thereon with the preserving part and this preserving part may be connected to the nozzle part mentioned above. As the preserving part mentioned above, a preserving tank disposed on the path for circulation between the water separator and the reaction tank and adapted to permit temporary storage of the residue of condensate or a part of the water separator (see FIG. 3) may be cited, for example. The first and second supply paths of the antigelling agent-supplying mechanism are preferred to be provided with means capable of adjusting arbitrarily the flow volume of part of the antigelling agent solution and the condensate. A proper flow volume adjusting valve may be cited as a concrete example. The provision of these devices facilitates the adjustment of the flow volume of the antigelling agent solution and a part of the condensate. When the first supply path and the second supply path are joined, one of the joined supply paths may be optionally provided thereon with means for mixing or stirring the antigelling agent solution and a part of the condensate. A baffle plate or a projection formed on the inner wall of the path directly behind the combined sites may be cited as a concrete example. As a result, the antigelling agent solution and a part of the condensate can be quickly and homogeneously mixed. When the first supply path and the second supply path are directly connected to the nozzle part mentioned above, the nozzle part may preferably have such an internal construction as that the antigelling agent solution and a part of the condensate are quickly stirred and mixed inside the nozzle part.

The apparatus for the production according to the fourth aspect of this invention is not particularly restricted excepting the provision of the antigelling agent-supplying mechanism described above. It permits suitable application thereto of varying devices, mechanisms, and means for the esterification reaction heretofore known to the art [reaction devices, mechanisms, and means such as, for example, reaction tanks for the esterification reaction of an alcohol with (meth)acrylic acid in the presence or absence of a dehydrating solvent, a polymerization inhibitor, and an acid catalyst (further, various storage tanks including raw material storage tanks, catalyst storage tanks, and solvent tanks, pipes, supply pumps, flow volume-adjusting valves, and switch valves), paths for distillation having condensers for condensing and liquefying the distillate emanating from the reaction tanks and water separators for separating and removing the reaction-forming water from the condensed and liquefied condensates mentioned above, and paths for circulation incorporating pressure delivery means for refluxing to the reaction tanks the residue of condensate remaining after separation and removal of the reaction formed water).

Now, the apparatus for the manufacture of the esterified product according to the aspect described above will be described more specifically below with reference to FIG. 2. FIG. 2 is a schematic diagram illustrating the construction of the typical apparatus to be used for the method for the production of the esterified product according to this invention, particularly the construction of the apparatus including the antigelling agent-supplying mechanism which forms a characteristic part. The other components of the apparatus (such as, for example, means for storage and supply of various additives like raw materials and catalysts) are identical with those of the apparatus of FIG. 1 and will be omitted from the following description.

As illustrated in FIG. 2, in one embodiment of the apparatus for the production of this invention including the antigelling agent-supplying mechanism, the upper part of a reaction tank 501 for the esterification reaction and the top of column of a counter flow (or parallel flow) contact type vertical shell-and-tube cylindrical condenser 505 may be connected via a pipe 503. The reaction tank 501 is provided externally thereon a jacket 502 as a heating means (such as, for example, an internal heater or an external jacket). It may be further provided with a suitable stirring device. The bottom part of the condenser 505 and the upper part of a water separator 507 may be connected via a pipe 520. The water separator 507 may be provided therein with a partition plate which separates the interior thereof into two compartments. The lower part of the compartment on the side for storing the distillate resulting from the condensation and liquefaction in the condenser 505 and a treating tank (not shown) for the reaction-forming water may be connected via a pipe (not shown). The lower part of the other compartment of the water separator 507 and the upper part of a preserving tank 508 for permitting temporary storage of the residue of condensate may be connected via a pipe 521. The lower part of the preserving tank 508 mentioned above and the upper part of the reaction tank 501 may be connected via a pipe 525. A circulation pump 512 may be disposed on the path of the pipe 525. As the antigelling agent-supplying mechanism, first a nozzle part 506 for spraying the antigelling agent solution to the top part of the condenser column may be disposed as turned upwardly in the central part of the top part of the condenser column 505. This nozzle part 506 and an antigelling agent solution storage tank 509 for storing the antigelling agent solution aimed at preventing possible gelation of the distillate may be connected via pipes 523 and 524 forming the first supply path (the part to which the antigelling agent solution is transported exclusively constitutes the pipe 523 and the part to which the mixed solution formed of a part of the residue of condensate and the antigelling agent is transferred constitutes the pipe 524). On the path of the pipe 523, a compressor pump 510 may be disposed. Further, the lower part of the preserving tank 508 and the first supply path may be connected with a pipe 522 which forms the second supply path for supplying part of the residue of condensate. A compressor pump 511 may be disposed on the path of the pipe 522.

The embodiment concerning the use of the apparatus for the production of the esterified product having the construction including the antigelling agent-supplying mechanism according to the aspect mentioned above according to this invention will be described below with reference to FIG. 2.

In the reaction tank 501, an alcohol and (meth)acrylic acid as raw materials, an acid catalyst, a polymerization inhibitor, and a dehydrating solvent are placed (charged) in prescribed amounts defined above and subjected to esterification under the conditions of esterification (reaction temperature, jacket temperature, pressure) as specified above. The water successively formed by the esterification reaction is azeotropically distilled with the dehydrating solvent placed in the reaction tank 501 and expelled through the pipe 503. The solvent-water azeotrope, a gaseous fluid resulting from the distillation, is condensed and liquefied by being passed through the condenser 505. For the purpose of preventing a low boiling raw material contained in the azeotrope during the condensation and liquefaction from being gelated, the antigelling agent solution is supplied from the storage tank 509 via the pipe 523 and, at the same time, a part of the residue of condensate is supplied from the preserving tank 508 via the pipe 522 and they are joined and mixed to form an antigelling agent solution. This antigelling agent solution is supplied via the pipe 524 to the nozzle part 506 disposed in the top part of the condenser column 505. Through this supply nozzle part 506, the antigelling agent solution is continuously sprayed or brown out as directed upwardly in the amount specified above to wet the whole inner wall embracing the gas inlet part of the top part of the condenser column to effect parallel contact with the distillate (meaning both the gas flow and the condensate liquid). The condensate liquid (including the antigelling agent solution admitted dropwise) which has been condensed and liquefied is forwarded from the lower part of the condenser 505 via. the pipe 520 and collected in one of the compartments of the water separator 507 and then divided into two layers, i.e. the water phase and the solvent phase. The water phase forming the lower layer part (including a low boiling raw material besides the reaction-forming water) is successively withdrawn from the lower part of this compartment via the pipe, collected in the treating tank for the reaction-forming water, and optionally chemically or biologically treated in the treating tank so as to satisfy the tolerable level fixed by the environment standard (waste water standard), and finally discarded from the system via the pipe for drainage. Meanwhile, the solvent phase forming the upper layer part (namely, the residue of condensate, including the antigelling agent solution and the low boiling raw material in addition to the dehydrating solvent) is allowed to overflow the partition plate and collect in another compartment. Then, the residue of condensate mentioned above is forwarded via the lower part of another compartment and temporarily stored in the preserving tank 508. Of the residue of condensate stored in the preserving tank 508, the part required to make up for the decrease of the dehydrating solvent distilled from the reaction tank 501 is returned by the pump 512 through the pipe 525 to the reaction tank 501. Further, a part of the residue of condensate stored in the preserving tank 508 is successively withdrawn by the pump 511 via the pipe 522 and used for the formation of the antigelling agent solution. Since the residue of condensate which can be used for the formation of the antigelling agent solution is not sufficiently stored in the preserving tank 508 for a brief time after the start of the reaction as mentioned above, the antigelling agent solution may be supplied exclusively to the nozzle part 506 until the residue off condensate is stored sufficient in the preserving tank 508. Alternatively, the dehydrating solvent (or the dehydrating solvent containing the antigelling agent in a suitable amount) in an amount of irreducible minimum necessary for the formation of the antigelling agent solution may be placed in advance in the preserving tank 508 and supplied via the pipe 522 from the initial stage of the reaction onward.

After the esterification reaction performed as described above has been completed (the time at which the ratio of esterification reaches a level above the specified ratio taken as the end point), the aqueous solution of a neutralizing agent is added to the interior of the reaction tank 501 to neutralize the acid catalyst. The dehydrating solvent (plus the excess (meth)acrylic acid) is azeotropically distilled with water under normal pressure to obtain the esterified product aimed at. For the purpose of expelling the dehydrating solvent and the excess (meth)acrylic acid by distillation, the distillate containing water formed during the esterification reaction in the reaction tank 501 is expelled by distillation and the distillate is condensed and liquefied while preventing the occurrence of a gel-like substance, and the reaction-forming water is separated and removed, and the reflux of the remainder of the distillate is effected by using a part of the construction of the apparatus. In this case, since the dehydrating solvent and the excess (meth)acrylic acid are required to be removed from the system without being refluxed thereto, they are withdrawn out of the system by using a vacuum pump (ejector) disposed in the water separator 507. They may be discarded as no longer useful or they may be chemically treated with an external device outside the system and put to reuse. Meanwhile, the resultant esterified product is forwarded from the reaction tank 501 via the pipe into the esterified product storage tank to be stored therein. When this esterified product is used for the synthesis of a cement dispersant, the esterified product is further polymerized as one of the monomer components in the reaction tank 501 to produce a polymer capable of forming a main component of the cement dispersant.

One embodiment of the apparatus for the production of an esterified product contemplated by this invention has been described with reference to FIG. 2. The apparatus for the production of an esterified product according to this invention is not restricted to this embodiment. It is only required to be capable of expelling water arising during the esterification reaction from the reaction tank via the path for distillation or the path for circulation and causing the antigelling agent solution to act effectively on the distillate containing the water. Otherwise, it does not need to be discriminated in any respect on account of method (means) for the production or construction of apparatus. It permits application of suitable combination of varying methods for the production and constructions of apparatus heretofore known to the art.

According to the fifth aspect, this invention is to provide a method for the production of a polycarboxylic acid type copolymer (referred to simply as "copolymer" or "polymer" in the present specification) for the use in a cement dispersant which comprises reacting by the esterification of a polyalkylene glycol with (meth)acrylic acid by the method according to any one of the aspects as mentioned above, to obtain an alkoxy polyalkylene glycol mono(meth)acrylic acid type monomer (a), and copolymerizing 5 to 98% by weight of said alkoxy polyalkylene glycol mono(meth)acrylic acid type monomer (a), 95 to 2% by weight of a (meth)acrylic acid type monomer (b) represented by the following formula (2):

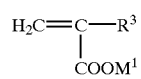

(2)

wherein $R^3$ represents a hydrogen atom or a methyl group, and $M^1$ represents a hydrogen atom, a monovalent metal element, a divalent metal element, an ammonium group, or an organic amine group, and 0 to 50% by weight of a monomer (c) copolymerizable with the monomers mentioned above, providing that the total amount of the monomers (a), (b), and (c) be 100% by weight.

In the above fifth aspect, the numeral value "n" in the formula (1) represents an average addition mol number of oxyalkylene groups and must be essentially in the range of 1 to 300. In this specification, an alcohol of the formula (1) wherein n is in the range of 1 to 300 is referred to as "polyalkylene glycol", and a compound which is obtained by the esterification reaction of a polyalkylene glycol with (meth)acrylic acid is referred to as "alkoxy polyalkylene glycol mono(meth)acrylic acid type monomer".

In the above aspect, the term "polyalkylene glycol" used therein is defined similarly to the term "alcohol" used in the first aspect, except for that n does not embrace 0. Then, such terms as "(meth)acrylic acid" and "esterification reaction" are as defined in the first to fourth aspects mentioned above.

Methods for the production of a polycarboxylic acid type copolymer (including the salts thereof; similarly applicable hereinafter) according to the fifth aspect may not be particularly restricted so long as it can produce a polymer, depending on the intended use therefor, by adopting an alkoxy polyalkylene glycol mono(meth)acrylic acid type monomer as a monomer component and subjecting this monomer component to the polymerization. The method should be interpreted as embracing what is polymerized in conformity with the intended use. For example, a cement dispersant excelling in cement dispersing ability can be produced by subjecting an alkoxy polyalkylene glycol mono (meth)acrylic acid type monomer to the polymerization in combination with (meth)acrylic acid (or the salt thereof) and optionally a monomer copolymerizable with these monomer components by any of the known methods as disclosed in JP-B-59-18,338, JP-A-09-86,990, and JP-A-09-286,645. These methods, however, should not be exclusive examples. Naturally, the polymerization methods which are disclosed in the patent publications cited in the detailed description are applicable. Besides them, various polymerization methods heretofore known to the art can applied as a matter of course. The esterified product can find utility in other applications including a pigment dispersant for calcium carbonate, carbon black, ink, and other pigments, and a scale remover, a dispersant for a slurry of gypsum and water, a dispersant for CWM, a thickener, and etc. As concrete examples thereof, methods which produces a polymer using the esterified product according this invention instead of a polymer as disclosed in JP-A-09-211,968 and JP-A-10-10,047 may be cited, all of which are contained in the scope of this invention.

More specifically, the method for the production of a polycarbonic acid type copolymer according to this invention comprises subjecting an alkoxy polyalkylene glycol mono(meth)acrylic acid type monomer, a (meth)acrylic acid (salt) monomer, and optionally a monomer copolymerizable with such monomers to the polymerization.

Here, for the purpose of obtaining a polycarboxylic acid type copolymer as desired, it suffices to copolymerize an alkoxy polyalkylene glycol mono(meth)acrylic acid type monomer and other monomer components by the use of a polymerization initiator. This copolymerization can be carried out by such a method as by polymerization in a solvent, bulk polymerization, and etc.

The polymerization in a solvent can be performed batchwise or continuously. As concrete examples of the solvent which can be used in the polymerization, water; lower alcohols such as methyl alcohol, ethyl alcohol, and isopropyl alcohol; aromatic or aliphatic hydrocarbons such as benzene, toluene, xylene, cyclohxane, and n-hexane; ester compounds such as ethyl acetate; and ketone compounds such as acetone and methylethyl ketone may be cited. In terms of the solubility of the esterified product, i.e. the monomer component as a raw material, and the resultant copolymer and the convenience of the copolymer during use, it is preferable to use at least one member selected from the group consisting of water and lower alcohols of 1 to 4 carbon atoms. In this case, among other lower alcohols of 1 to 4 carbon atoms, methyl alcohol, ethyl alcohol, and isopropyl alcohol may be used particularly effectively.

When the polymerization is performed in an aqueous medium, such water-soluble polymerization initiators as persulfates of ammonium or alkali metals or hydrogen peroxide maybe used for initiating the polymerization. In this case, the polymerization initiator may be used in combination with an accelerator such as, for example, sodium hydrogen sulfite or Mohr's salt. In the case of the polymerization using a lower alcohol, an aromatic hydrocarbon, an aliphatic hydrocarbon, an ester compound, or a ketone compound as a solvent, peroxides such as benzoyl peroxide and lauroyl peroxide; hydroperoxides such as cumene hydroperoxide; and aromatic azo compounds such as azobisisobutyronitrile may be used as a polymerization initiator. In this case, the polymerization initiator can be used in combination with an accelerator such as an amine compound. In the case of the polymerization using a mixed solvent of water with a lower alcohol, a polymerization initiator may be suitably selected among various polymerization initiators and various combinations of a polymerization initiator and an accelerator as mentioned above. The polymerization temperature may be generally in the range of 0° to 120° C., although it may be suitably selected depending on the kind of a solvent and a polymerization inhibitor to be used.

The bulk polymerization can be carried out using as a polymerization initiator a peroxide such as benzoyl peroxide or lauroyl peroxide; hydroperoxide such as cumene hydroperoxide; or an aliphatic azo compound such as azobisisobutyronitrile at a temperature in the range of 50° to 200° C.

For the adjustment of a molecular weight of the obtained polymer, it is permissible to use additionally a thiol type chain transfer agent. The thiol type chain transfer agent which can be used herein may be represented by the formula; HS-$R^5$-Eg (wherein $R^5$ represents an alkyl group of 1 to 2 carbon atoms, E represents a —OH, —$COOM^2$, —$COOR^6$, or —$SO_3M^2$ group, wherein $M^2$ represents a hydrogen atom, a monovalent metal element, a divalent metal element, an ammonium group, or an organic amine group, and $R^6$ represents an alkyl group of 1 to 10 carbon atoms, and g is an integer in the range of 1 to 2). As concrete examples thereof, mercaptoethanol, thioglycerol, thioglycolic acid, 2-mercaptopropionic acid, 3-mercaptopropionic acid, thiomalic acid, octyl thioglycolate, and octyl 3-mercapto propionate may be cited. These thiol type chain transfer agents may be used either singly or in the form of a mixture of two or more members.

The polymer which can be obtained as described above can be used in its unmodified form as a main component for varying end products such as a cement dispersant. Optionally, a polymer salt which is obtained by further neutralizing the polymer with an alkaline substance may be used as a main component for varying end products including a cement dispersant. As preferred concrete examples of the alkaline substance which is used for the neutralization, inorganic substances such as hydroxides, chlorides, and carbonates of monovalent metals and divalent metals; ammonia; and organic amines may be cited.

The alkoxy polyalkylene glycol mono(meth)acrylic acid type monomer components which can be used in the method for the production of a polymer according to this invention may be used either singly or in the form of two or more members. Especially when two or more such monomer components are used in a mixed form, it is commendable to use a suitably selected combination of two or more species differing in manifestation of characteristics so as to allow characteristics (including function and performance) to manifest conforming to the intended use. The combination of the following two species proves particularly advantageous.

As such an alkoxy polyalkylene glycol mono(meth) acrylic acid type monomer, a mixture of a first esterified product ($a^1$) which has an average addition mol number, n, in the formula (1) in the range of 1 to 97, preferably in the range of 1 to 10 with a second esterified product ($a^2$) which has an average addition mol number, n, in the formula (1) in the range of 4 to 100, preferably in the range of 11 to 100, providing that the average addition mol number of the second esterified product ($a^2$) is not less than 3 larger than the average addition mol number of the first esterified product ($a^1$), is an advantageous combination.

The method for producing the mixture of the first esterified product ($a^1$) with the second esterified product ($a^2$) is as described for the method for the production of an esterified product as mentioned above. The production may be otherwise attained by separately producing these first and second esterified products ($a^1$) and ($a^2$) in accordance with the esterification reaction or by subjecting the mixture of relevant alcohols and (meth)acrylic acid respectively to the esterification reaction. Particularly, the latter method allows the production to be carried out inexpensively on a commercial scale.

In this case, the weight ratio of the first esterified product ($a^1$) to the second esterified product ($a^2$) is in the range of 5/95 to 95/5, preferably 10/90 to 90/10.

As concrete examples of the first esterified product ($a^1$), methoxy (poly)ethylene glycol mono(meth)acrylate, methoxy polypropylene glycol mono(meth)acrylate, methoxy (poly)but ylene glycol mono(meth)acrylate, methoxy (poly)ethylene glycol (poly)propylene glycol mono(meth)acrylate, methoxy (poly)ethylene glycol (poly)butylene glycol mono (meth)acrylate, methoxy (poly)propylene glycol (poly) butylene glycol mono(meth)acrylate, methoxy (poly) ethylene glycol (poly)propylene glycol (poly)butylene glycol mono(meth)acrylate, ethoxy (poly)ethylene glycol mono(meth)acrylate, ethoxy (poly)propylene glycol mono (meth)acrylate, ethoxy (poly)butylene glycol mono(meth) acrylate, ethoxy (poly)ethylene glycol (poly)propylene glycol mono(meth)acrylate, ethoxy (poly)ethylene glycol (poly)butylene glycol mono(meth)acrylate, ethoxy (poly) propylene glycol (poly)butylene glycol mono(meth) acrylate, and ethoxy (poly)ethylene glycol (poly)prpopylene glycol (poly)butylene glycol mono(meth)acrylate may be cited. It is important that the first esterified product ($a^1$) should possess hydrophobicity in the short-chain alcohol of the side chain thereof.

From the viewpoint of easy copolymerization, the side chain preferably contains many ethylene glycol units. The esterified product ($a^1$), therefore, is preferably an alkoxy (poly)ethylene glycol mono(meth)acrylate having an average addition mol number in the range of 1 to 97, preferably 1 to 10.

As concrete examples of the second esterified product ($a^2$), methoxy polyethylene glycol mono(meth)acrylate, methoxy polyethylene glycol (poly)propylene glycol mono(meth)acrylate, methoxy polyethylene glycol (poly)butylene glycol mono(meth)acrylate, methoxy polyethylene glycol (poly)propylene glycol (poly)butylene glycol mono(meth)acrylate, ethoxy polyethylene glycol mono(meth)acrylate, ethoxy polyethylene glycol (poly)propylene glycol mono(meth)acrylate, ethoxy polyethylene glycol (poly)butylene glycol mono(meth)acrylate, and ethoxy polyethylene glycol (poly)propylene glycol (poly)butylene glycol mono(meth)acrylate may be cited.

To obtain a high water-reducing properties, it is important that cement particles should be dispersed by the steric repellency and hydrophilicity of an alcohol chain having an average addition mol number in the range of 4 to 100 in the second esterified product ($a^2$). For this purpose, the polyalkylene glycol chain is preferably incorporated therein many oxyethylene groups. Therefore, a polyethylene glycol chain is the most preferable. The average addition mol number of the alkylene glycol chain, n, in the second esterified product ($a^2$) may be in the range of 4 to 100, preferably 11 to 100.

As concrete examples of the (meth)acrylic acid (salt) monomer which can be used in the method for the production of the polymer of this invention, acrylic acid, methacrylic acid, and monovalent metal salts, divalent metal salts, ammonium salts, and organic amine salts of such acids may be cited. These (meth)acrylic acid (salt) monomers may be used either singly or in the form of a mixture of two or more members.

As concrete examples of the monomer copolymerizable with the monomer components, i.e., the esterified product monomer and the (meth)acrylic acid (salt) monomer which can be used in the method for the production of the polymer of this invention, dicarboxylic acids such as maleic acid, fumaric acid, citraconic acid, messaconic acid, and itaconic acid; monoesters or diesters of these dicarboxylic acids with alcohols represented by the formula; $HO(R^{11}O)_rR^{12}$ (wherein $R^1O$ represents one species or a mixture of two or more species of oxyalkylene groups of 2 to 4 carbon atoms, providing that in the case of a mixture of two or more species, the oxyalkylene groups may be added in a block form or a random form, r represents an average addition mol number of the oxyalkylene group, and is an integer in the range of 1 to 100, and $R^{12}$ represents a hydrogen atom or an alkyl group of 1 to 22 carbon atoms, preferably 1 to 15 carbon atoms); unsaturated amides such as (meth)acrylamide and (meth)acryl alkyl amides; vinyl esters such as vinyl acetate and vinyl propionate; unsaturated sulfonic acids such as vinyl sulfonic acid, (meth)allyl sulfonic acid, sulfoethyl (meth)acrylate, 2-methyl propane sulfonic acid (meth)acrylamide, and styrene sulfonic acid, and the monovalent metal salts, divalent metal salts, ammonium salts, and organic amine salts thereof; aromatic vinyls such as styrene and .-methyl styrene; esters of phenyl group-containing alcohols such as aliphatic alcohols of 1 to 18, preferably 1 to 15 carbon atoms or benzyl alcohol with (meth)acrylic acid; polyalkylene glycol mono(meth)acrylates; and polyalkylene glycol mono(meth)ally ethers may be cited. These monomers may be used either singly or in the form of a mixture of two or more members.

The cement dispersant of this invention which has as a main component thereof the copolymer obtained as described above can manifest excellent cement-dispersing properties and slump-retaining properties.

The cement dispersant according this invention can incorporate therein at least one cement dispersant selected from the group consisting of naphthalene type cement dispersants, aminosulfonic acid type cement dispersants, polycarboxylic acid type cement dispersants, and lignin type cement dispersants which have been known to the art, in addition to the polymer component specified above. The cement dispersant according this invention may be formed solely of the polymer mentioned above or, when necessary, may incorporate therein various components mentioned above and to be shown herein below so as to acquire additional values. A composition of such additional components to be incorporated varies largely with the presence or absence of additive function aimed at. It cannot be specified uniquely but may be varied copiously from the mode of using the polymer wholly (100% by weight) or as a main component to the mode of adding the polymer component mentioned above as a high additive value component in a suitable amount to the conventional cement dispersant. The content of the polycarboxylic acid type copolymer in the cement dispersant according to this invention, however, may be generally in the range of 5 to 100% by weight, preferably in the range of 50 to 100% by weight, based on the total amount of all the components of the composition.

The cement dispersant according to this invention may additionally incorporate therein an air entraining agent, a cement wetting agent, an expanding agent, a water-proofing agent, a retarding agent, an accelerating agent, a water-soluble macromolecular substance, a thickener, a coagulating agent, a dry shrinkage allaying agent, a strength enhancer, a cure accelerator, and a defoaming agent besides conventional cement dispersants.

The cement dispersant having as a main component thereof the polymer obtained as described above can promote dispersion of cement by being incorporated in a cement composition which comprises at least cement and water.

The cement dispersant according to this invention can be used for such hydraulic cements as portland cement, Blite-rich cement, alumina cement, and various mixed cements or for hydraulic materials other than cements, such as gypsum.

Since the cement dispersant according to this invention have such actions and effects as described above, it can manifest outstanding effects even in a smaller amount as compared with a conventional cement dispersant. When this cement dispersant is used in mortar or concrete which uses hydraulic cement, for example, it suffices to add the cement dispersant thereto in an amount in the range of 0.001 to 5%, preferably 0.01 to 1%, based on the weight of cement. This addition brings various favorable effects such as accomplishing a high water-reducing ratio, enhancing slump loss preventing ability, decreasing an unit water content, exalting strength, and improving durability. If the added amount is less than 0.001%, the product would be deficient in performance. Conversely, if it exceeds 5%, the excess would bring no proportionate addition to the effect and consequently impair the economy of the use.

The cement dispersant according to this invention preferably contains as its main component a polymer having a specific weight average molecular weight and a specific difference obtained by subtracting a peak top molecular weight from a weight average molecular weight. In this case, the weight average molecular weight of the polycarboxylic acid type copolymer according to this invention may be decided suitably in the optimum range, depending on the kind of expected use, and set within the optimum range of 500 to 500000, preferably 5000 to 300000, in terms of polyethylene glycol determined by gel permeation chromatography. The difference obtained by subtracting the peak top molecular weight from the weight average molecular weight of the polymer must be in the range of 0 to 8000, preferably 0 to 7000. If the weight average molecular weight is less than 500, the shortage would be at a disadvantage in lowering the water-reducing properties of the cement dispersant. If this weight average molecular weight conversely exceeds 500000, the excess would be at a disadvantage in degrading the water-reducing properties and the slump loss preventing ability of the cement dispersant. If the different obtained by subtracting the peak top molecular weight from the weight average molecular weight exceeds 8000, the excess will be at a disadvantage in lowering the slump retaining ability of the produced cement dispersant.

Now, this invention will be more specifically described below with reference to working examples. In the examples, the term "%" refers to "11% by weight" and the term "part" to "part by weight" unless otherwise specified.

EXAMPLE 1

In an externally jacketed glass reaction tank (30 liters in inner volume) provided with a thermometer, a stirrer, a separator of formed water, and a ref lux condenser (condenser), 16500 parts of methoxy poly(n=25)ethylene glycol, 4740 parts (K value=70) of methacrylic acid, 235 parts of paratoluene sulfonic acid hydrate, 5 parts of phenothiazine, and 1060 parts of cyclohexane were placed. Then, the resultant mixture was subjected to the esterification reaction at a reaction temperature of 115° C. 500.5 parts of a cyclohexane solution containing 0.5 part of phenothiazine was separately added dropwise to the top of the condenser column from the time the reflux of cyclohexane is started till the time the esterification reaction is completed. The arrival of the ratio of esterification at 100% was confirmed in about 20 hours. After the same procedure as described above was repeated for several batches, the interior of the reflux condenser as the condenser was checked to find no gel-like substances. The composition, the conditions, and the test results of the reaction in the present example are shown in Table 1 below.

EXAMPLE 2

The esterification reaction was carried out by following the procedure of Example 1 while using as a reaction tank an externally jacketed SUS 316 reaction tank (30 m³ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m²) instead. After the completion of the reaction, the interior of the condenser was checked to find no gel-like substances.

EXAMPLE 3

The esterification reaction was carried out by following the procedure of Example 1 while using as a reaction tank an externally jacketed reaction tank to be lined with glass (30 m³ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m²) instead. After the completion of the reaction, the interior of the condenser was checked to find no gel-like substances.

Control 1

In an externally jacketed glass reaction tank (30 liters in inner volume) provided with a thermometer, a stirrer, a separator of formed water, and a reflux condenser (condenser), 16500 parts of methoxy poly(n=25)ethylene glycol, 4740 parts (K value=70) of methacrylic acid, 235 parts of paratoluene sulfonic acid hydrate, 5 parts of phenothiazine, and 1060 parts of cyclohexane were placed. Then, the resultant mixture was subjected to the esterification reaction at a reaction temperature of 115° C. The dropwise addition of a phenothiazine/cyclohexane solution to the top of the condenser column was not carried out during the reaction. The arrival of the ratio of esterification at 100% was confirmed in about 20 hours. After the same procedure as described above was repeated for several batches, the interior of the reflux condenser as the condenser was checked to find the presence of a large amount of gel-like substance. The composition, the conditions, and the test results of the reaction in the present example are shown in Table 1 below.

TABLE 1

| | Composition (Part by weight) | | | | | | | | | |
|---|---|---|---|---|---|---|---|---|---|---|
| | Reaction tank | | | | Dropwise Addition to Condenser | | Conditions | | Results Esterification | |
| | Methoxy poly(n = 25) ethyleneglycol | Methacrylic acid | Cyclo-hexane | Paratoluene sulfonic acid | Pheno-thiazine | Pheno-thiazine | Cyclo-hexane | Reaction temperature (° C.) | Jacket temperature (° C.) | ratio (%)/ Reaction time (hr) | Impurity |
| Example 1 | 16,500 | 4,700 | 1,060 | 235 | 5 | 0.5 | 500 | 115 | 130 | 100%/20 hrs | None |
| Control 1 | 16,500 | 4,700 | 1,060 | 235 | 5 | None | None | 115 | 130 | 100%/20 hrs | Present |

EXAMPLE 4

In an externally jacketed glass reaction tank (30 liters in inner volume) provided with a thermometer, a stirrer, a separator of formed water, and a ref lux condenser (condenser), 16500 parts of methoxypoly(n=25)ethylene glycol, 4740 parts of methacrylic acid, 235 parts of paratoluene sulfonic acid hydrate, 5 parts of phenothiazine, and 1060 parts of cyclohexane were placed. Then, the resultant mixture was subjected to the esterification reaction at a reaction temperature of 115° C. 500.5 parts of a cyclohexane solution containing 0.5 part of phenothiazine was separately added dropwise to the top of the condenser column from the time the reflux of cyclohexane is started till the time the esterification reaction is completed. The arrival of the ratio of esterification at 100% was confirmed in about 20 hours.

Then, 135 parts of an aqueous 49% sodium hydroxide solution and 4890 parts of water were added to 22255 parts of the resultant reaction solution to neutralize the paratoluene sulfonic acid. The neutralized reaction solution and 8 parts of hydroquinone added thereto were heated to 105° C. to expel the cyclohexane in the form of an azeotropic mixture with water. During the expulsion of the cyclohexane by distillation, 301 parts of water containing 1 part of hydroquinone was dropwise added to the top of the condenser column. After the expulsion of the cyclohexane by distillation, adjusting water was added to the residue, to obtain an aqueous 80% esterified product solution (1). Then, after the same procedure as described above was repeated for several batches, the interior of the reflux condenser as the condenser was checked to find no gel-like substances.

The composition, the conditions, and the esterification ratio of the esterification reaction, the neutralization conditions of the neutralization step, the composition of dropwise addition to the condenser during the cyclohexane-expelling step, and the states after the several batches of the operations in the present example are shown in Table 2 below.

EXAMPLE 5

An aqueous 80% esterified product solution was obtained by following the procedure of Example 4 while using as a reaction tank an externally jacketed SUS 316 reaction tank (30 m$^3$ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m$^2$) instead. After the completion of the reaction, the resultant aqueous esterified product solution was checked for the interior of the condenser, to find no gel-like substances.

Example 6

An aqueous 80% esterified product solution was obtained by following the procedure of Example 4 while using as a reaction tank an externally jacketed reaction tank to be lined with glass (30 m$^3$ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m$^2$) instead. After the completion of the reaction, the resultant aqueous esterified product solution was checked for the interior of the condenser, to find no gel-like substances.

EXAMPLE 7

In an externally jacketed glass reaction tank (30 liters in inner volume) provided with a thermometer, a stirrer, a separator of formed water, and a ref lux condenser (condenser), 16500 parts of methoxy poly(n=25)ethylene glycol, 4740 parts of methacrylic acid, 235 parts of paratoluene sulfonic acid hydrate, 5 parts of phenothiazine, and 1060 parts of cyclohexane were placed. Then, the resultant mixture was subjected to the esterification reaction at a reaction temperature of 115° C. 500.5 parts of a cyclohexane solution containing 0.5 part of phenothiazine was separately added dropwise to the top of the condenser column from the time the reflux of cyclohexane is started till the time the esterification reaction is completed. The arrival of the ratio of esterification at 100% was confirmed in about 20 hours. At this time, the interior of the reflux condenser as the condenser was checked to find no gel-like substances.

Then, 135 parts of an aqueous 49% sodium hydroxide solution and 4890 parts of water were added to 22255 parts of the resultant reaction solution to neutralize the paratoluene sulfonic acid. The neutralized reaction solution and 8 parts of hydroquinone added thereto were heated to 105° C. to expel the cyclohexane in the form of an azeotropic mixture with water. During the expulsion of the cyclohexane by distillation, the dropwise addition of a hydroquinone/an aqueous solution to the top of the condenser column was not carried out. After the expulsion of the cyclohexane by distillation, adjusting water was added to the residue, to obtain an aqueous 80% esterified product solution for comparison. Then, after the same procedure as described above was repeated for several batches, the interior of the reflux condenser as the condenser was checked, to find that a large amount of gel-like substance was present in the condenser.

The composition, the conditions, and the esterification ratio of the esterification reaction, the neutralization conditions of the neutralization step, the composition of dropwise addition to the condenser during the cyclohexane-expelling step, and the states after the several batches of the operations in the present example are shown in Table 2 below.

TABLE 2

| | Composition (Part by weight) | | | | | Conditions | | |
|---|---|---|---|---|---|---|---|---|
| | Methoxypoly (n = 25) ethylene glycol | Methacrylic acid | Paratoluene sulfonic acid | Cyclohexane | Phenothiazine | Reaction temperature (° C.) | Reaction time (hr) | Esterification ratio (%) |
| Example 4 | 16,500 | 4,740 | 235 | 1,060 | 5 | 115 | 20 | 100 |
| Example 7 | 16,500 | 4,740 | 235 | 1,060 | 5 | 115 | 20 | 100 |

| | Newtralization Step | | | Dropwise Addition to Condition | | State in Condenser After Cyclohexane Expelling Step |
|---|---|---|---|---|---|---|
| | Esterified Reaction Solution | NaOH | Water | Hydroquinone | Water | |
| Example 4 | 22,255 | 66 | 4,959 | 1 | 300 | None |
| Example 7 | 22,255 | 66 | 4,959 | None | None | Large amount of gel |

EXAMPLE 8

In an externally jacketed reaction tank to be lined with glass (30 m$^3$ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m², 16500 parts of methoxy poly(n=25)ethylene glycol, 4740 parts of methacrylic acid, 235 parts of paratoluene sulfonic acid monohydrate, 5 parts of phenothiazine, and 1060 parts of cyclohexane were placed. Then, the resultant mixture was subjected to the esterification reaction at a reaction temperature of 115° C. Separately, a mixture of a cyclohexane solution (A) containing phenothiazine in which the concentration of phenothiazine in cyclohexane was adjusted to 1000 ppm by weight with a part of the residue of condensate (B) (mainly cyclohexane) which was circulated from the water separator to the reaction tank was sprayed at a rate of the cyclohexane solution (A) of 0.35 part/minute and at a rate of the part of the residue of condensate (B) of 20 parts/minute, respectively, to the top of the condenser column through a nozzle part disposed upwardly in the condenser from the time the reflux of cyclohexane is started till the time the esterification reaction is completed.

The arrival of the ratio of esterification at 100% was confirmed in about 20 hours. Then, 135 parts of an aqueous 49% sodium hydroxide solution and 4890 parts of water were added to the resultant reaction solution to neutralize the paratoluene sulfonic acid. The neutralized reaction solution and 8 parts of hydroquinone added thereto were heated to expel the cyclohexane in the form of an azeotropic mixture with water. During the expulsion of the cyclohexane by distillation, 301 parts of water containing 1 part of hydroquinone was dropwise added to the top of the condenser column. After the expulsion of the cyclohexane by distillation, adjusting water was added to the residue, to obtain an aqueous 80% esterified product solution. Then, after the same procedure as described above was repeated for three batches, the interior of the condenser was checked visually to find no gel-like substances. Further, after the same batch operation continued over a period of one year, the interior of the condenser was checked visually to find that only a trace amount of a gel-like substance was generated therein, which result was compared with that obtained by the following Example 11 after one year operation, to find that the amount of the generated gel-like substance was much smaller as by not more than 1/10 time than that of Example 11, as checked visually.

The composition, the conditions, the composition of the antigelling agent solution which was sprayed to the top of the condenser column, the conditions of the partially neutralization step, the conditions of the solvent-expelling step, and the test results in the present example are shown in Tables 3 to 5 below.

EXAMPLE 9

The esterification reaction was carried out by following the procedure of Example 8 while using as a reaction tank an externally jacketed SUS 316 reaction tank (30 m³ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m²) instead. After the completion of the reaction, the interior of the condenser was checked visually to find no gel-like substances. Further, after the same batch operation continued over a period of one year, the interior of the condenser was checked visually to find that only a trace amount of a gel-like substance was generated therein.

EXAMPLE 10

The esterification reaction was carried out by following the procedure of Example 8 while using as a reaction tank an externally jacketed glass reaction tank (30 liters in inner volume) provided with a thermometer, a stirrer, a separator of formed water, and a reflux condenser (condenser) instead. After the completion of the reaction, the interior of the condenser was checked visually to find no gel-like substances. Further, after the same batch operation continued over a period of one year, the interior of the reflux condenser as the condenser was checked visually to find that only a trace amount of a gel-like substance was generated therein.

EXAMPLE 11

In an externally jacketed reaction tank to be lined with glass (30 m³ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m²), 16500 parts of methoxy poly(n=25)ethylene glycol, 4740 parts of methacrylic acid, 235 parts of paratoluene sulfonic acid monohydrate, 5 parts of phenothiazine, and 1060 parts of cyclohexane were placed. Then, the resultant mixture was subjected to the esterification reaction at a reaction temperature of 115° C. Separately, a mixture of a cyclohexane solution (A) containing phenothiazine in which the concentration of phenothiazine in cyclohexane was adjusted to 1000 ppm by weight with a part of the residue of condensate (B) (mainly cyclohexane) which was circulated from the water separator to the reaction tank was sprayed at a rate of the cyclohexane solution (A) of 0.35 part/minute and at a rate of the part of the residue of condensate (B) of 20 parts/minute, respectively, to the top of the condenser column through a nozzle part disposed downwardly in the condenser from the time the reflux of cyclohexane is started till the time the esterification reaction is completed.

The arrival of the ratio of esterification at 100% was confirmed in about 20 hours. Then, 135 parts of an aqueous 49% sodium hydroxide solution and 4890 parts of water were added to the resultant reaction solution to neutralize the paratoluene sulfonic acid. The neutralized reaction solution and 8 parts of hydroquinone added thereto were heated to expel the cyclohexane in the form of an azeotropic mixture with water. During the expulsion of the cyclohexane by distillation, 301 parts of water containing 1 part of hydroquinone was dropwise added to the top of the condenser column. After the expulsion of the cyclohexane by distillation, adjusting water was added to the residue, to obtain an aqueous 80% esterified product solution. Then, after the same procedure as described above was repeated for three batches, the interior of the condenser was checked visually to find no gel-like substances. Further, after the same batch operation continued over a period of one year, the interior of the condenser was checked visually to find that a very small amount of a gel-like substance was generated therein, which result was compared with that obtained by the above Example 8 after one year operation, to find that the amount of the generated gel-like substance was larger as by not less than 10 times than that of Example 8, as checked visually.

The composition, the conditions, the composition of the antigelling agent solution which was sprayed to the top of the condenser column, the conditions of the partially neutralization step, the conditions of the solvent-expelling step, and the test results in the present example are shown in Tables 3 to 5 below.

EXAMPLE 12

The esterification reaction was carried out by following the procedure of Example 11 while using as a reaction tank an externally jacketed SUS 316 reaction tank (30 min inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m$^2$) instead. After the completion of the reaction, the interior of the condenser was checked visually to find no gel-like substances. Further, after the same batch operation continued over a period of one year, the interior of the condenser was checked visually to find that a very small amount of a gel-like substance was generated therein.

EXAMPLE 13

The esterification reaction was carried out by following the procedure of Example 11 while using as a reaction tank an externally jacketed glass reaction tank (30 liters in inner volume) provided with a thermometer, a stirrer, a separator of formed water, and a reflux condenser (condenser) instead. After the completion of the reaction, the interior of the reflux condenser as the condenser was checked visually to find no gel-like substances. Further, after the same batch operation continued over a period of one year, the interior of the condenser was checked visually to find that a very small amount of a gel-like substance was generated therein.

EXAMPLE 14

In an externally jacketed reaction tank to be lined with glass (30 m$^3$ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m$^2$), 16500 parts of methoxy poly(n=25)ethylene glycol, 4740 parts of methacrylic acid, 235 parts of paratoluene sulfonic acid monohydrate, 5 parts of phenothiazine, and 1060 parts of cyclohexane were placed. Then, the resultant mixture was subjected to the esterification reaction at a reaction temperature of 115° C. Separately, only a cyclohexane solution (A) containing phenothiazine in which the concentration of phenothiazine in cyclohexane was adjusted to 1000 ppm by weight was sprayed at a rate of 0.35 part/minute to the top of the condenser column through a nozzle part disposed downwardly in the condenser from the time the reflux of cyclohexane is started till the time the esterification reaction is completed.

The arrival of the ratio of esterification at 100% was confirmed in about 20 hours. Then, 135 parts of an aqueous 49% sodium hydroxide solution and 4890 parts of water were added to the resultant reaction solution to neutralize the paratoluene sulfonic acid. The neutralized reaction solution and 8 parts of hydroquinone added thereto were heated to expel the cyclohexane in the form of an azeotropic mixture with water. During the expulsion of the cyclohexane by distillation, 301 parts of water containing 1 part of hydroquinone was dropwise added to the top of the condenser column. After the expulsion of the cyclohexane by distillation, adjusting water was added to the residue, to obtain an aqueous 80% esterified product solution. Then, after the same procedure as described above was repeated for three batches, the interior of the condenser was checked visually to find no gel-like substances. Further, after the same batch operation continued over a period of one year, the interior of the condenser was checked visually to find the formation of a gel-like substance, which result was compared with that obtained by the above Example 8 after one year operation, to find that the amount of the generated gel-like substance was larger as by not less than 1000 times than that of Example 8, as checked visually.

The composition, the conditions, the composition of the antigelling agent solution which was sprayed to the top of the condenser column, the conditions of the partially neutralization step, the conditions of the solvent-expelling step, and the test results in the present example are shown in Tables 3 to 5 below.

Control 2

In an externally jacketed glass reaction tank (30 liters in inner volume) provided with a thermometer, a stirrer, a separator of formed water, and a ref lux condenser (condenser), 16500 parts of methoxy poly(n=25)ethylene glycol, 4740 parts of methacrylic acid, 235 parts of paratoluene sulfonic acid monohydrate, 5 parts of phenothiazine, and 1060 parts of cyclohexane were placed. Then, the resultant mixture was subjected to the esterification reaction at a reaction temperature of 115° C. In this experiment, no operations using a condensate residue nor an antigelling agent solution to be acted were carried out from the time the reflux of cyclohexane is started till the time the esterification reaction is completed.

The arrival of the ratio of esterification at 100% was confirmed in about 20 hours. Then, 135 parts of an aqueous 49% sodium hydroxide solution and 4890 parts of water were added to the resultant reaction solution to neutralize the paratoluene sulfonic acid. The neutralized reaction solution and 8 parts of hydroquinone added thereto were heated to expel the cyclohexane in the form of an azeotropic mixture with water. During the expulsion of the cyclohexane by distillation, 301 parts of water containing 1 part of hydroquinone was dropwise added to the top of the condenser column. After the expulsion of the cyclohexane by distillation, adjusting water was added to the residue, to obtain an aqueous 80% esterified product solution. Then, after the same procedure as described above was repeated for three batches, the interior of the condenser was checked visually to find that a large amount of gel-like substances was confirmed.

The composition, the conditions, the composition of the antigelling agent solution which was sprayed to the top of the condenser column, the conditions of the partially neutralization step, the conditions of the solvent-expelling step, and the test results in the present example are shown in Tables 3 to 5 below.

For Control 2 which permitted easy observation of gel-like substance, the interior of the ref lux condenser as the condenser was observed periodically, to find that the gel-like substance was formed consciously at the top of the condenser column, and that the gel-like substance thus formed was partially dropped inside the condenser and thus the formation of gel-like substance was confirmed wholly in the condenser.

TABLE 3

| | Composition (Part by weight) | | | | | Conditions | | | |
|---|---|---|---|---|---|---|---|---|---|
| | Methoxypoly (n = 25) ethylene glycol | Methacrylic acid | Cyclo-hexane | Paratoluene sulfonic acid | Pheno-thiazine | Reaction temperature (° C.) | Jacket temperature (° C.) | Reaction time (hr) | Esterification ratio (%) |
| Example 8 | 16500 | 4740 | 1060 | 235 | 5 | 115 | 130 | 20 | 100 |
| Example 11 | 16500 | 4740 | 1060 | 235 | 5 | 115 | 130 | 20 | 100 |
| Example 14 | 16500 | 4740 | 1060 | 235 | 5 | 115 | 130 | 20 | 100 |
| Control 2 | 16500 | 4740 | 1060 | 235 | 5 | 115 | 130 | 20 | 100 |

TABLE 4

| | Condition of Action with Antigelling Agent Solution | | | Result | |
|---|---|---|---|---|---|
| | Antigelling Agent Solution (A) (Part/min) | Condensate Residue (B) (Part/min) | Direction of Nozzle | Gel after 3 batches | After 1 year |
| | | | | | Gel / Amount of Gel |
| Example 8 | 0.35 | 20 | Upward | None | Trace Amount / Assuming to be 1 |
| Example 11 | 0.35 | 20 | Downward | None | Small Amount / Not less than 10 |
| Example 14 | 0.35 | None | Downward | None | Present / Not less than 1000 |
| Control 2 | None | None | None | Present | — / — |

Concentration of antigelling agent Solution (A): The concentration of phenothiazine in cyclohexane solution was adjusted to 1000 ppm by weight.

TABLE 5

| | Composition of Newtralization Step (Part by weight) | | | Antigelling Solution to be Sprayed to Column Top during Cyclohexane-Expelling Step | |
|---|---|---|---|---|---|
| | Composition after Esterification | NaOH | water | Hydroquinone | water |
| Example 8 | 22,255 | 66 | 4,959 | 1 | 300 |
| Example 11 | 22,255 | 66 | 4,959 | 1 | 300 |
| Example 14 | 22,255 | 66 | 4,959 | 1 | 300 |
| Control 2 | 22,255 | 66 | 4,959 | 1 | 300 |

EXAMPLE 15

In an externally jacketed glass reaction tank (30 liters in inner volume) provided with a thermometer, a stirrer, a separator of formed water, and a ref lux condenser (condenser), 8200 parts of water was placed and, with the interior of the reaction tank replaced with nitrogen gas and kept stirred meanwhile, heated to 80° C. in an atmosphere of nitrogen. Then, to the reaction tank, a solution of 94 parts of 3-mercapto propionic acid in 13100 parts of the aqueous 80% esterified product solution (1) obtained in Example 4 was added dropwise over a period of four hours, and at the same time, a solution of 125 parts of ammonium persulfate in 1000 parts of water was added dropwise over a period of five hours. After the dropwise addition was completed, the resultant reaction mixture was left standing at 80° C. for one hour. Then, by further adjusting this reaction mixture with sodium hydroxide to a pH value of 8, polycarboxylic acid (1) of this invention was found to have a weight average molecular weight of 21000, in terms of polyethylene glycol determined by gel permeation chromatography.

By using the polycarboxylic acid (1) thus obtained in its unmodified form as a cement dispersant, a cement composition (1) was prepared in accordance with the method for mortar test and tested for flow value. The results are shown in Table 6 below.

Method for Mortar Test

A cement composition (1) was prepared by kneading 240 parts of water containing the cement dispersant [polycarboxylic acid (1)] obtained as described above, 400 parts of ordinary portland cement (made by Taiheiyo Cement) as a cement, and 800 parts of standard sand produced at Toyoura by the use of a mortar mixer. The amount of the cement dispersant added is shown in Table 6 below.

Then, this cement composition (1) was placed to fill a hollow cylinder, 55 mm in diameter and 55 mm in height. The cylinder was gently raised vertically to allow the cement composition (1) to spread. The major diameter and the minor diameter of the spread cement composition (1) and the average thereof was reported as a flow value.

EXAMPLE 16

The esterification reaction was carried out by following the procedure of Example 4 while changing the amount of the methoxy poly(n=25)ethylene glycol to be used to 19430 parts and the amount of methacrylic acid to be used to 1810 parts (K value=215). After the arrival of the ratio of esterification at about 99% was confirmed in about 90 hours, 104 parts of an aqueous 49% sodium hydroxide solution and 4900 parts of water were added to the esterified product to neutralize the paratoluene sulfonic acid. The resultant product and 8 parts of hydroquinone added thereto were heated to expel the cyclohexane in the form of an azeotropic mixture with water. After the expulsion of the cyclohexane by distillation, adjusting water was added to the residue, to obtain an aqueous 80% esterified product solution (2).

In an externally jacketed glass reaction tank (30 liters in inner volume) provided with a thermometer, a stirrer, a separator of formed water, and a reflux condenser (condenser), 8200 parts of water was placed and, with the interior of the reaction tank replaced with nitrogen gas and kept stirred meanwhile, heated to 80° C. in an atmosphere of nitrogen. Then, a solution of 58 parts of 3-mercapto propionic acid in 13700 parts of the aqueous 80% esterified product solution (2) obtained as described above was added dropwise over a period of four hours, and at the same time, a solution of 122 parts of ammonium persulfate in 2300 parts of water was added dropwise over a period of five hours. After the dropwise addition was completed, the resultant reaction mixture was left standing at 80° C. for one hour. Then, by further adjusting this reaction mixture with sodium hydroxide to a pH value of 8, polycarboxylic acid (2) was found to have a weight average molecular weight of 19700, in terms of polyethylene glycol determined by gel permeation chromatography.

By using the polycarboxylic acid (2) obtained as described above in its unmodified form as a cement dispersant, a cement composition (2) was prepared in accordance with the method for mortar test and tested for flow value in the same manner as in Example 15. The results are shown in Table 6 below.

TABLE 6

| | Cement dispersant | Amount added[a] | Flow Value |
|---|---|---|---|
| Example 15 | Polycarboxylic acid (1) | 0.15% | 105 mm |
| Example 16 | Polycarboxylic acid (2) | 1.0% | 60 mm |

[a])Solid content as a reduced mass of cement (% by weight)

It is clearly noted from the results shown in Table 6 that the flow value markedly fell and consequently the cement-dispersing ability was decreased when the K value surpassed the upper limit which is described to be preferably defined by this invention.

EXAMPLE 17

In an externally jacketed reaction tank to be lined with glass (30 m$^3$ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m$^2$), 16500 parts of methoxy poly(n=25)ethylene glycol, 4740 parts of methacrylic acid, 235 parts of paratoluene sulfonic acid monohydrate, 5 parts of phenothiazine, and 1060 parts of cyclohexane were placed. Then, the resultant mixture was subjected to the esterification reaction at a reaction temperature of 115° C. Separately, a mixture of a cyclohexane solution (A) containing phenothiazine in which the concentration of phenothiazine in cyclohexane was adjusted to 1000 ppm by weight with a part of the residue of condensate (B) (mainly cyclohexane) which was circulated from the water separator to the reaction tank was sprayed at a rate of the cyclohexane solution (A) of 0.35 part/minute and at a rate of the part of the residue of condensate (B) of 20 parts/minute, respectively, to the top of the condenser column through a nozzle part disposed upwardly in the condenser from the time the reflux of cyclohexane is started till the time the esterification reaction is completed. At the same time, a part of the condensate residue to be returned to the reaction tank from the water separator was also sprayed as the antigelling agent to the joint part (flange part) on the reaction tank side via a spray nozzle at a rate of 10 to 15 parts/minute.

The arrival of the ratio of esterification at 99% was confirmed in about 20 hours. Then, 135 parts of an aqueous 49% sodium hydroxide solution and 4890 parts of water were added to the resultant reaction solution to neutralize the paratoluene sulfonic acid. The neutralized reaction solution and 8 parts of hydroquinone added thereto were heated to expel the cyclohexane in the form of an azeotropic mixture with water. During the expulsion of the cyclohexane by distillation, 301 parts of water containing 1 part of hydroquinone was dropwise added to the top of the condenser column. After the expulsion of the cyclohexane by distillation, adjusting water was added to the residue, to obtain an aqueous 80% esterified product solution. After the completion of the esterification reaction thus performed, the content in the reaction tank was passed through a pole filter (100 mesh) and the gel-like substance remaining on the pole filter was weighed, to find to be 0.3 kg.

After the same operation as described above was repeated over a period of one year, the joint part (flange part) of the overhead line on the reaction tank side and the interior of the condenser were checked visually to find no gel-like substances. From these results, the number of washing the interior of the condenser for preventing the blockage with gel (about 1 time/3 months) could be remarkably decreased as compared with the case of supplying no antigelling agents to the interior of the condenser (at least 1 time/1 month).

The composition, the conditions, the conditions of using an antigelling agent to an overhead line, the conditions of using an antigelling agent to a condenser, the conditions of disposing a nozzle, and the conditions of the partially neutralization step in the present example are shown in Tables 7 to 9 below.

EXAMPLE 18

In an externally jacketed reaction tank to be lined with glass (30 m$^3$ in inner volume) provided with a thermometer, a stirrer, a separator of formed water, and a shell-and-tube type condenser (comprising a shell of 750 mm in inside diameter and 4000 mm in length, and 485 tubes of 24 mm in inside diameter and having a heat transfer surface area of 150 m$^2$), 16500 parts of methoxy poly(n=25)ethylene glycol, 4740 parts of methacrylic acid, 235 parts of paratoluene sulfonic acid monohydrate, 5 parts of phenothiazine, and 1060 parts of cyclohexane were placed. Then, the resultant mixture was subjected to the esterification reaction at a reaction temperature of 115° C. Separately, a mixture of a cyclohexane solution (A) containing phenothiazine in which the concentration of phenothiazine in cyclohexane was adjusted to 1000 ppm by weight with a part of the residue of condensate (B) (mainly cyclohexane) which was circulated from the water separator to the reaction tank was sprayed at a rate of the cyclohexane solution (A) of 0.35 part/minute and at a rate of the part of the residue of condensate (B) of 20 parts/minute, respectively, to the top of the condenser column through a nozzle part disposed upwardly in the condenser from the time the reflux of cyclohexane is started till the time the esterification reaction is completed. In the present example, however, no antigelling agent solutions were acted on the joint part (flange part) on the reaction tank side.

The arrival of the ratio of esterification at 99% was confirmed in about 20 hours. Then, 135 parts of an aqueous 49% sodium hydroxide solution and 4890 parts of water were added to the resultant reaction solution to neutralize the paratoluene sulfonic acid. The neutralized reaction solution and 8 parts of hydroquinone added thereto were heated to expel the cyclohexane in the form of an azeotropic mixture with water. During the expulsion of the cyclohexane by distillation, 301 parts of water containing 1 part of hydroquinone was dropwise added to the top of the condenser column. After the expulsion of the cyclohexane by distillation, adjusting water was added to the residue, to obtain an aqueous 80% esterified product solution. After the completion of the esterification reaction thus performed, the content in the reaction tank was passed through a pole filter (100 mesh) and the gel-like substance remaining on the pole filter was weighed, to find to be 3 kg. By comparing this result with that obtained in Example 17, it may be observed that the formation of gel at the flange part could be repressed and thus the amount of this formed gel to be dropped into and stored in the reaction tank could be decreased by about 1/10 time, by making the antigelling agent [a mixer solution of (A) and (B)] acted on the joint part (flange part) on the reaction tank side.

After the same operation as described above was repeated over a period of one year, the joint part (flange part) of the overhead line on the reaction tank side and the interior of the condenser were checked visually to find no gel-like substances. From these results, the number of washing the interior of the condenser for preventing the blockage with gel (about 1 time/3 months) could be remarkably decreased as compared with the case of supplying no antigelling agents to the interior of the condenser (at least 1 time/1 month).

The composition, the conditions, the conditions of using an antigelling agent to an overhead line, the conditions of using an antigelling agent to a condenser, the conditions of disposing a nozzle, and the conditions of the partially neutralization step in the present example are shown in Tables 7 to 9 below.

TABLE 9

| Composition of neutralization Step (Part by weight) | | |
|---|---|---|
| Composition after Esterification | NaOH | water |
| 22,255 | 66 | 4,959 |

The entire disclosure of Japanese Patent Application Nos. 10-268121, 10-328684, and 11-99335 filed on Sep. 22, 1998, Nov. 18, 1998, and Apr. 6, 1999, respectively, including specification, claims, drawings and summary are incorporated herein by reference in its entirety.

What is claimed is:

1. A method for the production of a polycarboxylic acid type copolymer for the use in a cement dispersant which comprises reacting by the esterification of an alcohol represented by the formula (1):

$$R^1O(R^2O)_nH \quad (1)$$

wherein $R^1$ represents a hydrocarbon group of 1 to 30 carbon atoms, $R^2O$ represents an oxyalkylene group of 2 to 18 carbon atoms, providing that the repeating units, $R^2O$, may be the same or different and that when the $R^2O$'s are in the form of a mixture of two or more species, the repeating units, $R^2O$, may be added either in a block form or in a random form, and n represents an average addition mol number of oxyalkylene groups and is in the range of 1 to 300, with (meth)acrylic acid while causing an antigelling agent to act on a distillate, to obtain an alkoxy polyalkylene glycol mono(meth)acrylic acid type monomer (a), and copolymerizing 5 to 98% by weight of said alkoxy polyalkylene glycol mono(meth)acrylic acid type monomer (a), 95 to 2% by weight of a (meth)acrylic acid type monomer (b) represented by the following formula (2):

TABLE 7

| | Composition (Part by weight) | | | | | Conditions | | | |
|---|---|---|---|---|---|---|---|---|---|
| | Methoxypoly (n = 25) ethylene glycol | Methacrylic acid | Cyclo-hexane | Paratoluene sulfonic acid | Pheno-thiazine | Reaction temperature (° C.) | Jacket temperature (° C.) | Reaction time (hr) | Esterification ratio (%) |
| Example 17 | 16,500 | 4,740 | 1,060 | 235 | 5 | 115 | 130 | 20 | 99 |
| Example 18 | 16,500 | 4,740 | 1,060 | 235 | 5 | 115 | 130 | 20 | 99 |

TABLE 8

| | Conditions of Antigelling Agent on Overhead Line | | | Antigelling Solution to be Sprayed to Column Top during Cyclohexane-Expelling | | |
|---|---|---|---|---|---|---|
| | Kind of Antigelling Agent Acted on Overhead Line | Amount of Antigelling Agent Circulated (Part/min) | Position of Disposed Nozzle | Condition of Action with Antigelling Agent Solution | | |
| | | | | Antigelling Agent Solution (A)[1) ] (Part/min) | Condensate Residue (B) (Part/min) | Direction of Nozzle |
| Example 17 | Part of Condensate Residue | 10–15 | Disposed on Joint part on Reaction Tank side | 0.35 | 20 | Upward |
| Example 18 | — | 0 | No Nozzle Disposed | 0.35 | 20 | Upward |

Concentration of antigelling agent solution (A): The concentration of phenothiazine in cyclohexane solution was adjusted to 1000 ppm by weight.

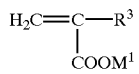
(2)
wherein $R^3$ represents a hydrogen atom or a methyl group, and $M^1$ represents a hydrogen atom, a monovalent metal element, a divalent metal element, an ammonium group, or an organic amine group,
and 0 to 50% by weight of a monomer (c) copolymerizable with the monomers mentioned above, providing that the total amount of the monomers (a), (b), and (c) be 100% by weight.
* * * * *